US008822652B2

(12) United States Patent
Pierres et al.

(10) Patent No.: US 8,822,652 B2
(45) Date of Patent: Sep. 2, 2014

(54) MONOCLONAL ANTIBODIES THAT BIND B7H6 AND USES THEREOF

(75) Inventors: Michel Pierres, Marseilles (FR); Eric Vivier, Cassis (FR); Myriam Baratin, Cassis (FR)

(73) Assignee: Institut National de la Sante et de la Recherche Medicale, Paris (FR)

( * ) Notice: Subject to any disclaimer, the term of this patent is extended or adjusted under 35 U.S.C. 154(b) by 8 days.

(21) Appl. No.: 13/515,276

(22) PCT Filed: Dec. 8, 2010

(86) PCT No.: PCT/IB2010/003411
§ 371 (c)(1),
(2), (4) Date: Sep. 7, 2012

(87) PCT Pub. No.: WO2011/070443
PCT Pub. Date: Jun. 16, 2011

(65) Prior Publication Data
US 2013/0004432 A1    Jan. 3, 2013

Related U.S. Application Data

(60) Provisional application No. 61/285,018, filed on Dec. 9, 2009.

(51) Int. Cl.
*C07K 16/28* (2006.01)
*A61K 39/395* (2006.01)

(52) U.S. Cl.
USPC ............... 530/388.22; 530/391.7; 424/144.1; 424/181.1

(58) Field of Classification Search
CPC ...................... C07K 16/2827; C07K 16/2803
See application file for complete search history.

(56) References Cited

U.S. PATENT DOCUMENTS

| | | |
|---|---|---|
| 4,331,647 A | 5/1982 | Goldenberg |
| 4,486,414 A | 12/1984 | Pettit |
| 4,816,444 A | 3/1989 | Pettit et al. |
| 4,879,278 A | 11/1989 | Pettit et al. |
| 4,880,935 A | 11/1989 | Thorpe |
| 4,883,662 A | 11/1989 | Stout |
| 4,978,744 A | 12/1990 | Pettit et al. |
| 4,986,988 A | 1/1991 | Pettit et al. |
| 5,076,973 A | 12/1991 | Pettit et al. |
| 5,082,833 A | 1/1992 | Shamsuddin |
| 5,122,368 A | 6/1992 | Greenfield et al. |
| 5,138,036 A | 8/1992 | Pettit et al. |
| 5,410,024 A | 4/1995 | Pettit et al. |
| 5,504,191 A | 4/1996 | Pettit et al. |
| 5,521,284 A | 5/1996 | Pettit et al. |
| 5,530,097 A | 6/1996 | Pettit et al. |
| 5,554,725 A | 9/1996 | Pettit |
| 5,556,623 A | 9/1996 | Barton et al. |
| 5,571,698 A | 11/1996 | Ladner et al. |
| 5,580,717 A | 12/1996 | Dower et al. |
| 5,599,902 A | 2/1997 | Pettit et al. |
| 5,622,929 A | 4/1997 | Willner et al. |
| 5,635,483 A | 6/1997 | Pettit et al. |
| 5,643,573 A | 7/1997 | Barton et al. |
| 5,663,149 A | 9/1997 | Pettit et al. |
| 5,665,358 A | 9/1997 | Barton et al. |
| 5,665,860 A | 9/1997 | Pettit et al. |
| 5,693,762 A | 12/1997 | Queen et al. |
| 5,780,588 A | 7/1998 | Pettit et al. |
| 5,824,805 A | 10/1998 | King et al. |
| 5,885,793 A | 3/1999 | Griffiths et al. |
| 5,969,108 A | 10/1999 | McCafferty et al. |
| 6,034,065 A | 3/2000 | Pettit et al. |
| 6,040,136 A | 3/2000 | Garrard et al. |
| 6,214,345 B1 | 4/2001 | Firestone et al. |
| 6,239,104 B1 | 5/2001 | Pettit et al. |
| 6,323,315 B1 | 11/2001 | Pettit et al. |
| 6,884,869 B2 | 4/2005 | Senter et al. |
| 7,858,759 B2 * | 12/2010 | Brandt et al. ............ 530/391.7 |
| 2003/0083263 A1 | 5/2003 | Doronina et al. |
| 2009/0220502 A1 | 9/2009 | Brandt et al. |

FOREIGN PATENT DOCUMENTS

| | | |
|---|---|---|
| WO | WO89/12624 | 12/1989 |
| WO | WO02/088172 | 11/2002 |
| WO | WO2004/010957 | 2/2004 |
| WO | WO2008/131242 | 10/2008 |
| WO | WO2009/046407 A2 | 4/2009 |

OTHER PUBLICATIONS

Sequence alignment, 2013, 1 page.*
Anderson, P. et al., "Entrapment of Human Leukocyte Interferon in the Aqueous Interstices of Liposomes", Infection and Immunity, vol. 31(3), pp. 1099-1103 (1981).
Anderson, P. et al., "Increased Local Antitumor Effects of Interleukin 2 Liposomes in Mice with MCA-106 Sarcoma Pulmonary Metastases", Cancer Research, vol. 50, pp. 1853-1856 (1990).
Ansell, S.M. et al., "Inhibition of surviving expression suppresses the growth of aggressive non-Hodgkins' lymphoma", Leukemia, vol. 18, pp. 616-623 (2004).
Baker, Shan, "An In Vivo Model for Squamous Cell Carcinoma of the Head and Neck" Laryngoscope, vol. 95, pp. 43-56 (1985).
Bakker-Woudenberg, I.A.J.M., et al., "Liposomes as Carriers of Antimicrobial Agents or Immunomodulatory Agents in the Treatment of Infections", Eur. J. Clin. Microbiol. Infect. Dis., vol. 12, Suppl. 1, pp. 61-67 (1993).
Barao, I. et al., "The Immunobiology of Natural Killer Cells and Bone Marrow Allograft Rejection", Biology of Blood and Marrow Transplantation, vol. 9, pp. 727-741 (2003).

(Continued)

*Primary Examiner* — Ilia Ouspenski

(74) *Attorney, Agent, or Firm* — Nelson Mullins Riley & Scarborough LLP; Jane E. Remillard, Esq.; Jeanne M. DiGiorgio

(57) ABSTRACT

Disclosed are monoclonal antibodies that specifically bind to the B7 family member B7H6, including antibodies capable of inhibiting the interaction of B7H6 with NKp30. Also disclosed are anti-B7H6 antibody-drug conjugates comprising an anti-B7H6 monoclonal antibody conjugated to a therapeutic agent. The anti-B7H6 antibodies and antibody-drug conjugates are useful in methods for exerting therapeutic effects against B7H6-expressing cells, as well as in diagnostic methods for the detection of B7H6 or B7H6-expressing cells.

23 Claims, No Drawings

(56) References Cited

OTHER PUBLICATIONS

Bartus, R. et al., "Sustained Delivery of Proteins for Novel Therapeutic Products", Science, vol. 281, pp. 1161-1162 (1998).

Bello, L. et al., "Suppression of Malignant Glioma Recurrence in a Newly Developed Animal Model by Endogenous Inhibitors", Clinical Cancer Research, vol. 8, pp. 3539-3548 (2002).

Bird, R. et al., "Single-Chain Antigen-Binding Proteins", Science, vol. 242, pp. 423-426 (1988).

Boye, J. et al., "An overview of the current clinical use of the anti-CD20 monoclonal antibody rituximab" Annals of Oncology, vol. 14, pp. 520-535 (2003).

Boyton, R.J. et al., "Natural killer cells, killer immunoglobulin-like receptors and human leucocyte antigen class I in disease", Clinical and Experimental Immunology, vol. 149, pp. 1-8 (2007).

Braakhuis, B.J.M. et al., "Preclinical in Vivo Activity of 2', 2'—Difluorodeoxycytidine (Gemcitabine) against Human Head and Neck Cancer", Cancer Research, vol. 51, pp. 211-214 (1991).

Brandt, C. et al., "The B7 family member B7-H6 is a tumor cell ligand for the activating natural killer cell receptor NKp30 in humans", Journal of Experimental Medicine, vol. 206(7), pp. 1495-1503 (2009).

Brittenden, J. et al., Natural Killer Cells and Cancer, Cancer, vol. 77, pp. 1226-1243 (1996).

Cao, S. et al., "Antitumor Activity of ZD1694 (Tomudex) against Human Head and Neck Cancer in Nude Mouse Models: Role of Dosing Schedule and Plasma Thymidine", Clinical Cancer Research, vol. 5, pp. 1925-1934 (1999).

Carter, P. et al., "Humanization of an anti-p185$^{HER2}$ antibody for human cancer therapy", PNAS, vol. 89, pp. 4285-4289 (1992).

Carreno, B. et al., "The B7 Family of Ligands and Its Receptors: New Pathways for Costimulation and Inhibition of Immune Responses", Annual Review Immunol., vol. 20, pp. 29-53 (2002).

Chambers, C. et al., "CTLA-4-Mediated Inhibition in Regulation of T Cell Responses: Mechanisms and Manipulation in Tumor Immunotherapy" Annual Rev. Immunol., vol. 19, pp. 565-594 (2001).

Chari, R.V.J. et al., "Immunoconjugates Containing Novel Maytansinoids: Promising Anticancer Drugs", Cancer Research, vol. 52, pp. 127-131 (1992).

Coyle, A. et al., "The expanding B7 superfamily: Increasing complexity in costimulatory signals regulating T cell function", Nature Immunology, vol. 2(3), pp. 203-209 (2001).

Cudkowicz, G. et al., "Peculiar Immunobiology of Bone Marrow Allografts I. Graft Rejection by Irradiated Responder Mice", The Journal of Experimental Medicine, vol. 134, pp. 83-102, (1971).

Cudkowicz, G. et al., "Peculiar Immunobiology of Bone Marrow Allografts. II. Rejection of Parental Grafts by Resistant $F_1$ Hybrid Mice", The Journal of Experimental Medicine, vol. 134, pp. 1513-1528 (1971).

Diefenbach, A. et al., "Strategies for target cell recognition by natural killer cells", Immunological Reviews, vol. 181, pp. 170-184 (2001).

Downs, Jr. L., et al., "Thalidomide and angiostatin inhibit tumor growth in a murine xenograft model of human cervical cancer", Gynecologic Oncology, vol. 98, pp. 203-210 (2005).

Dubowchik, G. et al., "Receptor-mediated and enzyme-dependent targeting of cytotoxic anticancer drugs", Pharmacology & Therapeutics, vol. 83, pp. 67-123 (1999).

Egen, J. et al., CTLA-4: new insights into its biological function and use in tumor immunotherapy, Nature Immunology, vol. 3(7), pp. 611-618 (2002).

Emini, E. et al., "Induction of Hepatitis A Virus—Neutralizing Antibody by a Virus-Specific Synthetic Peptide", Journal of Virology, vol. 55(3), pp. 836-839 (1985).

Ford, C. et al., "Fusion Tails for the Recovery and Purification of Recombinant Proteins", Protein Expression and Purification, vol. 2, pp. 95-107 (1991).

Garnier, J. et al., "Analysis of the Accuracy and Implications of Simple Methods for Predicting the Secondary Structure of Globular Proteins", J. Mol. Biol., vol. 120, pp. 97-120 (1978).

Ghetie, V. et al., "FcRn: the MHC class I-related receptor that is more than an IgG transporter", Immunology Today, vol. 18(12), pp. 592-598 (1997).

Gombotz, W. et al., "Biodegradable Polymers for Protein and Peptide Drug Delivery", Bioconjugate Chem., vol. 6, pp. 332-351 (1995).

Green, L.L. et al., "Antigen-specific human monoclonal antibodies from mice engineered with human Ig heavy and light chain YACs", Nat Genet, May 1994;7(1):13-21.

Grussenmeyer, T. et al., :Complexes of polyoma virus medium T antigen and cellular proteins PNAS, vol. 82, pp. 7952-7954 (1985).

Harasym, T. et al., "Clearance properties of liposomes involving conjugated proteins for targeting", vol. 32, pp. 99-118 (1998).

Herberman, R. et al., "Natural Killer Cells: Their Role in Defenses Against Disease", Science, vol. 214, pp. 24-30 (1981).

Hopp, T. et al., "A short polypeptide marker sequence useful for recombinant protein identification and purification", Bio/Technology, vol. 6, pp. 1204-1210 (1988).

Hopp, T. et al., "Prediction of protein antigenic determinants from amino acid sequences", PNAS, vol. 78(6), pp. 3824-3828 (1981).

Hu, Y. et al., "Antitumor Efficacy of Oblimersen Bcl-2 Antisense Oligonucleotide Alone and in Combination with Vinorelbine in Xenograft Models of Human Non-Small Cell Lung Cancer", Clinical Cancer Research, vol. 10, pp. 7662-7670 (2004).

Huse, W. et al., "Generation of a Large Combinatorial Library of the Immunoglobulin Repertoire in Phage Lambda", Science, vol. 246, pp. 1275-1281 (1989).

Huynh, H. et al., "RAD001 (everolimus) inhibits tumour growth in xenograft models of human hepatocellular carcinoma", J. Cell. Mol. Med., vol. 13(7), pp. 1371-1380 (2009).

Inbar, D. et al., "Localization of Antibody-Combining Sites within the Variable Portions of Heavy and Light Chains", PNAS, vol. 69(9), pp. 2659-2662 (1972).

Jameson, B.A. et al., "The antigenic index: a novel algorithm for predicting antigenic determinants", CABIOS, vol. 4(1), pp. 181-186 (1988).

Johnson, D.A. et al., "Anti-Tumor Activity of CC49-Doxorubicin Immunoconjugates", Anticancer Research, vol. 15, pp. 1387-1394 (1995).

Jones, P. et al., "Replacing the complementarity-determining regions in a human antibody with those from a mouse", Nature, vol. 321, pp. 522-525 (1986).

Karplus, P.A. et al., "Prediction of Chain Flexibility in Proteins", Naturwissenschaften, vol. 72, pp. 212-213 (1985).

Kato, Y. et al., "Modification of Liposomes by Addition of HCO60. I. Targeting of Llposomes to Liver by Addition of HCO60 to Liposomes", Biol. Pharm. Bull., vol. 16(10), pp. 960-964 (1993).

Kennedy, J.H. et al., "Protein-Protein coupling reactions and the applications of protein conjugates", Clinica Chimica Acta, vol. 70, pp. 1-31 (1976).

Kim, Sinil. "Liposomes as Carriers of Cancer Chemotherapy", Drugs, vol. 46(4), 618-38 (1993).

Kohler, G. et al., "Continuous cultures of fused cells secreting antibody of predefined specificity", Nature, vol. 256, pp. 495-497 (1975).

Koide A. et al., "Monobodies: Antibody Mimics Based on the Scaffold of the Fibronectin Type III Domain ", Methods in Molecular Biology, vol. 352, pp. 95-109 (2007).

Kuriakose, M.A. et al., "Interleukin-12 delivered by biodegradable microspheres promotes that antitumor activity of human peripheral blood lymphocytes in a human head and neck tumor xenograft/SCID Mouse Model", Head & Neck, pp. 57-63 (2000).

Lau, A. et al., "Conjugation of Doxorubicin to Monoclonal Anti-carcinoembryonic Antigen Antibody via Novel Thiol-directed Cross-linking Reagents", Bioorganic & Medicinal Chemistry, vol. 3(10), pp. 1299-1304 (1995).

Lau, A. et al., "Novel Doxorubicin-Monoclonal Anti-carcinoembryonic Antigen Antibody Immunoconjugate Activity in vitro" Bioorganic & Medicinal Chemistry, vol. 3(10), pp. 1305-1312 (1995).

Li, L.H. et al., "CC-1065 (NSC 298223), a Novel Antitumor Agent that Interacts Strongly with Double-stranded DNA", Cancer Research, vol. 42, pp. 999-1004 (1982).

(56) References Cited

OTHER PUBLICATIONS

Li. L. et al., "Antiproliferative activity and toxicity of 2-methoxyestradiol in cervical cancer xenograft mice", Int. J. Gynecol Cancer, vol. 15, pp. 301-307 (2005).
Liang, L. et al., "The right place at the right time: novel B7 family members regulate effector T cell responses", Current Opinion in Immunology, vol. 14 pp. 384-390 (2002).
Ljunggren, HG et al., "Prospects for the use of NK cells in immunotherapy of human cancer", Nature Reviews/Immunology, vol. 7, pp. 329-339 (2007).
Ljunggren, HG et al., "In search of the "missing self": MHC molecules and NK Cell recognition", Immunology Today, vol. 11(7), pp. 237-244 (1990).
Lonberg, N. et al. "Antigen-specific human antibodies from mice comprising four distinct genetic modifications" Nature, vol. 368, pp. 856-859 (1994).
Miyakawa, Y. et al., "Establishment of a new model of human multiple myeloma using NOD/SCID/$\gamma_c^{null}$ (NOG) mice", Biochemical and Biophysical Research Communications, vol. 313 pp. 258-262 (2004).
Moretta, A. et al., "Activating Receptors and Coreceptors Involved in Human Natural Killer Cell-Mediated Cytolysis", Annu. Rev. Immunol., vol. 19, pp. 197-223 (2001).
Mosmann, T. et al., "Rapid Colorimetric Assay for Cellular Growth and Survival: Application to proliferation and Cytotoxicity Assays", Journal of Immunological Methods, vol. 65, pp. 55-63 (1983).
Murphy, W. J. et al., "Immunobiology of natural killer cells and bone marrow transplantation: merging of basic and preclinical studies", Immunological Reviews, vol. 181, pp. 279-289 (2001).
Murphy, W.J. et al., "Natural killer cells activated with interleukin 2 in vitro can be adiptively transferred and mediate hematopoietic histocompatibility-1 antigen-specific bone marrow rejection in vivo", Eur. J. Immunol., vol. 20, pp. 1729-1734 (1990).
Murphy, W.J. et al., "An Absence of T Cells in Murine Bone Marrow Allografts Leads to an Increased Susceptibility to Rejection by natural Killer Cells and T Cells", The J. of Immunology, vol. 144(9), pp. 3305-3311 (1990).
Murphy, W.J. et al., "Acute Rejection of Murine Bone Marrow Allografts by Natural Killer Cells and T Cells. Difference in Kinetics and Target Antigens Recognized" J. Exp. Med., vol. 166, pp. 1499-1509 (1987).
Murphy, W.J. et al., "Rejection of Bone Marrow Allografts by Mice with Severe Combined Immune Deficiency (SCID). Evidence that Natural Killer Cells can Mediate the Specificity of Marrow Graft Rejection" J. Exp. Med., vol. 165, pp. 1212-1217 (1987).
Murphy, W.J. et al., Review "Natural Killer Cells and Bone Marrow Transplantation", J. of the National Cancer Institute, vol. 85(18) pp. 1475-1482 (1993).
Nagata, S. et al., "Rapid grouping of monoclonal antibodies based on their topographical epitopes by a label-free competitive immunoassay", J. of Immunological Methods, vol. 292, pp. 141-155 (2004).
National Cancer Institute Booklet, "What you need to know about" Leukemia. (2008).
National Cancer Institute Booklet, "What you need to know about" Multiple Myeloma (2008).
Nemati, F. et al., "Distinctive Potentiating Effects of Cisplatin and/or Ifosfamide Combined with Etoposide in Human Small Cell Lung Carcinoma Xenografts", Clinical Cancer Research, vol. 6, pp. 2075-2086 (2000).
Neville Jr., D. M. et al., "Enhancement of Immunotoxin Efficacy by Acid-cleavable Cross-linking Agents Utilizing Diphtheria Toxin and Toxin Mutants" The J. of Biological Chemistry, vol. 264(25), pp. 14653-14661 (1989).
Nilsson, B. et al., Expression and Purification of Recombinant Insulin-like Growth Factors from *Escherichia coli*, Methods in Enzymology, vol. 198 pp. 3-16 (1991).
Nilsson, B. et al., "Immobilization and purification of enzymes with staphylococcal protein A gene fusion vectors", The EMBO Journal, vol. 4(4), pp. 1075-1080 (1985).

Ohlen, C. et al., "Resistance to H-2-Restricted but not to Allo-H2-Specific Graft and Cytotoxic T Lymphocyte Responses in Lymphoma Mutant", The J. of Immunology, vol. 145, pp. 52-58 (1990).
O'Reilly, R.J et al., "Evaluation of HLA-Haplotype Disparate Parental Marrow Grafts Depleted of T Lymphocytes by Differential Agglutination with a Soybean Lectin and E-Rosette Depletion for the Treatment of Severe Combined Immunodeficiency", Vox Sang. vol. 51, suppl. 2, pp. 81-86 (1986).
Orlandi, R. et al., "Cloning immunoglobulin variable domains for expression by the polymerase chain reaction", PNAS, vol. 86, pp. 3833-3837, (1989).
Ortaldo, J.R. et al., "Heterogeneity of Natural Killer Cells", Am. Rev. Immunol., vol. 2, pp. 359-394 (1984).
Ostro, M.J. et al., "Use of liposomes as injectable-drug delivery systems" American J. of Hospital Pharmacy, vol. 46, pp. 1576-1587 (2001).
Ottensmeier, C., "The classification of lymphomas and leukemias", Chemic-Biological Interactions, 135-136, pp. 653-664 (2001).
Pack, P. et al., "Improved Bivalent Miniantibodies, with Identical Avidity as Whole Antibodies, Produced by High Cell Density Fermentation of *Escherichia coli*", Bio/Technology, vol. 11, pp. 1271-1277 (1993).
Padlan, E. A., "Review: Anatomy of the Antibody Molecule", Molecular Immunology, vol. 31(3), pp. 169-217 (1994).
Page, B. et al., "A new fluorometric assay for cytotoxicity measurements in vitro", International J. of Oncology, vol. 3, pp. 474-476 (1993).
Petkova, S. et al., "Enhanced half-life of genetically engineered human IgG1 antibodies in a humanized FcRn mouse model: potential application in humorally mediated autoimmune disease", International Immunology, vol. 18(12), pp. 1759-1769 (2006).
Piazza, G. A. et al., "Antineoplastic Drugs Sulindac Sulfide and Sulfone Inhibit Cell Growth by Inducing Apoptosis", Cancer Research, vol. 55, pp. 3110-3116 (1995).
Putney, S.D. "Encapsulation of proteins for improved delivery", Current Opinion in Chemical Biology, vol. 2, pp. 548-552 (1998).
Quidville, V. et al., "Tumor Growth Inhibition by Indomethacin in a Mouse Model of Human Medullary Thyroid Cancer: Implication of Cyclooxygenases and 15-Hydroxyprostaglandin Dehydrogenase", Endocrinology, vol. 145(5), pp. 2561-2571 (2004).
Ren, R., "Dissecting the Molecular Mechanism of Chronic Myelogenous Leukemia Using Murine Models", Leukemia and Lymphoma, vol. 43 (8), pp. 1549-1561 (2002).
Rosenberg, S.A., Immunotherapy and Gene Therapy of Cancer, Cancer Research, (suppl)51, pp. 5074s-5079s, (1991).
Sandhu, Jasbir S., "Protein Engineering of Antibodies", Critical Reviews in Biotechnology, vol. 12(5/6), pp. 437-462 (1992).
Scatchard, G., "The Attractions of Proteins for Small Molecules and Ions", Annals New York Academy of Sciences, vol. 51 pp. 660-672 (1949).
Scherphof, G. et al., "Uptake and Intracellular Processing of Targeted and Nontargeted Liposomes by Rat Kupffer Cells In Vivo and In Vitro", Annals of the New York Academy of Sciences, vol. 446, pp. 368-384 (1985).
Schleinitz, N. et al., "Expression of the CD85j (Leukocyte Ig-like Receptor 1, Ig-like Transcript 2) Receptor for Class I Major Histocompatibility Complex Molecules in Idiopathic Inflammatory Myopathies", Arthritis & Rheumatism, vol. 58(1), pp. 3216-3223 (2008).
Schuurs, A.H.W.M. et al., "Review: Enzyme-Immunoassay", Clinica Chimica Acta, vol. 81, pp. 1-40 (1977).
Scott, I. et al., "Molecular Typing Shows a High level of HLA Class I Incompatibility in Serologically Well Matched Donor/Patient Pairs: Implications for Unrelated Bone Marrow Donor Selection", Blood, vol. 92(12) (1998).
Shih, L.B. et al., "A Fluorouridine-Anti-Cea Immunoconjugate is Therapeutically Effective in a Human Colonic Cancer Xenograft Model", Int. J. Cancer, vol. 46, pp. 1101-1106 (1990).
Shimizu, Y. et al., "Demonstration by class I gene transfer that reduced susceptibility of human cells to natural killer cell-mediated lysis is inversely correlated with HLA class I antigen expression", Eur. J. Immunol., vol. 19, pp. 447-451 (1989).

(56) References Cited

OTHER PUBLICATIONS

Shimizu, K. et al., "Formulation of Liposomes with a Soybean-Derived Sterylglucoside Mixture and Cholesterol for Liver Targeting", Biol. Phar. Bulletin, vol. 20(8), pp. 881-886 (1997).

Singer, I. et al., "Optimal Humanization of 1B4, an Anti-CD18 Murine Monoclonal Antibody, is Achieved by Correct Choice of Human V-Region Framework Sequences", The J. of Immunology, vol. 150 (7), pp. 2844-2857 (1993).

Skehan, P. et al., "New Colorimetric Cytotoxicity Assay for Anticancer-Drug Screening", J. National Cancer Institute, vol. 82(13), pp. 1107-1112 (1990).

Smith, D. et al., "Single-step purification of polypeptides expressed in *Escherichia coli* as fusions with glutathione S-transferase", Gene, vol. 67, pp. 31-40 (1988).

Smyth, Mark J., "Clinical Implications of Basic Research: Imatinib Mesylate-Uncovering a Fast Track to Adaptive Immunity", The New England J. of Medicine, vol. 354(21), pp. 2282-2284 (2006).

Srivastava, B.I.S. et al., "Expression of natural cytotoxicity receptors NKp30, NKp44, and NKp46 mRNAs and proteins by human hematopoietic and non-hematopoietic cells", Leukemia Research, vol. 30, pp. 37-46 (2006).

Stein, R. et al., "Murine Monoclonal Antibodies Raised against Human Non-Small Cell Carcinoma of the Lung: Specificity and Tumor Targeting", Cancer Research, vol. 50, pp. 1330-1336, (1990).

Storkus, W.J., et al., "Reversal of natural killing susceptibility in target cells expressing transfected class I HLA genes" PNAS, vol. 86, pp. 2361-2364 (1989).

Taylor, L. et al., "Human immunoglobulin transgenes undergo rearrangement, somatic mutation and class switching in mice that lack endogenous IgM", International Immunology, vol. 6(4), pp. 579-591 (1994).

Therasse, P. et al., "New Guidelines to Evaluate the Response to Treatment in Solid Tumors", J. of the National Cancer Inst., vol. 92(3), pp. 205-216 (2000).

Thorpe, P. et al., "New Coupling Agents for the Synthesis of Immunotoxins Containing a Hindered Disulfide Bond with Improved Stability in Vivo", Cancer Research, vol. 47, pp. 5924-5931 (1987).

Thorpe, P. et al., "The Preparation and Cytotoxic Properties of Antibody-Toxin Conjugates", Immunological Rev., vol. 62, pp. 119-158 (1982).

Trinchieri, G., "Biology of Natural Killer Cells", Advances in Immunology, vol. 47, pp. 187-376 (1989).

Van Etten, Richard A., "Retroviral Transduction Models of Ph+ Leukemia: Advantages and Limitations for Modeling Human Hematological Malignancies in Mice", Blood Cells, Molecules, and Diseases, vol. 27(1), pp. 201-205 (2001).

Wassef, N. et al., "Complement-Dependent Phagocytosis of Liposomes by Macrophages", Methods in Enzymology, vol. 149, pp. 124-134 (1987).

Wines, B.D. et al., The IgG Fc Contains Distinct Fc Receptor (FcR) Binding Sites: The Leukocyte Receptors FcγRI and FcγRIIa Bind to a Region in the Fc Distinct from That Recognized by Neonatal FcR and Protein A[1] The J. of Immunology, vol. 164, pp. 5313-5318 (2000).

Wong, S. et al., "Modeling Philadelphia chromosome positive leukemias", Oncogene, vol. 20, pp. 5644-5659 (2001).

Woof, J. et al., "Reviews: Human Antibody-FC Receptor Interactions illuminated by Crystal Structures", Nature Reviews/Immunology, vol. 4, pp. 1-11 (2004).

Yamazaki, H. et al., "Changes in natural killer cell activity by external radiotherapy and/pr brachytherapy", Oncology Reports, voo.. 9, pp. 359-363 (2002).

Zhang, J. et al., "qPCR Identification of Genes Involved in Apoptosis and Cell Cycle Regulation", Biochemica, vol. 2, pp. 21-24 (2009).

\* cited by examiner

MONOCLONAL ANTIBODIES THAT BIND B7H6 AND USES THEREOF

CROSS-REFERENCE TO RELATED APPLICATIONS

This application is the National Stage of International Application No. PCT/IB2010/003411, filed 8 Dec. 2010, which claims the benefit of U.S. Provisional Patent Application No. 61/285,018, filed 9 Dec. 2009, the disclosures of which are incorporated herein by reference in their entirety.

TECHNICAL FIELD

The invention relates to antibodies, particularly monoclonal antibodies that bind a tumor cell ligand, designated B7H6. The invention also relates to uses of the antibodies.

BACKGROUND

B7 Family

Positive and negative co-stimulatory signals play critical roles in the modulation of lymphocyte activity, and the molecules that mediate these signals have proven to be effective targets for immunomodulatory agents. For example, upon interaction with B7-1 or B7-2 on the surface of antigen-presenting cells (APC), CD28, the prototypic T cell co-stimulatory molecule, emits signals that promote T cell proliferation and differentiation in response to T cell receptor (TcR) engagement, while the CD28 homologue cytotoxic T lymphocyte antigen-4 (CTLA-4) mediates inhibition of T cell proliferation and effector functions. (See Chambers et al., *Ann. Rev. Immunol.*, 19:565-594, 2001; Egen et al., *Nature Immunol.*, 3:611-618, 2002.)

Several molecules with homology to the B7 family have been discovered (Abbas et al., *Nat. Med.*, 5:1345-6, 1999; Coyle et al., *Nat. Immunol.*, 2: 203-9, 2001; Carreno et al., *Annu. Rev. Immunol.*, 20: 29-53, 2002; Liang et al., *Curr. Opin. Immunol.*, 14: 384-90, 2002), and their role in lymphocyte activation is just beginning to be elucidated. These new co-stimulatory counter-receptors include B7h2, PD-L1, PD-L2, B7-H3 and B7-H4.

The expression of known B7 family members is largely restricted to antigen-presenting cells. Studies have revealed that B7 family members are counter-receptors on lymphoid cells that interact with cognate receptors on lymphocytes to provide positive or negative co-stimulatory signals that play critical roles in the regulation of cell-mediated immune responses.

NK Cells and NKp30

Natural killer (NK) cells are a subset of lymphocytes active in the immune system and represent an average of about 15% of mononuclear cells in human peripheral blood. NK cells were initially described functionally in 1971 by the observation that lethally irradiated mice were capable of rejecting allogeneic or parental strain bone marrow cell (BMC) allografts. (See Cudowicz and Bennett, *J. Exp. Med.* 134:83-102, 1971; Cudowicz and Bennett, *J. Exp. Med.* 135:1513-1528, 1971.) Cudowicz and Bennett observed that irradiated F1 hybrid H-2-heterozygous mice (A×B) were capable of rejecting parental H-2-homozygous BMC (A or B). This observation conflicted with the classic laws of transplantation in which transplantation antigens were thought to inherit co-dominantly and offspring were obligately tolerant toward parental major histocompatability complex (MHC) determinants (See Cudowicz and Bennett, *J. Exp. Med.* 134:83-102, 1971.) The cells responsible for this phenomenon were found to be radioresistant and identical to lymphoid cells, which were characterized later in 1975 by their ability to mediate spontaneous killing of tumors in vitro in an MHC-unrestricted manner (See Herberman and Ortaldo, *Science,* 214: 24-30, 1981; Ortaldo and Herberman, *Annu. Rev. Immunol.* 2:359-394, 1984; Trinchieri, *Adv. Immunol.* 47:187-376, 1989; Murphy et al., *J. Natl. Cancer Inst.* 85:1475-1482, 1993.) Additional evidence that NK cells alone could mediate the specificity of marrow graft rejection emerged in 1987 when it was observed that mice with severe combined immune deficiency (SCID), which cannot develop T and B cells, have normal NK cell function. (See Murphy et al., *J. Exp. Med.* 165:1212-1217, 1987.)

NK cells are currently understood to represent an important arm of innate immunity and to play a primary role in immune surveillance against tumors and virally infected cells. Unless activated, however, NK cells are ineffective in performing their normal function, even when present in otherwise sufficient numbers. Indeed, decreased NK cell activity is associated with cancer and infectious diseases (see Yamazaki et al., *Oncology Reports* 9:359-363, 2002; Rosenberg et al., *Cancer Research* 51:5074-5079 (suppl.), 1991; Britteenden et al., *Cancer* 77:1226-1243, 1996; U.S. Pat. Nos. 5,082,833 and 4,883,662). Conversely, as noted above, NK cell activity mediates acute rejection of BMC allografts. Therefore, levels of NK cell activity appear to play an important role in immune-related disorders.

NK cell activity is typically regulated by the interaction between MHC class I molecules and inhibitory and activating receptors. (See, e.g., Barao and Murphy, *BB&MT* 9:727-741, 2003.) The "missing self" hypothesis is originally based on the observation that tumor cells that lack MHC class I molecules are susceptible to killing by NK cells. (See Ljunggren and Kane, *Immunol. Today* 11:237-244, 1990; Ohlen et al., *J. Immunol.* 145:52-58, 1990.) Investigators additionally observed that human NK cells lyse class-I-deficient Epstein-Barr-virus-transformed B-lymphoblastoid cell lines. (Storkus et al., *Proc. Natl. Acad. Sci. USA* 86:2361-2364, 1989.) Also, it was found that transfection of class I genes into class I-deficient target cells caused these cells to be partially or completely resistant to NK cell-mediated lysis. (See Storkus et al., supra; Shimizu and DeMars, *Eur. J. Immunol.,* 19:447-451, 1989.) MHC class I, however, is not always necessary for protection from NK-cell-mediated cytotoxicity, and recognition by MHC class I does not always prevent cytolysis by NK cells. (Barao and Murphy, supra.) During recent years, various MHC-class-I-specific inhibitory and activating receptors as well as non-MHC-class-I-specific activating receptors have been identified. These receptors are relevant with respect to therapeutic approaches such as, e.g., allogeneic BMT and cancer therapy. (See id.)

Non-MHC-class-I-specific activating receptors, which are capable of mediating NK cell cytotoxicity against MHC-class-I-deficient or negative targets, are represented in part by a heterogeneous family of NK cell-specific immunoglobulin-like molecules that are known as natural cytotoxicity receptors (NCRs). (See, e.g., Moretta et al., *Annu. Rev. Immunol.* 19:197-223, 2001; Diefenbach and Raulet, *Immunol. Rev.,* 181:170-184, 2001.) In the absence of MHC class I expression (such as, for example, on tumor cells or virus-infected cells), ligation of these activating receptors on NK cells triggers target-cell killing. One such activating receptor is NKp30, which is selectively and constitutively expressed on mature natural killer (NK) cells and signals through, inter alia, coupling with CD3ζ. (See Barao and Murphy, supra.) The target-cell ligand to which NKp30 binds has not been previously identified.

This system of innate recognition by NK cells represents a potentially powerful tool for clinical application in allogeneic bone marrow transplantation (BMT), cancer therapy, or treatment of other NK-cell-associated disorders. (See, e.g., Barao and Murphy, supra.) For example, stimulating or inhibiting activation of NKp30 would be useful for modulating NK cell activity and treating diseases or disorders associated with NK cell activity. In particular, enhancement of NK cell activity by triggering NKp30 would be useful for treatment of diseases or disorders characterized by insufficient NK cell activity, such as cancer and infectious disease, while inhibition of NK cell activity by blocking NKp30 would be useful for treating NK-cell-mediated disorders, such as, for example, BMC allograft rejection.

The newest member of the B7 family, B7H6, was recently discovered and characterized as a counter-receptor for NKp30, a receptor selectively expressed on mature natural killer (NK) cells and which is involved in human natural cytotoxicity as an activatory receptor (Brandt et al., *J. Exp. Med.*, 206(7): 1495-1503, 2009). B7H6 was not detected in normal human tissues, but was expressed on human tumor cells.

Accordingly, there is a need in the art for the identification of antibodies capable of inhibiting the interaction of B7H6 with NKp30. There is a therapeutic potential for such antibodies based their ability to modulate co-stimulatory signals and immune responses. Furthermore, antibodies that bind to B7H6 proteins will be useful when conjugated to a cytotoxic agent and used to target a cell expressing B7H6. These and other uses are highly desirable. The present invention provides compositions and methods for these and other uses that should be apparent to those skilled in the art from the teachings herein.

BRIEF SUMMARY OF THE INVENTION

An aspect of the present invention provides isolated, monoclonal antibodies that specifically bind to the extracellular domain of human B7H6 (amino acid residues 25-266 of SEQ ID NO:2). In one embodiment, the antibody competes for binding to the extracellular domain of human B7H6 (amino acid residues 25-266 of SEQ ID NO:2) with an antibody produced by hybridoma of clone designation 4E5.5 (Deposit No. CNCM I-4242). In another embodiment, the antibody competes for binding to the extracellular domain of human B7H6 (amino acid residues 25-266 of SEQ ID NO:2) with an antibody produced by hybridoma of clone designation 9G9.2 (Deposit No. CNCM I-4243). In another embodiment, the antibody competes for binding to the extracellular domain of human B7H6 (amino acid residues 25-266 of SEQ ID NO:2) with an antibody produced by hybridoma of clone designation 10E2.9 (Deposit No. CNCM I-4244). In another embodiment, the antibody competes for binding to the extracellular domain of human B7H6 (amino acid residues 25-266 of SEQ ID NO:2) with an antibody produced by hybridoma of clone designation 17B1.3 (Deposit No. CNCM I-4245).

In certain embodiments, the anti-B7H6 monoclonal antibody described above is a murine antibody, a chimeric antibody, a humanized antibody, or a human antibody. In some embodiments, the antibody will compete for binding to the human B7H6 extracellular domain and inhibit the interaction of human B7H6 with NKp30. The inhibition may be completely or partially blocking, and may neutralize or reduce the interaction. Suitable antibodies further include single chain antibodies. Other variations embodied include antibodies comprising an Fc region having at least one of ADCC activity and CDC activity. In some such variations, the Fc region is a single chain Fc (scFc). Each of the embodied monoclonal antibodies that bind human B7H6 is suitable as a composition comprising the antibody and pharmaceutically acceptable vehicle. Such antibodies are suitable for diagnostic kits that detect binding by the antibody.

In another aspect, the present invention provides an antibody-drug conjugate comprising a monoclonal antibody that specifically binds to the extracellular domain of human B7H6 (amino acid residues 25-266 SEQ ID NO:2), where the antibody is conjugated to a cytotoxic agent. In some embodiments, the antibody portion of the antibody-drug conjugate is an antibody that competes for binding to the extracellular domain of human B7H6 (amino acid residues 25-266 of SEQ ID NO:2) with an antibody produced by hybridoma of clone designation 4E5.5 (Deposit No. CNCM I-4242); an antibody produced by hybridoma of clone designation 9G9.2 (Deposit No. CNCM I-4243); an antibody produced by hybridoma of clone designation 10E2.9 (Deposit No. CNCM I-4244); or an antibody produced by hybridoma of clone designation 17B1.3 (Deposit No. CNCM I-4245). The monoclonal antibody can be, for example, a murine antibody, a chimeric antibody, a humanized antibody, or a human antibody. Suitable antibodies further include single chain antibodies. In certain variations, the antibody comprises an Fc region having at least one of ADCC activity and CDC activity. In some such variations, the Fc region is a single chain Fc (scFc). The cytotoxic agent can be, e.g., an anti-tubulin agent, a DNA minor groove binding agent, a DNA minor groove alkylating agent, a duocarmycin, or a puromycin. Suitable anti-tubulin agents include, for example, dolastatin, a vinc alkaloid, a podophyllatoxin, a taxane, a baccatin derivative, a cryptophysin, a maytansinoid, or a combretastatin. In certain embodiments, the antibody is conjugated to the drug via a linker, and in some cases the linker is cleavable under intracellular conditions. Suitable cleavable linkers include peptide linkers, including those cleavable by an intracellular protease. Any of the embodied antibody-drug conjugates are suitable as compositions comprising the antibody-drug conjugate and pharmaceutically acceptable vehicle.

In another related aspect, the present invention provides methods for decreasing natural killer (NK) cell activity against a cell expressing human B7H6 by inhibiting the interaction of human B7H6 with human NKp30. Such methods generally include contacting a cell expressing human B7H6, in the presence of a human NK cell, with an effective amount of a monoclonal antibody that competes for binding to the extracellular domain of human B7H6 with an antibody produced by hybridoma of clone designation 4E5.5 (Deposit No. CNCM I-4242) or an antibody produced by hybridoma of clone designation 17B1.3 (Deposit No. CNCM I-4245), wherein the antibody inhibits the interaction of human B7H6 with human NKp30.

In another related aspect, the present invention provides methods for treating bone marrow cell (BMC) allograft rejection in a subject by inhibiting the interaction of human B7H6 with human NKp30. Such methods generally include administering to the subject, in an amount effective to inhibit NK cell activity and thereby treat the acute BMC allograft rejection, a monoclonal antibody that competes for binding to the extracellular domain of human B7H6 with an antibody produced by hybridoma of clone designation 4E5.5 (Deposit No. CNCM I-4242) or an antibody produced by hybridoma of clone designation 17B1.3 (Deposit No. CNCM I-4245), where the antibody inhibits the interaction of human B7H6 with human NKp30.

Both the method for decreasing human NK cell activity and the method for treating BMC allograft rejection include certain embodiments where the antibodies are human or humanized monoclonal antibodies. The methods also include embodiments where the antibody is a single chain antibody.

In other related aspects, the present invention provides methods for depleting or inhibiting the growth of B7H6-expressing cells within a cell population using an antibody-drug conjugate. The methods generally comprise contacting the B7H6-expressing cells with an effective amount of an antibody-drug conjugate comprising (a) an antibody that competes for binding to the extracellular domain of human B7H6 competes (amino acid residues 25-266 of SEQ ID NO:2) with an antibody produced by hybridoma of clone designation 4E5.5 (Deposit No. CNCM I-4242); an antibody produced by hybridoma of clone designation 9G9.2 (Deposit No. CNCM I-4243); an antibody produced by hybridoma of clone designation 10E2.9 (Deposit No. CNCM I-4244); or an antibody produced by hybridoma of clone designation 17B1.3 (Deposit No. CNCM I-4245); and (b) a cytotoxic agent conjugated to the antibody.

Another related aspect provides methods for treating a B7H6-expressing cancer in a subject using an antibody-drug conjugate. The methods generally comprise administering to the subject an effective amount of an antibody-drug conjugate comprising (a) an antibody that competes for binding to the extracellular domain of human B7H6 competes (amino acid residues 25-266 of SEQ ID NO:2) with an antibody produced by hybridoma of clone designation 4E5.5 (Deposit No. CNCM I-4242); an antibody produced by hybridoma of clone designation 9G9.2 (Deposit No. CNCM I-4243); an antibody produced by hybridoma of clone designation 10E2.9 (Deposit No. CNCM I-4244); or an antibody produced by hybridoma of clone designation 17B1.3 (Deposit No. CNCM I-4245); and (b) a cytotoxic agent conjugated to the antibody. Included are embodiments where the cancer is a cancer of the colon, liver, cervix, lung, pancreas or prostate. Other suitable B7H6-expressing cancers for treatment include prohemocytic leukemia, B-cell lymphoma, monocytic lymphoma, erythroleukemia, Burkitt's lymphoma and chronic myelogenous leukemia.

In both a method for depleting or inhibiting the growth of B7H6-expressing cells within a cell population and/or a method of treating a B7H6-expressing cancer in a subject, human or humanized monoclonal antibodies are suitable for the antibody comprising the antibody-drug conjugate. It is also suitable to use a single chain antibody for the antibody comprising the antibody-drug conjugate for both of these methods.

In other related aspects, methods for inducing antibody dependent cellular cytotoxicity (ADCC) against a B7H6-expressing cell are provided. These methods generally include contacting the B7H6-expressing cell with an effective amount of an antibody that competes for binding to the extracellular domain of human B7H6 (amino acid residues 25-266 of SEQ ID NO:2) with an antibody produced by hybridoma of clone designation 4E5.5 (Deposit No. CNCM I-4242); an antibody produced by hybridoma of clone designation 9G9.2 (Deposit No. CNCM I-4243); an antibody produced by hybridoma of clone designation 10E2.9 (Deposit No. CNCM I-4244); or an antibody produced by hybridoma of clone designation 17B1.3 (Deposit No. CNCM I-4245); where the contacting is in the presence of an NK or a CD8+ T cell expressing an Fc receptor having ADCC activity, and the antibody comprises an Fc region capable of binding the Fc region.

In other related aspects, methods for inducing complement dependent cytotoxicity (CDC) against a B7H6-expressing cell are provided. These methods generally include contacting the B7H6-expressing cell with an effective amount of an antibody that competes for binding to the extracellular domain of human B7H6 (amino acid residues 25-266 of SEQ ID NO:2) with an antibody produced by hybridoma of clone designation 4E5.5 (Deposit No. CNCM I-4242); an antibody produced by hybridoma of clone designation 9G9.2 (Deposit No. CNCM I-4243); an antibody produced by hybridoma of clone designation 10E2.9 (Deposit No. CNCM I-4244); or an antibody produced by hybridoma of clone designation 17B1.3 (Deposit No. CNCM I-4245); where the contacting is in the presence of complement, and the antibody comprises an Fc region having CDC activity.

In both methods for inducing ADCC against a B7H6-expressing cell and/or inducing CDC against a B7H6-expressing cell, embodiments include human or humanized antibodies. Also included are single chain antibodies. Another variation includes Fc regions where the Fc region is a single chain Fc (scFc). For either method, in some embodiments, the B7H6-expressing cancer is a cancer cell. The cancer cell can be, for example, a colon cancer cell, a liver cancer cell, a cervical cancer cell, a lung cancer cell, pancreatic cancer cell, a prostate cancer cell, a prohemocytic leukemia cell, a B-cell lymphoma cell, a monocytic lymphoma cell, an erythroleukemia cell, a Burkitt's lymphoma cell, or a chronic myelogenous leukemia cell.

Another related aspect provides methods for treating a B7H6-expressing cancer. The method generally comprises administering to a subject an effective amount of a monoclonal antibody that competes for binding to the extracellular domain of human B7H6 (amino acid residues 25-266 of SEQ ID NO:2) with an antibody produced by hybridoma of clone designation 4E5.5 (Deposit No. CNCM I-4242); an antibody produced by hybridoma of clone designation 9G9.2 (Deposit No. CNCM I-4243); an antibody produced by hybridoma of clone designation 10E2.9 (Deposit No. CNCM I-4244); or an antibody produced by hybridoma of clone designation 17B1.3 (Deposit No. CNCM I-4245); where the antibody comprises an Fc region having at least one of ADCC activity and CDC activity. Suitable monoclonal antibodies include human antibodies, humanized antibodies, and single chain antibodies. In certain variations, the Fc region is a single chain Fc (scFc). B7H6-expressing cancers amenable to treatment include, for example, cancers of the colon, liver, cervix, lung, pancreas or prostate. Other suitable B7H6-expressing cancers include, e.g., prohemocytic leukemia, B-cell lymphoma, monocytic lymphoma, erythroleukemia, Burkitt's lymphoma, and chronic myelogenous leukemia.

Another related aspect provides methods of detecting cellular expression B7H6 where binding of the antibody indicates presence of B7H6 on a cell. Generally the method comprises (1) contacting a biological sample comprising a human cell to be tested with a monoclonal antibody that competes for binding to the extracellular domain of human B7H6 (amino acid residues 25-266 of SEQ ID NO:2) with an antibody produced by hybridoma of clone designation 4E5.5 (Deposit No. CNCM I-4242); an antibody produced by hybridoma of clone designation 9G9.2 (Deposit No. CNCM I-4243); an antibody produced by hybridoma of clone designation 10E2.9 (Deposit No. CNCM I-4244); or an antibody produced by hybridoma of clone designation 17B1.3 (Deposit No. CNCM I-4245); and (2) detecting binding of the antibody, where the binding indicates the presence of B7H6 on the cell and detects whether the cell expresses B7H6. In some embodiments, the biological samples are intact human cells or a membrane fraction of the cell to be tested. In certain embodiments, the antibody is labeled with a detectable label.

Suitable labels include radioisotopes, fluorescent labels, chemiluminescent labels, enzyme labels or bioluminescent labels.

In a related aspect, the present invention provides methods for diagnosing a subject suspected of having a cancer expressing B7H6. The method generally includes (1) administering to the subject a monoclonal antibody that competes for binding to the extracellular domain of human B7H6 (amino acid residues 25-266 of SEQ ID NO:2) with an antibody produced by hybridoma of clone designation 4E5.5 (Deposit No. CNCM I-4242); an antibody produced by hybridoma of clone designation 9G9.2 (Deposit No. CNCM I-4243); an antibody produced by hybridoma of clone designation 10E2.9 (Deposit No. CNCM I-4244); or an antibody produced by hybridoma of clone designation 17B1.3 (Deposit No. CNCM I-4245) conjugated to a detectable label; and (2) detecting distribution of the antibody within the subject. Suitable applications include the diagnosis of cancers of the colon, liver, cervix, lung, pancreas or prostate.

In another aspect, the present invention also provides antibody-producing cell selected from the group consisting of a hybridoma of clone designation 4E5.5 (Deposit No. CNCM I-4242); a hybridoma of clone designation 9G9.2 (Deposit No. CNCM I-4243); a hybridoma of clone designation 10E2.9 (Deposit No. CNCM I-4244); or a hybridoma of clone designation 17B1.3 (Deposit No. CNCM I-4245).

DETAILED DESCRIPTION OF THE INVENTION

I. Overview

The present invention relates to the identification and characterization of anti-B7H6 antibodies which bind to a member of the B7 family of cell surface proteins, particularly anti-human B7H6 monoclonal antibodies.

B7H6 polypeptide was first identified as a counter-receptor for NKp30, a receptor selectively expressed on mature natural killer (NK) cells and is involved in human natural cytotoxicity as an activatory receptor (see US Patent Application Publication No. 2009/0220502), incorporated herein by reference in its entirety. An illustrative nucleotide sequence that encodes human B7H6 is provided by SEQ ID NO:1; the encoded polypeptide is shown in SEQ ID NO:2. The B7H6 polypeptide of SEQ ID NO:2 comprises an extracellular domain of approximately 242 amino acid residues (residues 25-266 of SEQ ID NO:2), a transmembrane domain of approximately 18 amino acid residues (residues 267-284 of SEQ ID NO:2), and an intracellular domain of approximately 158 amino acid residues (residues 285-454 of SEQ ID NO:2). B7H6 also has an IgV domain of approximately 117 amino acid residues (residues 25-141 of SEQ ID NO:2) and an IgC domain of approximately 97 amino acid residues (residues 142-238 of SEQ ID NO:2). There are also several potential signaling motifs within the intracellular domain of B7H6, including an ITIM motif (SaYtpL, amino acid residues 293-298 of SEQ ID NO:2); an SH2 binding motif (YqlQ, amino acid residues 229-332 of SEQ ID NO:2); and an SH3 binding motif (PdaPilPvsP, amino acid residues 418-427 of SEQ ID NO:2).

The present invention arises from the production of murine monoclonal antibodies against the human B7H6 protein and characterization of the properties of those antibodies. Five mouse monoclonal antibodies against human B7H6 with the isotype IgG1 were produced from hybridomas. The antibodies have been designated 4E5.5, 5E1.4, 9G9.2, 10E2.9 and 17B1.3. Competition assays revealed that different epitopes were recognized by certain antibodies. Two of anti-B7H6 mAbs, 17B1.3 and 4E5.5, partially block the NKp30:B7H6 interaction, as shown by the inhibition of NKp30Fc binding and DOMSP30 activation. These studies correlate structure to function and are described in the Examples. The various monoclonal antibodies are shown to be useful reagents in biochemical and diagnostic assays as well as having therapeutic value.

Thus, the present invention includes monoclonal antibodies that bind a human B7H6 cell surface protein with the same or similar specificity and characteristics as mAbs 4E5.5, 5E1.4, 9G9.2, 10E2.9 and/or 17B1.3. As described herein, mouse anti-human-B7H6 monoclonal antibodies were produced and shown to bind to different epitopes in competition experiments. Therefore, one aspect of the present invention provides antibodies that are capable of competing with these antibodies for binding to B7H6 (e.g., an antibody that is capable of binding the same B7H6 epitope as an antibody selected from mAbs 4E5.5, 9G9.2, 10E2.9, and 17B1.3). Furthermore, some of the antibodies were shown to effect the B7H6-NKp30 interaction. Accordingly, in some embodiments, anti-human-B7H6 monoclonal antibodies of the present invention inhibit B7H6-mediated activation of NKp30.

The present invention further provides for humanized antibodies derived from non-human anti-B7H6 antibodies (e.g., humanized antibodies derived from murine antibodies), neutralizing antibodies, human monoclonal antibodies, and antigen-binding fragments thereof. Illustrative antibody fragments include F(ab')$_2$, F(ab)$_2$, Fab', Fab, Fv, scFv, and minimal recognition units. Neutralizing antibodies bind B7H6 such that its interaction with NKp30 is inhibited or blocked. Within the scope of the invention is a monoclonal antibody that competes for binding to the extracellular domain of human B7H6 for use to inhibit NK cell-mediated responses such as, for example, in acute bone marrow cell (BMC) allograft rejection, where the antibody is administered in an effective amount to block NK cell activity and treat BMC allograft rejection.

Anti-B7H6 antibodies in accordance with the present invention can also be used to target cytotoxic agents to a B7H6-expressing cell, particularly a B7H6-expressing cancer cell. Such anti-human-B7H6 monoclonal antibody-drug conjugates produce clinically beneficial effects on B7H6-expressing cells when administered to a subject, such as a subject with a B7H6-expressing cancer. The antibody is generally administered alone, but can be administered in combination with other therapeutic agents. In typical embodiments, an anti-human-B7H6 monoclonal antibody is conjugated to a cytotoxic agent, such that the resulting antibody-drug conjugate exerts a cytotoxic or cytostatic effect on a B7H6-expressing cell (e.g., a B7H6-expressing cancer cell) when taken up or internalized by the cell.

Thus, in some aspects, the present invention includes anti-human-B7H6 monoclonal antibody-drug conjugates. The antibody portion will bind a human B7H6 cell surface protein with the same or similar specificity and characteristics described herein, and the drug conjugate portion will be a therapeutic agent. The anti-human-B7H6 antibody-drug conjugate will exert a clinically beneficial effect on B7H6-expressing cells when administered to a subject with a B7H6-expressing cancer. Typically the drug conjugate portion will be a cytotoxic agent and will exert a cytotoxic or cytostatic effect on a B7H6-expressing cell. For these antibodies-drug conjugates, the antibody portion will recognize certain epitopes on B7H6. In certain variations, an anti-human-B7H6 monoclonal antibody-drug conjugate affects the B7H6-NKp30 interaction. For example, in some embodiments, an anti-human-B7H6 monoclonal antibody-drug conjugate in accordance with the present invention inhibits activation of NKp30.

In other embodiments, an anti-human-B7H6 monoclonal antibody comprises an Fc region with effector function used to induce antibody dependent cellular cytotoxicity (ADCC) or complement dependent cytotoxicity (CDC) against a B7H6-expressing cell. The present invention includes an anti-human-B7H6 monoclonal antibody comprising an Fc region having ADCC activity for use in inducing ADCC. For this use, generally a B7H6-expressing cell is contacted with an effective amount of the anti-human-B7H6 monoclonal antibody comprising an Fc region and in the presence of a cytolytic immune effector cell expressing an Fc receptor having cytolytic activity. Immune effector cells expressing cytolytic Fc receptors (e.g., FcγRIIIα or CD16) include, for example, NK cells as well as certain CD8+ T cells. In embodiments where an anti-human-B7H6 monoclonal antibody comprising an Fc region having CDC activity is for use in inducing CDC, generally the B7H6-expressing cell is contacted with an effective amount of the anti-human-B7H6 monoclonal antibody comprising an Fc region having CDC activity, and is in the presence of complement. B7H6-expressing cells that can be targeted for killing using the antibodies and methods claimed herein include, for example, cancer cells, such as, e.g., colon cancer cells, liver cancer cells, cervical cancer cells, lung cancer cells, pancreatic cancer cells, prostate cancer cells, prohemocytic leukemia cells, B-cell lymphoma cells, monocytic lymphoma cells, erythroleukemia cells, Burkitt's lymphoma cells, and chronic myelogenous leukemia cells, to name a few.

These and other aspects of the invention will become evident upon reference to the following detailed description. In addition, various references are identified below and are incorporated by reference in their entirety.

II. Definitions

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" as used herein include plural referents, unless the context clearly indicates otherwise.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, such as 96%, 97%, or 98% or more pure, or greater than 99% pure.

One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

As used herein, the term "immunomodulator" includes cytokines, stem cell growth factors, lymphotoxins, co-stimulatory molecules, hematopoietic factors, and the like, and synthetic analogs of these molecules.

The term "antibody," as used herein, refers to immunoglobulin polypeptides and immunologically active portions of immunoglobulin polypeptides, i.e., polypeptides of the immunoglobulin family, or fragments thereof, that contain an antigen binding site that immunospecifically binds to a specific antigen (e.g., the extracellular domain of B7H6).

An "anti-idiotype antibody" is an antibody that binds with the variable region domain of an immunoglobulin. In the present context, an anti-idiotype antibody binds with the variable region of an anti-human-B7H6 monoclonal antibody, and thus, an anti-idiotype antibody mimics an epitope of B7H6.

An "antibody fragment" is a portion of an antibody such as F(ab')$_2$, F(ab)$_2$, Fab', Fab, and the like. Regardless of structure, an antibody fragment binds with the same antigen that is recognized by the intact antibody. For example, an anti-B7H6 monoclonal antibody fragment binds to an epitope of B7H6.

The term "antibody" also encompasses genetically engineered intact antibodies or fragments such as, for example, chimeric antibodies, humanized antibodies, "Fv" fragments consisting of the variable regions of the heavy and light chains, polypeptides consisting of the light chain variable region, recombinant single chain antibodies in which light and heavy variable regions are connected by a peptide linker ("scFv proteins"), minimal recognition units consisting of the amino acid residues that mimic the hypervariable region, and the like, as well as synthetic antigen-binding peptides and polypeptides.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which non-human (e.g., murine) complementarity determining regions of a monoclonal antibody have been transferred from heavy and light variable chains of the non-human immunoglobulin into a human variable domain. Construction of humanized antibodies for therapeutic use in humans that are derived from non-human (e.g., murine) antibodies, such as those that bind to or neutralize a human protein, is within the skill of one in the art.

The terms "Fc fragment," "Fc region," or "Fc domain," as used herein, are synonymous and refer to the portion of an antibody that is responsible for binding to antibody receptors on cells and the C1q component of complement. Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc fragment consists of the disulfide-linked heavy chain hinge regions, $C_H2$, and $C_H3$ domains. However, more recently the term has been applied to a single chain consisting of $C_H3$, $C_H2$, and at least a portion of the hinge sufficient to form a disulfide-linked dimer with a second such chain. For a review of immunoglobulin structure and function, see Putnam, *The Plasma Proteins*, Vol. V (Academic Press, Inc., 1987), pp. 49-140; and Padlan, *Mol. Immunol.* 31:169-217, 1994. As used herein, the term Fc includes variants of naturally occurring sequences.

The terms "single chain Fc," "single chain Fc domain," and "scFc," as used herein, are synonymous and refer to a polypeptide fusion comprising two Fc domain monomers joined by a flexible linker, such that the two Fc monomers are capable of dimerization to form a functional, dimeric Fc domain capable of binding Fc receptors. Single chain Fc polypeptides are further described in International PCT Patent Application Publication No. WO 08/0131242, entitled "Single Chain Fc, Methods of Making, and Methods of Treatment," the disclosure of which is incorporated by reference herein in its entirety.

The term "Fc region having ADCC activity," as used herein, refers to an Fc domain capable of mediating antibody dependent cellular cytotoxicity (ADCC) through binding of a cytolytic Fc receptor (e.g., FcγRIIIα) on a cytolytic immune effector cell expressing the Fc receptor (e.g., an NK cell or $CD8^+$ T cell).

The term "complement" refers collectively to those components in normal serum that, together with antigen-bound antibodies, exhibit the ability to lyse cells. Complement consists of a group of serum proteins that act in concert and in an orderly sequence to exert their effect.

The terms "classical complement pathway" and "classical complement system," as used herein, are synonymous and refer to a particular pathway for the activation of complement. The classical pathway requires antigen-antibody complexes for initiation and involves the activation, in an orderly fashion, of nine major protein components designated C1 through C9. For several steps in the activation process, the product is an enzyme that catalyzes the subsequent step. This cascade provides amplification and activation of large amounts of complement by a relatively small initial signal.

The term "Fc region having CDC activity," as used herein, refers to an Fc domain capable of mediating complement dependent cytotoxicity (CDC) through binding of C1q complement protein and activation of the classical complement system.

The term "agent" as used herein means an element, compound, or other molecular entity, including, e.g., a pharmaceutical, therapeutic, or pharmacologic compound. Agents can be natural or synthetic or a combination thereof. A "therapeutic agent" is an agent that exerts a therapeutic (e.g., beneficial) effect on a cell or a tissue (e.g., on a cell or tissue expressing B7H6, such as a B7H6-expressing cancer cell), either alone or in combination with another agent (e.g., a prodrug converting enzyme in combination with a prodrug). In certain aspects of the present invention, a "therapeutic agent" is an agent conjugated to an antibody to produce a conjugate that is useful for therapy. Examples of therapeutic agents include drugs, toxins, immunomodulators, chelators, boron compounds, photoactive agents or dyes, and radioisotopes. In some variations, a therapeutic agent for conjugation to an antibody is an agent that exerts a cytotoxic or cytostatic effect.

"Cytotoxic effect," in reference to the effect of an agent on a cell, means killing of the cell. "Cytostatic effect" means an inhibition of cell proliferation. A "cytotoxic agent" means an agent that has a cytotoxic or cytostatic effect on a cell, thereby depleting or inhibiting the growth of, respectively, cells within a cell population.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952, 1985), substance P, FLAG peptide (Hopp et al., *Biotechnology* 6:1204, 1988), streptavidin binding peptide, or other antigenic epitope or binding domain. See generally Ford et al., *Protein Expression and Purification* 2:95, 1991. DNA molecules encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

The term "monoclonal antibody" refers to an antibody that is derived from a single cell clone, including any eukaryotic or prokaryotic cell clone, or a phage clone, and not the method by which it is produced. Thus, the term "monoclonal antibody" as used herein is not limited to antibodies produced through hybridoma technology.

An "immunoconjugate" is a conjugate of an antibody with a therapeutic agent or a detectable label.

The term "epitope" refers to any protein determinant capable of specific binding to a immunoglobin or T-cell receptor. Epitopic determinants usually consist of chemically active surface groupings of molecules such as amino acids or sugar side chains and usually have specific three dimensional structural characteristics, as well as specific charge characteristics. More specifically, the term "B7H6 epitope" as used herein refer to a portion of the B7H6 polypeptide having antigenic or immunogenic activity in an animal, preferably a mammal, and most preferably a mouse or human. An epitope having immunogenic activity is a portion of a B7H6 polypeptide that elicits an antibody response in an animal. An epitope having antigenic activity is a portion of a B7H6 polypeptide to which an antibody immunospecifically binds as determined by any method well known in the art, for example, by immunoassays. Antigenic epitopes need not necessarily be immunogenic. "Discontinuous epitopes" are conformational epitopes formed from at least two separate regions in the primary sequence of the B7H6 protein. Conformational epitopes lose the ability to specifically bind in the presence of denaturing solvents (e.g. in Western blot analyses).

"NK cell activity" as used herein refers to NK cell cytolytic activity. There are numerous assays well-known to the skilled artisan for detecting and/or monitoring such activity, including but not limited to the assays described in the examples provided herein.

As used herein, the phrase "interaction of B7H6 and NKp30" refers to direct physical interaction (e.g., binding) and/or other indirect interaction of a functional B7H6 receptor with NKp30 on an NK cell, resulting in stimulation of the B7H6 receptor and/or NKp30 and associated intracellular signaling.

As used herein, the term "blocking antibody" refers to an antibody that interferes with (i.e., inhibits) the interaction of B7H6 and NKp30, and/or that interferes with the ability of the B7H6 to trigger NK cell activity, e.g., as measured by cytolytic activity Inhibition does not have to be complete and may be "partial", i.e., a decrease or reduction in activity as a relative measurement to a control or standard.

The phrase "disease or disorder characterized by the presence of B7H6-expressing cells," as used herein, refers to any disease or disorder that involves, at least in part, pathogenic cells expressing B7H6. Such pathogenic cells include, for example, certain tumor cells. Accordingly, typical diseases or disorders characterized by the presence of B7H6-expressing cells are certain cancers. Such diseases and disorders are particularly amenable to certain treatment methods for targeting B7H6-expressing cells, as described further herein.

The terms "disease or disorder mediated by NKp30-expressing cells" and "disease or disorder associated with increased activity of an NKp30-expressing cell" are used synonymously herein to refer to any disease or disorder having a pathology that is mediated, at least in part, by cytolytic activity of an NKp30-expressing cell. In some variations, the NKp30-expressing-cell-mediated disease or disorder is an "NK cell-mediated disease or disorder," having a pathology that is mediated, at least in part, by NK cell cytolytic activity. An example of such a disease or disorder is acute rejection of bone marrow cell (BMC) allografts. Such diseases or disorder are particularly amenable to certain treatment methods for inhibition NK cell activity, as described further herein.

The term "effective amount," in the context of treatment of a disease or disorder mediated by NKp30-expressing cells by administration of a blocking anti-B7H6 antibody to a subject as described herein, or in the context of treatment of a disease or disorder characterized by the presence of B7H6 expressing cells by administration of an anti-B7H6 antibody or antibody-drug conjugate to a subject as described herein, refers to the amount of such molecule that is sufficient to inhibit the occurrence or ameliorate one or more clinical or diagnostic symptoms of the disease or disorder in a subject. An effective amount of an agent is administered according to the methods of the present invention in an "effective regime." The term "effective regime" refers to a combination of amount of the agent being administered and dosage frequency adequate to accomplish treatment or prevention of the disease or disorder.

Due to the imprecision of standard analytical methods, molecular weights and lengths of polymers are understood to be approximate values. When such a value is expressed as "about" X or "approximately" X, the stated value of X will be understood to be accurate to ±10%.

III. Antibodies to B7H6 Proteins

In one aspect, the present invention provides anti-human-B7H6 monoclonal antibodies that specifically bind to an epitope of human B7H6 (e.g., to a polypeptide segment from the amino acid sequence set forth in residues 25-266 of SEQ ID NO:2). In some variations, the anti-human B7H6 monoclonal antibodies provided are capable of inhibiting the B7H6-NKp30 interaction Inhibition does not have to be complete blocking of the B7H6-NKp30 interaction, and may be a decrease or reduction in activity as a relative measurement to a control or standard. In certain embodiments, a monoclonal anti-human B7H6 antibody in accordance with the present invention is capable of competing for binding to human B7H6 antigen with an antibody produced by a hybridoma selected from 4E5.5 (Deposit No. CNCM I-4242), 9G9.2 (Deposit No. CNCM I-4243), 10E2.9 (Deposit No. CNCM I-4244), or 17B1.3 (Deposit No. CNCM I-4245). These four hybridomas were deposited at the Collection Nationale de Cultures de Microorganismes (CNCM, Institut Pasteur; Paris, France) on 18 Nov. 2009, in the name of Institut National De La Santé et De La Recherche Médicate (INSERM).

Five mouse anti-human B7H6 monoclonal antibodies were identified and characterized, and are described herein. Characterization of the antibodies demonstrated that certain of these monoclonal antibodies recognize different epitopes on the B7H6 protein, shown by competitive binding assays and disclosed herein. Characterization of the antibodies further demonstrated that the two of antibodies at least partially block the B7H6-NKp30 interaction.

Epitope binning can be used to identify antibodies that fall within the scope of the claimed invention. Epitope binning refers to the use of competitive binding assays to identity pairs of antibodies that are, or are not, capable of binding B7H6 protein simultaneously, thereby identifying pairs of antibodies that bind to the same or overlapping epitopes on a protein. Epitope binning experiments provide evidence that antigenically distinct epitopes are present. Additional data are required to identify, or "map" the epitope to a specific amino acid sequence or location of the B7H6 protein molecule.

Competition for binding can be evaluated for any pair of antibodies or fragments. For example, using the appropriate detection reagents, the binding specificity of antibodies or binding fragments from any source can be compared to the binding specificity of the monoclonal antibodies disclosed herein. Epitope binning can be performed with "isolated antibodies" or with cell culture supernatants. Frequently, binning is performed with first round clonal supernatants to guide the choice of clones to be developed further. The antibodies to be compared should be substantially homogeneous antigen binding domains. In the case of "bispecific" or "bifunctional" antibodies the binding specificity of the two different binding sites need to be evaluated or binned independently.

The antibodies of the present invention may be assayed for specific binding by any method known in the art. Many different competitive binding assay format(s) can be used for epitope binning. The immunoassays which can be used include, but are not limited to, competitive assay systems using techniques such western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al., eds, 1994 *Current Protocols in Molecular Biology*, Vol. 1, John Wiley & sons, Inc., New York). Additionally, routine cross-blocking assays such as those described in *Antibodies, A Laboratory Manual*, Cold Spring Harbor Laboratory, Ed Harlow and David Lane, 1988, can be performed.

The BIACORE® (GE Healthcare, Piscaataway, N.J.) is only one of a variety of surface plasmon resonance assay formats that are routinely used to epitope bin panels of monoclonal antibodies. Other references, e.g., The Epitope Mapping Protocols, *Methods in Molecular Biology*, Vol. 66, Glenn Morris ed. Humana Press, 1996, describe alternative methods that could be used to bind antibodies and would be expected to provide comparable information regarding the binding specificity of the antibodies to B7H6 ligand. When using the BIACORE® system, epitope binning experiments are performed with soluble, native or recombinant antigen. Epitope binning studies can be performed on a BIACORE1000® system (GE Healthcare, Piscataway, N.J.). BIAlogue® v. 1.2 software can be used for programming run methods. For example, to bin mouse monoclonal antibodies raised against B7H6, polyclonal goat anti-Mouse IgG Fc antibody (Jackson ImmunoResearch Laboratories, West Grove, Pa.) can be covalently immobilized to a BIACORE® CM5 sensor chip and used to bind (capture) the primary monoclonal antibody of test series to the chip. Unoccupied Fc binding sites on the chip are then blocked using a polyclonal IgG Fc fragment (Jackson ImmunoResearch Laboratories). Subsequently, B7H6 protein is injected and allowed to specifically bind to the captured primary monoclonal antibody. The BIACORE® instrument measures the mass of protein bound to the sensor chip, and the binding of both the primary antibody and B7H6 antigen can be verified for each cycle. Following the binding of the primary antibody and antigen to the chip, soluble secondary antibody is injected and allowed to bind to the pre-bound antigen. If the secondary monoclonal antibody is capable of binding the B7H6 antigen simultaneously with the primary monoclonal antibody, its binding is detected by the BIACORE®. If, however, the secondary monoclonal antibody is not capable of binding the B7H6 antigen simultaneously with the primary monoclonal antibody, no additional binding is detected. Each monoclonal antibody is tested against itself as a negative control to establish the level of the background (no-binding) signal.

A label-free competitive ELISA format (LFC-ELISA) can also be used to bin antibodies. This method is described by Nagata et al., *J. Immunol. Methods* 292:141-155, 2004, and utilizes biotinylated B7H6. For the example of binning mouse monoclonal antibodies raised against B7H6, microtiter plates are coated at 100 µL/well with 1 µg/mL of a goat anti-mouse IgG Fc-γ specific antibody (Jackson ImmunoResearch) diluted in ELISA B (PBS, 0.1% Tween 20, 1% BSA). After binding of this coating antibody for 3 hours at ambient temperature, each mAb-containing conditioned media is diluted in ELISA B to yield an approximate mAb concentration of 0.5 µg/mL and allowed to bind to the goat anti-mouse IgG coated plates overnight at 4° C. (mAb#1). In parallel, a second set of conditioned medias (mAb#2) are diluted in polystyrene test tubes to approximately 0.5 µg/mL mAb in ELISA B, mixed with 50 ng/mL biotinylated B7H6 antigen, and incubated overnight at 4° C. After incubation of mAb#1 with the coating antibody, the plates are blocked with an unrelated antibody to saturate unoccupied binding sites on the plate. The mAb#2-biotin-B7H6 mixtures are added to the plate and allowed to bind. As a control for (non-competition) in the assay, 50 ng/mL biotinylated B7H6 is added directly (without pre-incubation with mAb#2) to wells containing immobilized mAb#1. After incubation with the biotinylated-B7H6-mAb#2 complex, streptavidin-HRP (Pierce, Rockford, Ill.) is added to the plate at 0.5 µg/mL. The plates are developed with TMB substrate (BioFX Laboratories, Owings Mills, Md.), and the absorbance of the individual wells at 450 nm is measured with a plate reader (Molecular Devices SPECTRA-MAX 340, Sunnyvale, Calif.). If mAb#1 binds to a different epitope from mAb#2, the biotin-B7H6-mAb#2 complex will bind to the plate resulting in a high absorbance reading. If mAb#1 binds to the same epitope as mAb#2, the biotin-B7H6-MAb#2 complex will not bind to the plate resulting in a low absorbance reading.

In some embodiments, an anti-human-B7H6 monoclonal antibody of the present invention is capable of inhibiting the interaction of B7H6 with human NKp30; such antibodies are useful, for example, for inhibiting cellular or other physiological events associated with the interaction of B7H6 with NKp30, including, for example, B7H6- and/or NKp30-mediated intracellular signaling and associated effector function (e.g., NKp30-mediated cytolytic activity).

Antibodies to B7H6 can be obtained, for example, using the product of a B7H6 expression vector or B7H6 isolated from a natural source as an antigen. Particularly useful anti-human-B7H6 monoclonal antibodies "bind specifically" to B7H6. Antibodies are considered to be specifically binding if the antibodies exhibit at least one of the following two properties: (1) antibodies bind to B7H6 with a threshold level of binding activity, and (2) antibodies do not significantly cross-react with polypeptides related to B7H6.

With regard to the first characteristic, antibodies specifically bind if they bind to a B7H6 polypeptide, peptide, or epitope with a binding affinity ($K_a$) of $10^6 M^{-1}$ or greater, preferably $10^7 M^{-1}$ or greater, more preferably $10^8 M^{-1}$ or greater, and most preferably $10^9 M^{-1}$ or greater. The binding affinity of an antibody can be readily determined by one of ordinary skill in the art, for example, by Scatchard analysis (Scatchard, *Ann. NY Acad. Sci.* 51:660, 1949). With regard to the second characteristic, antibodies do not significantly cross-react with related polypeptide molecules, for example, if they detect B7H6, but not presently known polypeptides using a standard Western blot analysis. Examples of known related polypeptides include known B7 family members.

Anti-human-B7H6 monoclonal antibodies can be produced using antigenic B7H6 epitope-bearing peptides and polypeptides. Antigenic epitope-bearing peptides and polypeptides typically contain a sequence of at least nine, or between 15 to about 30 amino acids contained within the amino acid sequence of SEQ ID NO:2. However, peptides or polypeptides comprising a larger portion of an amino acid sequence of the invention, containing from 30 to 50 amino acids, or any length up to and including the entire amino acid sequence of a B7H6 polypeptide, also are useful for inducing antibodies that bind with B7H6. It is desirable that the amino acid sequence of the epitope-bearing peptide is selected to provide substantial solubility in aqueous solvents (i.e., the sequence includes relatively hydrophilic residues, while hydrophobic residues are typically avoided). In addition, amino acid sequences containing proline residues may be also be desirable for antibody production.

Potential antigenic sites in B7H6 can be identified using the Jameson-Wolf method, Jameson and Wolf (*CABIOS* 4:181, 1988), as implemented by the PROTEAN program (version 3.14) of LASERGENE (DNASTAR; Madison, Wis.). Default parameters may be used in this analysis.

The Jameson-Wolf method predicts potential antigenic determinants by combining six major subroutines for protein structural prediction. For example, the Hopp-Woods method (see Hopp et al., *Proc. Nat'l Acad. Sci. USA* 78:3824, 1981) may first be used to identify amino acid sequences representing areas of greatest local hydrophilicity (parameter: seven residues averaged). In the second step, Emini's method (see Emini et al., *J. Virology* 55:836, 1985) may be used to calculate surface probabilities (parameter: surface decision threshold (0.6)=1). Third, the Karplus-Schultz method, Karplus and Schultz (*Naturwissenschaften* 72:212, 1985) may be used to predict backbone chain flexibility (parameter: flexibility threshold (0.2)=1). In fourth and fifth steps of analysis, secondary structure predictions may be applied to the data using the methods of Chou-Fasman (see Chou, "Prediction of Protein Structural Classes from Amino Acid Composition," in *Prediction of Protein Structure and the Principles of Protein Conformation* 549-586 (Fasman, ed., Plenum Press 1990) and Garnier-Robson (see Garnier et al., *J. Mol. Biol.* 120:97, 1978) (Chou-Fasman parameters: conformation table=64 proteins; α region threshold=103; β region threshold=105; Garnier-Robson parameters: α and β decision constants=0). In a sixth subroutine, flexibility parameters and hydropathy/solvent accessibility factors may be combined to determine a surface contour value, designated as the "antigenic index." Finally, a peak broadening function may be applied to the antigenic index, which broadens major surface peaks by adding, e.g., 20, 40, 60, or 80% of the respective peak value to account for additional free energy derived from the mobility of surface regions relative to interior regions. This calculation, however, is typically not applied to any major peak that resides in a helical region, since helical regions tend to be less flexible.

Methods for generating monoclonal antibodies are generally known. For example, rodent monoclonal antibodies to specific antigens may be obtained by methods known to those skilled in the art (see, e.g., Kohler et al., *Nature* 256:495, 1975; Coligan et al. (eds.), *Current Protocols in Immunology*, Vol. 1 2.5.1-2.6.7 (John Wiley & Sons 1991) ["Coligan"]; Picksley et al., "Production of monoclonal antibodies against proteins expressed in *E. coli*," in *DNA Cloning* 2: *Expression Systems*, 2nd Edition 93 (Glover et al., eds., Oxford University Press 1995). In certain variations, monoclonal antibodies are obtained by injecting mice with a composition comprising a B7H6 gene product (e.g., a polypeptide comprising or consisting of SEQ ID NO:2 residues 25-266), verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

An anti-human-B7H6 monoclonal antibody may also be a human monoclonal antibody, or an antibody derived therefrom. Human monoclonal antibodies may be obtained, for example, from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13, 1994; Lonberg et al., *Nature* 368:856, 1994; and Taylor et al., *Int. Immun.* 6:579, 1994.

Alternative techniques for generating or selecting monoclonal antibodies include, for example, in vitro exposure of lymphocytes to B7H6 protein or peptide, and selection of antibodies from antibody display libraries in phage or similar vectors (for instance, through use of immobilized or labeled B7H6 protein or peptide). Techniques for creating and screening such antibody display libraries are known in the art (see, e.g., U.S. Pat. Nos. 5,580,717; 5,885,793; 5,969,108; and 6,040,136).

Monoclonal antibodies can be isolated and purified from cell cultures by a variety of well-established techniques. Such isolation techniques include, for example, affinity chromatography with Protein-A Sepharose, size-exclusion chromatography, and ion-exchange chromatography (see, e.g., Coligan at pages 2.7.1-2.7.12 and pages 2.9.1-2.9.3; Baines et al., "Purification of Immunoglobulin G (IgG)," in *Methods in Molecular Biology* (Vol. 10) 79-104 (The Humana Press, Inc. 1992)).

The amino acid sequence of a monoclonal antibody can be varied through the application of recombinant DNA techniques. Thus, antibodies can be redesigned to obtain desired characteristics. Modified antibodies can provide, for example, improved stability and/or therapeutic efficacy relative to its non-modified form. The possible variations are many and range from the changing of just one or a few amino acids to the complete redesign of, for example, the variable or constant region. Changes in the constant region will, in general, be made in order to improve or alter characteristics, such as complement fixation, interaction with membranes, and other effector functions. Typically, changes in the variable region will be made in order to improve the antigen binding characteristics, improve variable region stability, or reduce the risk of immunogenicity. Phage display techniques can also be employed. See, e.g., Huse et al., *Science* 246:1275-1281, 1989; Ladner et al., U.S. Pat. No. 5,571,698.

In some embodiments, an anti-human-B7H6 monoclonal antibody is an antibody fragment comprising an antigen-binding domain of an intact (whole) antibody. Such antibody fragments can be obtained, for example, by proteolytic hydrolysis of an antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent $F_{ab}$ fragments and an $F_c$ fragment directly. These methods are described, for example, in U.S. Pat. No. 4,331,647 to Goldenberg; Nisonoff et al., *Arch Biochem. Biophys.* 89:230, 1960; Porter, *Biochem. J.* 73:119, 1959; Edelman et al., in *Methods in Enzymology* (Vol. 1) 422 (Academic Press 1967); and Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659, 1972. Alternatively, the variable chains can be linked by an intermolecular disulfide bond or cross-linked by chemicals such as glutaraldehyde (see, e.g., Sandhu, *Crit. Rev. Biotech.* 12:437, 1992).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97, 1991. (See also Bird et al., *Science* 242:423, 1988; U.S. Pat. No. 4,946,778 to Ladner et al.; Pack et al., *Bio/Technology* 11:1271, 1993, and Sandhu, supra.) As an illustration, a scFv can be obtained by screening a library of scFvs (e.g., scFvs displayed phage) for specific binding to B7H6 (for example, immobilized or labeled B7H6 protein or peptide).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, e.g., Larrick et al., *Methods: A Companion to Methods in Enzymology* 2:106, 1991; Courtenay-Luck, "Genetic Manipulation of Monoclonal Antibodies," in *Monoclonal Antibodies: Production, Engineering and Clinical Application* 166 (Ritter et al., eds., Cambridge University Press 1995); and Ward et al., "Genetic Manipulation and Expression of Antibodies," in *Monoclonal Antibodies: Principles and Applications* 137 (Birch et al., eds., Wiley-Liss, Inc. 1995)).

Alternatively, an anti-human-B7H6 monoclonal antibody may be a "humanized" monoclonal antibody derived from a non-human anti-B7H6 antibody. Humanized monoclonal antibodies are produced by transferring non-human (e.g., mouse) complementary determining regions from heavy and light variable chains of the non-human immunoglobulin into a human variable domain. Typical residues of human antibodies are then substituted in the framework regions of the non-human counterparts. The use of humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833, 1989. Techniques for producing humanized monoclonal antibodies are described, for example, by Jones et al., *Nature* 321:522, 1986; Carter et al., *Proc. Nat'l Acad. Sci. USA* 89:4285, 1992; Sandhu, *Crit. Rev. Biotech.* 12:437, 1992; Singer et al., *J. Immun.* 150:2844, 1993; Sudhir (ed.), *Antibody Engineering Protocols* (Humana Press, Inc. 1995); Kelley, "Engineering Therapeutic Antibodies," in *Protein Engineering: Principles and Practice* 399-434 (Cleland et al., eds., John Wiley & Sons, Inc. 1996); and U.S. Pat. No. 5,693,762 to Queen et al.

In certain variations, an anti-human-B7H6 monoclonal antibody includes an Fc region, which comprises the $C_H2$ and $C_H3$ domains of an immunoglobulin (Ig) heavy chain and typically a portion of an Ig hinge region. Fc is responsible for two of the highly desirable properties of an IgG: recruitment of effector function and a long serum half-life. The ability to kill target cells to which an antibody is attached stems from the activation of immune effector pathway (ADCC) and the complement pathway (CDC) through the binding of Fc to Fc receptors and the complement protein, C1q, respectively. The binding is mediated by residues located primarily in the lower hinge region and upper $C_H2$ domain. (See, e.g., Wines et al., *J. Immunol.* 164:5313, 2000; Woof and Burton, *Nature Reviews* 4:1, 2004.) The long half-life in serum demonstrated by IgG is mediated through a pH dependent interaction between amino acids in the $C_H2$ and $C_H3$ domain and the neonatal Fc receptor, FcRn. (See, e.g., Getie and Ward, *Immunology Today* 18:592, 1997; Petkova et al., *Int. Immunol.* 18:1759, 2006.)

Accordingly, in certain embodiments of an anti-human-B7H6 monoclonal antibody comprising an Fc region, the Fc region has ADCC and/or CDC activity. Such antibodies are particularly useful for mediating killing of target cells expressing B7H6 such as, for example, cancer cells or virally infected cells. In other embodiments, an anti-human-B7H6 monoclonal antibody comprises an Fc region that lacks one or more effector functions (e.g., lacks ADCC and/or CDC activity). Fc regions lacking or having substantially reduced effector function may be obtained, for example, by introducing one or more amino acid substitutions into a native Fc region sequence, such that the Fc region does not bind, or has substantially reduced binding, to cytolytic Fc receptors and/or the C1q complement protein. A variety of modified Fc regions lacking or having substantially reduced effector functions are known in the art. Particularly suitable Fc regions lacking or having substantially reduced effector function include, for example, variant Fc regions as described in US Patent Application Publication No. 2009/0220502

In certain embodiments comprising an Fc region, the Fc region is a single chain Fc (scFc), which comprises two Fc domain monomers joined by a flexible linker, such that the two Fc monomers are capable of dimerization to form a functional, dimeric Fc domain. For example, in some variations of an anti-human-B7H6 monoclonal antibody comprising a scFc, the antibody comprises a single chain Fv (scFv) fused to the scFc portion, wherein the scFv portion specifically binds to B7H6. Single chain Fc polypeptides, including fusion polypeptides comprising scFc and one more antigen-binding domains (e.g., scFv), are further described in International PCT Patent Application Publication No. WO 08/0131242, entitled "Single Chain Fc, Methods of Making, and Methods of Treatment," the disclosure of which is incorporated by reference herein in its entirety.

Moreover, anti-human-B7H6 monoclonal antibodies or antibody fragments of the present invention can be PEGylated using methods in the art and described herein.

An anti-human-B7H6 monoclonal antibody can be conjugated with a detectable label to form an anti-B7H6 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^{3}H$, $^{125}I$, $^{131}I$, $^{35}S$ and $^{14}C$.

Anti-B7H6 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-B7H6 immunoconjugates can be detectably labeled by coupling an antibody to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-B7H6 immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-B7H6 immunoconjugates can be detectably labeled by linking an anti-human-B7H6 monoclonal antibody to an enzyme. When the anti-B7H6-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-human-B7H6 monoclonal antibodies can be accomplished using standard techniques known to the art. Typical methodology in this regard is described by Kennedy et al., *Clin. Chim. Acta* 70:1, 1976; Schurs et al., *Clin. Chim. Acta* 81:1, 1977; Shih et al., *Int'l J. Cancer* 46:1101, 1990; Stein et al., *Cancer Res.* 50:1330, 1990; and Coligan, supra.

Moreover, the convenience and versatility of immunochemical detection can be enhanced by using anti-human-B7H6 monoclonal antibodies that have been conjugated with avidin, streptavidin, and biotin. (See, e.g., Wilchek et al. (eds.), "Avidin-Biotin Technology," *Methods In Enzymology* (*Vol.* 184) (Academic Press 1990); Bayer et al., "Immunochemical Applications of Avidin-Biotin Technology," in *Methods In Molecular Biology* (*Vol.* 10) 149-162 (Manson, ed., The Humana Press, Inc. 1992).)

Methods for performing immunoassays are well-established. (See, e.g., Cook and Self, "Monoclonal Antibodies in Diagnostic Immunoassays," in *Monoclonal Antibodies: Production, Engineering, and Clinical Application* 180-208 (Ritter and Ladyman, eds., Cambridge University Press 1995); Perry, "The Role of Monoclonal Antibodies in the Advancement of Immunoassay Technology," in *Monoclonal Antibodies: Principles and Applications* 107-120 (Birch and Lennox, eds., Wiley-Liss, Inc. 1995); Diamandis, *Immunoassay* (Academic Press, Inc. 1996).)

IV. Anti-B7H6 Monoclonal Antibody-Drug Conjugates

In another aspect, the present invention provides an anti-human-B7H6 monoclonal antibody-drug conjugate. An "anti-human-B7H6 monoclonal antibody-drug conjugate" as used herein refers to an anti-human-B7H6 monoclonal antibody (as described in Section III, supra) conjugated to a therapeutic agent. Such anti-human-B7H6 monoclonal antibody-drug conjugates produce clinically beneficial effects on B7H6-expressing cells when administered to a subject, such as, for example, a subject with a B7H6-expressing cancer, typically when administered alone but also in combination with other therapeutic agents.

In typical embodiments, an anti-human-B7H6 monoclonal antibody is conjugated to a cytotoxic agent, such that the resulting antibody-drug conjugate exerts a cytotoxic or cytostatic effect on a B7H6-expressing cell (e.g., a B7H6-expressing cancer cell) when taken up or internalized by the cell. Particularly suitable moieties for conjugation to antibodies are chemotherapeutic agents, prodrug converting enzymes, radioactive isotopes or compounds, or toxins. For example, an anti-human-B7H6 monoclonal antibody can be conjugated to a cytotoxic agent such as a chemotherapeutic agent (see infra) or a toxin (e.g., a cytostatic or cytocidal agent such as, for example, abrin, ricin A, pseudomonas exotoxin, or diphtheria toxin). Examples of additional agents that are useful for conjugating to an anti-human-B7H6 monoclonal antibody are provided infra.

In other embodiments, an anti-human-B7H6 monoclonal antibody is conjugated to a pro-drug converting enzyme. The pro-drug converting enzyme can be recombinantly fused to the antibody or chemically conjugated thereto using known methods. Exemplary pro-drug converting enzymes are carboxypeptidase G2, β-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Amon et al., "Monoclonal Antibodies For Immunotargeting Of Drugs In Cancer Therapy," in *Monoclonal Antibodies And Cancer Therapy* (Reisfeld et al. eds., Alan R. Liss, Inc., 1985); Hellstrom et al., "Antibodies For Drug Delivery," in *Controlled Drug Delivery* (Robinson et al. eds., Marcel Deiker, Inc., 2nd ed. 1987); Thorpe, "Antibody Carriers Of Cytotoxic Agents In Cancer Therapy: A Review," in *Monoclonal Antibodies '84: Biological And Clinical Applications* (Pinchera et al. eds., 1985); "Analysis, Results, and Future Prospective of the Therapeutic Use of Radiolabeled Antibody In Cancer Therapy," in *Monoclonal Antibodies For Cancer Detection And Therapy* (Baldwin et al. eds., Academic Press, 1985); and Thorpe et al., 1982, *Immunol. Rev.* 62:119-58. See also, e.g., PCT publication WO 89/12624.)

In certain variations, in accordance with methods described herein, an anti-human-B7H6 monoclonal antibody-drug conjugate is internalized and accumulates within a B7H6-expressing cell, where antibody-drug conjugate exerts a therapeutic effect (e.g., a cytotoxic or cytostatic effect). Methods for determining accumulation and rates of accumulation are found in, for example, WO 2004/010957, entitled "Drug Conjugates and Their Use for Treating Cancer, an Autoimmune Disease or an Infectious Disease."

In typical embodiments, when using an anti-human-B7H6 monoclonal antibody conjugated to a therapeutic agent (e.g., a drug or a prodrug converting enzyme), the agent is preferentially active when internalized by B7H6-expressing cells (e.g., cells of a B7H6-expressing cancer) to be treated. In other embodiments, the anti-human-B7H6 monoclonal antibody-drug conjugate is not internalized, and the drug is effective to exert a therapeutic effect (e.g., depletion or inhibition of growth of B7H6-expressing cells) by binding to the cell membrane.

To minimize activity of a therapeutic agent outside a B7H6-expressing cell (e.g., a B7H6-expressing cancer cell), a therapeutic agent is typically conjugated in a manner that reduces its activity unless it is cleaved off the antibody (e.g., by hydrolysis or by a cleaving agent). In such embodiments, the therapeutic agent is attached to the antibody with a cleavable linker that is sensitive to cleavage in the intracellular environment of the B7H6-expressing cell but is not substantially sensitive to the extracellular environment, such that the conjugate is cleaved from the antibody when it is internalized by the B7H6-expressing cell (e.g., in the endosomal or, for example, by virtue of pH sensitivity or protease sensitivity, in the lysosomal environment or in a caveolea). (See Section IV(A), infra.)

Further, in certain embodiments, an antibody-drug conjugate comprises a therapeutic agent that is charged relative to the plasma membrane, thereby further minimizing the ability of the agent to cross the plasma membrane once internalized by a cell. As used herein, a "charged agent" means an agent that (a) is polarized, such that one region of the agent has a charge relative to the plasma membrane, or (b) has a net charge relative to the plasma membrane.

A. Linkers

Typically, a B7H6 antibody-drug conjugate comprises a linker region between the therapeutic agent and the anti-human-B7H6 monoclonal antibody. As noted supra, in certain embodiments, the linker is cleavable under intracellular conditions, such that cleavage of the linker releases the therapeutic agent from the antibody in the intracellular environment.

For example, in some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. Typically, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, Pharm. Therapeutics 83:67-123, 1999). Most typical are peptidyl linkers that are cleavable by enzymes that are present in B7H6-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker). Other such linkers are described, e.g., in U.S. Pat. No. 6,214,345. In specific embodiments, the peptidyl linker cleavable by an intracellular protease is a Val-Cit (valine-citrulline) linker or a Phe-Lys (phenylalanine-lysine) linker (see, e.g., U.S. Pat. No. 6,214,345, which describes the synthesis of doxorubicin with the Val-Cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, a pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, Pharm. Therapeutics 83:67-123, 1999; Neville et al., Biol. Chem. 264:14653-14661, 1989.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929)).

In yet other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT. (See, e.g., Thorpe et al., Cancer Res. 47:5924-5931, 1987; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

In yet other variations, the linker is a malonate linker (Johnson et al., Anticancer Res. 15:1387-93, 1995), a maleimidobenzoyl linker (Lau et al., Bioorg-Med-Chem. 3:1299-1304, 1995), or a 3'-N-amide analog (Lau et al., Bioorg-Med-Chem. 3:1305-12, 1995).

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of an antibody-drug conjugate, are cleaved when the antibody-drug conjugate is present in an extracellular environment (e.g., in plasma). Whether a linker is not substantially sensitive to the extracellular environment can be determined, for example, by incubating independently with plasma both (a) the antibody-drug conjugate (the "antibody-drug conjugate sample") and (b) an equal molar amount of unconjugated antibody or therapeutic agent (the "control sample") for a predetermined time period (e.g., 2, 4, 8, 16, or 24 hours) and then comparing the amount of unconjugated antibody or therapeutic agent present in the antibody-drug conjugate sample with that present in the control sample, as measured, for example, by high performance liquid chromatography.

In some variations, the linker promotes cellular internalization. In certain embodiments, the linker promotes cellular internalization when conjugated to the therapeutic agent (i.e., in the milieu of the linker-therapeutic agent moiety of the antibody-drug conjugate). In yet other embodiments, the linker promotes cellular internalization when conjugated to both the therapeutic agent and the anti-B7H6 antibody (i.e., in the milieu of the antibody-drug conjugate).

A variety of linkers that can be used with the present compositions and methods are described in, for example, WO 2004/010957, entitled "Drug Conjugates and Their Use for Treating Cancer, an Autoimmune Disease or an Infectious Disease."

B. Therapeutic Agents

In accordance with the present invention, any agent that exerts a therapeutic effect on a B7H6-expressing cell can be used as the therapeutic agent for conjugation to an anti-human-B7H6 monoclonal antibody. In certain embodiments, such as for treatment of a B7H6-expressing cancer, the therapeutic agent is a cytotoxic agent.

Useful classes of cytotoxic agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and-carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065 (Li et al., *Cancer Res.* 42:999-1004, 1982), chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluorodeoxyuridine, etoposide phosphate (VP-16), 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide (VM-26), 6-thioguanine, thioTEPA, topotecan, vinblastine, vincristine, and vinorelbine.

Particularly suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38 (7-ethyl-10-hydroxycamptothein), topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In certain embodiments, a cytotoxic agent is a conventional chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to an anti-B7H6-expressing antibody.

In specific variations, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP (dimethylvaline-valine-dolaisoleuine-dolaproine-phenylalanine-p-phenylenediamine), MMAF (dovaline-valine-dolaisoleunine-dolaproine-phenylalanine), and MAE (monomethyl auristatin E). The synthesis and structure of auristatin E and its derivatives are described in U.S. Patent Application Publication No. 20030083263; International Patent Publication Nos. WO 2002/088172 and WO 2004/010957; and U.S. Pat. Nos. 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In other variations, the cytotoxic agent is a DNA minor groove binding agent. (See, e.g., U.S. Pat. No. 6,130,237.) For example, in certain embodiments, the minor groove binding agent is a CBI compound. In other embodiments, the minor groove binding agent is an enediyne (e.g., calicheamicin).

In certain embodiments, an antibody-drug conjugate comprises an anti-tubulin agent. Examples of anti-tubulin agents include, for example, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin. In some embodiments, the cytotoxic agent is a maytansinoid, another group of anti-tubulin agents. For example, in specific embodiments, the maytansinoid is maytansine or DM-1 (Immuno Gen, Inc.; see also Chari et al., *Cancer Res.* 52:127-131, 1992).

In other embodiments, the cytotoxic agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

C. Formation of Anti-B7H6 Antibody-Drug Conjugates

The generation of anti-human-B7H6 monoclonal antibody-drug conjugates can be accomplished by any technique known to the skilled artisan. Briefly, an anti-human-B7H6 monoclonal antibody-drug conjugate comprises an anti-human-B7H6 monoclonal antibody, a drug, and optionally a linker that joins the drug and the antibody. A number of different reactions are available for covalent attachment of drugs to antibodies. This is often accomplished by reaction of the amino acid residues of the antibody molecule, including the amine groups of lysine, the free carboxylic acid groups of glutamic and aspartic acid, the sulfhydryl groups of cysteine, and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of the antibody molecule. Also available for attachment of drugs to antibodies is the Schiff base reaction. This method involves the periodate oxidation of a drug that contains glycol or hydroxy groups, thus forming an aldehyde which is then reacted with the antibody molecule. Attachment occurs via formation of a Schiff base with amino groups of the antibody molecule. Isothiocyanates can also be used as coupling agents for covalently attaching drugs to antibodies. Other techniques are known to the skilled artisan and within the scope of the present invention. Non-limiting examples of such techniques are described in, e.g., U.S. Pat. Nos. 5,665,358; 5,643,573; and 5,556,623.

In some embodiments, an intermediate, which is the precursor of the linker, is reacted with the drug under appropriate conditions. In certain embodiments, reactive groups are used on the drug and/or the intermediate. The product of the reaction between the drug and the intermediate, or the derivatized drug, is subsequently reacted with the anti-human-B7H6 monoclonal antibody under appropriate conditions.

D. Assays for Cytotoxic or Cytostatic Activities

In certain embodiments, an anti-human-B7H6 monoclonal antibody-drug conjugate comprises an anti-human-B7H6 monoclonal antibody conjugated to a cytotoxic agent, such that the antibody-drug conjugate exerts a cytotoxic or cytostatic effect on a B7H6-expressing cell (e.g., a B7H6-expressing cancer cell). B7H6-expressing cells that can be assayed for a cytotoxic or cytostatic effect of an anti-human-B7H6 monoclonal antibody-drug conjugate can be culture cell lines such as, for example, those listed in Table 5, infra. Once an anti-human-B7H6 monoclonal antibody-drug conjugate is confirmed as exerting a cytotoxic or cytostatic on B7H6-expressing cells, its therapeutic value can be validated in an appropriate animal model. In preferred embodiments, an anti-human-B7H6 monoclonal antibody-drug conjugate comprising a cytotoxic agent is used to treat a B7H6-expressing cancer. Exemplary animal models of various cancers, which may be used to evaluate therapeutic efficacy of an antibody-drug conjugate of the present invention, are described in Section V(B) and in Examples X, infra.

Methods of determining whether an agent exerts a cytostatic or cytotoxic effect on a cell are generally known in the art. Illustrative examples of such methods are described below. Determination of any of these effects on B7H6-expressing cells indicates that an anti-human-B7H6 monoclonal antibody-drug conjugate is useful in the treatment or prevention of diseases or disorders having a pathology mediated, at least in part, by aberrant growth or activation of B7H6-expressing cells, such as, for example, a B7H6-expressing cancer.

For determining whether an anti-human-B7H6 monoclonal antibody-drug conjugate exerts a cytostatic effect on B7H6-expressing cells, a thymidine incorporation assay may be used. For example, B7H6-expressing cells, at a density of 5,000 cells/well of a 96-well plate, can be cultured for a 72-hour period and exposed to 0.5 µCi of $^3$H-thymidine during the final 8 hours of the 72-hour period, and the incorporation of $^3$H-thymidine into cells of the culture is measured in the presence and absence of the antibody-drug conjugate.

For determining cytotoxicity, necrosis or apoptosis (programmed cell death) can be measured. Necrosis is typically accompanied by increased permeability of the plasma membrane, swelling of the cell, and rupture of the plasma membrane. Apoptosis is typically characterized by membrane blebbing, condensation of cytoplasm, and the activation of endogenous endonucleases.

Cell viability can be measured by determining in a cell the uptake of a dye such as neutral red, trypan blue, or AlamarBlue® (Trek Diagnostic Systems, Cleveland, Ohio). See, also, e.g., Page et al., *Intl. J. of Oncology* 3:473-476, 1993. In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., *J. Nat'l Cancer Inst.* 82:1107-12, 1990).

Alternatively, a tetrazolium salt, such as MTT, is used in a quantitative calorimetric assay for mammalian cell survival and proliferation by detecting living, but not dead, cells (see, e.g., Mosmann, *J. Immunol. Methods* 65:55-63, 1983).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in *Biochemica*, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has previously been described by Duke and Cohen, *Current Protocols In Immunology* (Coligan et al. eds., 1992, pp. 3.17.1-3.17.16). Cells can be also labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsining the attached cells, combining the preparations following a centrifugation wash step (e.g., 10 minutes, 2000 rpm), and detecting apoptosis (e.g., by measuring DNA fragmentation). (See, e.g., Piazza et al., *Cancer Research* 55:3110-16, 1995).

V. Methods of Use

A. General

In another aspect, the present invention provides methods of modulating activity (e.g., cytolytic activity) of an NKp30-expressing cell, including, for example, natural killer (NK) cells and T cells (e.g., CD8$^+$ T cells). Such methods include, e.g., methods for treatment of diseases or disorders associated with increased activity of an NKp30-expressing cell. Suitable antibodies include antibodies capable of competing for binding to B7H6 with an antibody produced by a hybridoma selected from the group consisting of (i) the hybridoma of clone 4E5.5 (Deposit No. CNCM I-4242); (ii) the hybridoma of clone 9G9.2 (Deposit No. CNCM I-4243); (iii) the hybridoma of clone 10E2.9 (Deposit No. CNCM I-4244); and (iv) the hybridoma of clone 17B1.3 (Deposit No. CNCM I-4245). In particular variations, the antibody is a chimeric or humanized antibody derived from an antibody produced by a hybridoma selected from (i)-(iv) above.

In some embodiments, antibodies of the present invention are for use in interferring with the interaction of B7H6 with NKp30. For use in such embodiments, methods comprise contacting a cell expressing functional B7H6, in the presence of an NKp30-expressing cell, with an effective amount of an anti-human-B7H6 monoclonal antibody or other agent capable of interfering with the interaction of B7H6 with NKp30. Suitable antibodies include antibodies capable of competing for binding to B7H6 with an antibody produced by a hybridoma selected from (i) the hybridoma of clone 4E5.5 (Deposit No. CNCM I-4242) or (ii) the hybridoma of clone 17B1.3 (Deposit No. CNCM I-4245). In particular variations, the antibody is a chimeric or humanized antibody derived from an antibody produced by a hybridoma selected from (i) and (ii) above. Such methods can be performed in vitro, ex vivo, or in vivo. In certain preferred variations, the NKp30-expressing cell is an NK cell and the use or method of modulating NK cell activity would be, for example, in the treatment of a disease or disorder associated with increased NK cell activity. In other variations, the NKp30-expressing cell is an NKp30 expressing T cell (e.g., a CD8$^+$ T cell) and the use or method of modulating NKp30-expressing T cell activity would be, for example, for treatment of a disease or disorder associated with increased activity of NKp30-expressing T cells. Certain T cells, including CD8$^+$ T cells, have been shown to express NKp30. (See, e.g., Srivastava and Srivastava, *Leuk. Res.* 30:37-46, 2006.)

As noted above, in particular variations, the antibodies of the present invention are for use in treating a disease or disorder associated with NK cell activity. For example, in some embodiments, the method of using the antibodies includes administering an effective amount of an anti-human-B7H6 monoclonal antibody capable of interfering with the interaction of B7H6 with NKp30 to a subject suffering from, or at an elevated risk of developing, an NK-cell-mediated disease or disorder (for example, NK-cell-mediated allograft rejection such as, e.g., NK-cell-mediated bone marrow cell (BMC) allograft rejection). Embodied in the present invention is a method comprising an anti-human-B7H6 monoclonal antibody used to suppress NK-cell-mediated bone marrow allograft rejection. Bone marrow transplantation (BMT) has become an accepted method of therapy for the treatment of various hematologic malignancies. The efficacy of allogeneic BMT is limited, however, by certain obstacles such as, e.g., rejection of the graft. There is ample evidence that NK cells are a barrier to the engraftment of bone marrow allografts and that they alone can mediate the specificity of BMC rejection in mice. (See, e.g., Murphy et al., *J. Exp. Med.* 165:1212-1217, 1987; Murphy et al., *J. Exp. Med.* 166:1499-1509, 1987; Murphy et al., *J. Immunol.* 144:3305-3311, 1990; Murphy et al., *Eur. J. Immunol.* 20:1729-1734, 1990; Murphy et al., *Immunol. Rev.* 181:279-289, 2001.) Clinically, allograft resistance observed in patients with SCID who have received HLA-mismatched BMTs depleted of T cells, without cytoreductive conditioning, is attributed to high activity of NK cells from the donor. (See O'Reilly et al., *Vox. Sang.* 51:81-86, 1986.) Accordingly, antibodies against the extracellular domain of B7H6 and capable of inhibiting the interaction of B7H6 with NKp30, as described herein, may be used during BMT to inhibit NK cell cytolytic activity against allografts and thereby treat or prevent BMC allograft rejection.

In yet other embodiments, an anti-human-B7H6 monoclonal antibody is used to induce antibody dependent cellular cyotoxicity (ADCC) or complement dependent cytotoxicity (CDC) against B7H6-expressing cells, such as, e.g., for the treatment of a disease or disorder characterized by the presence of B7H6-expressing cells. For example, in some embodiments, an anti-human-B7H6 monoclonal antibody is used to induce antibody dependent cellular cyotoxicity (ADCC) or complement dependent cytotoxicity (CDC) against B7H6-expressing cancer cells. Antibody therapy has been particularly successful in cancer treatment because certain tumors either display unique antigens, lineage-specific antigens, or antigens present in excess amounts relative to normal cells. Experimental evidence demonstrates that B7H6 is, relative to normal tissues, highly expressed by many tumor-derived cell lines, including cell lines derived from cancers of the colon, liver, cervix, lung, pancreas, and prostate, as well as those derived from various cancers of the blood such as prohemocytic leukemia, B-cell lymphoma, monocytic lymphoma, erythroleukemia, Burkitt's lymphoma, or chronic myelogenous leukemia. This evidence indicates that B7H6 is a novel tumor-specific or tumor-associated antigen, and that an anti-human-B7H6 monoclonal antibody may be used as an anti-tumor therapeutic. One of the mechanisms associated with the anti-tumor activity of monoclonal antibody therapy is antibody dependent cellular cytotoxicity (ADCC). In ADCC, monoclonal antibodies bind to a target cell (e.g., cancer cell) and specific effector cells expressing receptors for the monoclonal antibody (e.g., NK cells, CD8+ T cells, monocytes, granulocytes) bind the monoclonal antibody/target cell complex resulting in target cell death.

Accordingly, in some embodiments, an anti-human-B7H6 monoclonal antibody comprising an Fc region with effector function is used to induce antibody dependent cellular cytotoxicity (ADCC) or complement dependent cytotoxicity (CDC) against a B7H6-expressing cell. Methods for inducing ADCC generally include contacting the B7H6-expressing cell with an effective amount an anti-human-B7H6 monoclonal antibody comprising an Fc region having ADCC activity, wherein the contacting step is in the presence of a cytolytic immune effector cell expressing an Fc receptor having cytolytic activity. Immune effector cells expressing cytolytic Fc receptors (e.g., FcγRIIIα or CD16) include, for example, NK cells as well certain CD8+ T cells. Methods for inducing CDC generally include contacting the B7H6-expressing cell with an effective amount an anti-human-B7H6 monoclonal antibody comprising an Fc region having CDC activity, wherein the contacting step is in the presence of complement. B7H6-expressing cells that can be targeted for killing using such methods include, for example, cancer cells, such as, e.g., colon cancer cells, liver cancer cells, cervical cancer cells, lung cancer cells, pancreatic cancer cells, prostate cancer cells, prohemocytic leukemia cells, B-cell lymphoma cells, monocytic lymphoma cells, erythroleukemia cells, Burkitt's lymphoma cells, and chronic myelogenous leukemia cells, to name a few. Suitable antibodies include antibodies capable of competing for binding to B7H6 with an antibody produced by a hybridoma selected from the group consisting of (i) the hybridoma of clone 4E5.5 (Deposit No. CNCM I-4242); (ii) the hybridoma of clone 9G9.2 (Deposit No. CNCM I-4243); (iii) the hybridoma of clone 10E2.9 (Deposit No. CNCM I-4244); and (iv) the hybridoma of clone 17B1.3 (Deposit No. CNCM I-4245). In some embodiments, the antibody is capable of competing for binding to B7H6 with an antibody produced by a hybridoma selected from (ii)-(iii) above. In particular variations, the antibody is a chimeric or humanized antibody derived from an antibody produced by a hybridoma selected from (i)-(iv) above or selected from (ii)-(iii) above.

In related embodiments, an anti-human-B7H6 monoclonal antibody comprising an Fc region with effector function, as described herein, is used to treat a B7H6-expressing cancer in a subject. Such methods generally include administering to a subject an effective amount of an anti-human-B7H6 monoclonal antibody comprising an Fc region having ADCC activity and/or CDC activity. B7H6-expressing cancers particularly amenable to treatment using such methods include, for example, cancers of the colon, liver, cervix, lung, pancreas, or prostate, as well as cancers of the blood such as, e.g., prohemocytic leukemia, B-cell lymphoma, monocytic lymphoma, erythroleukemia, Burkitt's lymphoma, or chronic myelogenous leukemia.

In yet other embodiments, an anti-human-B7H6 monoclonal antibody-drug conjugate (see Section IV, supra) is used to deliver a therapeutic agent to a B7H6-expressing cell, where the agent exerts a therapeutic effect. Such methods are particularly useful for the treatment of diseases or disorders characterized by the presence of B7H6-expressing cells. In certain preferred variations utilizing an anti-human-B7H6 monoclonal antibody-drug conjugate, the therapeutic agent is a cytotoxic agent that exerts a cytotoxic or cytostatic effect on a B7H6-expressing cell, such as a B7H6-expressing cancer cell. As indicated above, experimental evidence demonstrates that B7H6 is, relative to normal tissues, highly expressed by many tumor-derived cell lines, including cell lines derived from cancers of the colon, liver, cervix, lung, pancreas, and prostate, as well as those derived from various cancers of the blood such as prohemocytic leukemia, B-cell lymphoma, monocytic lymphoma, erythroleukemia, Burkitt's lymphoma, or chronic myelogenous leukemia. This evidence indicates that B7H6 is a novel tumor-specific or tumor-associated antigen useful for targeting agents having therapeutic efficacy in cancer treatment, particularly cytotoxic agents that can deplete or inhibit the growth of tumor cells. Accordingly, in some embodiments, an anti-human-B7H6 monoclonal antibody-drug conjugate, comprising an anti-human-B7H6 monoclonal antibody conjugated to a cytotoxic agent, is used to treat B7H6-expressing cancer. Suitable antibody-drug conjugates include those comprising an antibody capable of competing for binding to B7H6 with an antibody produced by a hybridoma selected from the group consisting of (i) the hybridoma of clone 4E5.5 (Deposit No. CNCM I-4242); (ii) the hybridoma of clone 9G9.2 (Deposit No. CNCM I-4243); (iii) the hybridoma of clone 10E2.9 (Deposit No. CNCM I-4244); and (iv) the hybridoma of clone 17B1.3 (Deposit No. CNCM I-4245). In some embodiments, the antibody-drug conjugate comprises an antibody is capable of competing for binding to B7H6 with an antibody produced by a hybridoma selected from (ii)-(iii) above. In particular variations, the antibody-drug conjugate comprises a chimeric or humanized antibody derived from an antibody produced by a hybridoma selected from (i)-(iv) above or selected from (ii)-(iii) above.

In each of the embodiments of the treatment methods described herein, the anti-human-B7H6 monoclonal antibody or anti-human-B7H6 monoclonal antibody-drug conjugate is delivered in a manner consistent with conventional methodologies associated with management of the disease or disorder for which treatment is sought. In accordance with the disclosure herein, an effective amount of the antibody or antibody-drug conjugate is administered to a subject in need of such treatment for a time and under conditions sufficient to prevent or treat the disease or disorder.

Subjects for administration of anti-human-B7H6 monoclonal antibodies or antibody-drug conjugates as described herein include patients at higher than normal risk for developing a disease or disorder mediated by NKp30-expressing cells or characterized by the presence of B7H6-expressing cells, as well as patients presenting with an existing disease or disorder. In certain embodiments where the subject is not yet suffering from a disease or disorder, the use is for screening or diagnostic. In other certain embodiments, the subject has been diagnosed as having the disease or disorder for which treatment is sought. Further, subjects can be monitored during the course of treatment for any change in the disease or disorder (e.g., for an increase or decrease in clinical symptoms of the disease or disorder).

In prophylactic applications, pharmaceutical compositions (medicants) are administered to a patient susceptible to, or otherwise at risk of, a particular disease in an amount sufficient to eliminate or reduce the risk or delay the outset of the disease. In therapeutic applications, compositions are administered to a patient suspected of, or already suffering from such a disease in an amount sufficient to cure, or at least partially arrest, the symptoms of the disease and its complications. An amount adequate to accomplish this is referred to as a therapeutically- or pharmaceutically-effective dose or amount. In both prophylactic and therapeutic regimes an antibody or antibody-drug conjugate is usually administered in several dosages until a sufficient response (e.g., triggering of appropriate NK cell activity or inhibition of inappropriate NK cell activity) has been achieved. Typically, the response is monitored and repeated dosages are given if the desired response starts to fade.

For variations of the present invention where the use is diagnostic or screening for elevated risk in a subject not yet suffering from disease or disorder mediated by NKp30-expressing cells or characterized by the presence of B7H6-expressing cells, a biological sample is taken from the subject and compared to a biological sample from normal or healthy subjects or a predetermined base level. The risk of developing cancer is determined by detection of a higher level in the subject sample than found in the comparable biological sample from normal or healthy subjects or base level. Methods of detecting the antibodies compositions of the present invention are described in Section V.C.

The compositions and methods of the present invention can be used to monitor progress of therapy in a biological sample from a subject at various times after bone marrow transplantation or at various times of having been given an anti-cancer drug or a therapy. B7H6 level detected in a biological sample from a subject is detected as prior to treatment (T1) and compared to a biological sample from the same subject taken at a second time (T2); after treatment. A higher level of B7H6 generally indicates progression of disease and lower of B7H6 indicates regression.

To identify subject patients for screening or treatment according to the methods of the invention, accepted screening methods may be employed to determine risk factors associated with specific diseases or disorders mediated by NKp30-expressing cells or characterized by the presence of B7H6-expressing cells, or to determine the status of an existing disorder identified in a subject. Such methods can include, for example, determining whether an individual has relatives who have been diagnosed with a particular disease. Screening methods can also include, for example, conventional work-ups to determine familial status for a particular disease known to have a heritable component (for example, in the case of BMT, clinical studies have shown that the presence of certain HLA-C alleles correlates with an increased risk for BM allograft rejection (see Scott et al., *Blood* 92:4864-4871, 1998) and various cancers are also known to have certain inheritable components). Inheritable components of cancers include, for example, mutations in multiple genes that are transforming (e.g., Ras, Raf, EGFR, cMet and others), the presence or absence of certain HLA and killer inhibitory receptor (KIR) molecules, or mechanisms by which cancer cells are able to modulate immune suppression of cells like NK cells and T cells, either directly or indirectly (see, e.g., Ljunggren and Malmberg, *Nature Rev. Immunol.* 7:329-339, 2007; Boyton and Altmann, *Clin. Exp. Immunol.* 149:1-8, 2007). Toward this end, nucleotide probes can be routinely employed to identify individuals carrying genetic markers associated with a particular disease of interest. In addition, a wide variety of immunological methods are known in the art that are useful to identify markers for specific diseases. For example, various ELISA immunoassay methods are available and well-known in the art that employ monoclonal antibody probes to detect antigens associated with specific tumors. Screening may be implemented as indicated by known patient symptomology, age factors, related risk factors, etc. These methods allow the clinician to routinely select patients in need of the methods described herein for treatment. In accordance with these methods, modulation of NK cell activity may be implemented as an independent treatment program or as a follow-up, adjunct or coordinate treatment regimen to other treatments.

B. Cancer Treatment

1. Types of Cancer

As described and shown by studies herein, a B7H6 antibody may be used to direct killing of a B7H6-expressing cell by activating the ADCC or CDC pathway through binding of Fc to Fc receptors and the complement protein, C1q. In yet other variations, an anti-human-B7H6 monoclonal antibody-drug conjugate, comprising a cytotoxic agent conjugated to an anti-human-B7H6 monoclonal antibody, may be used to deliver a cytotoxic agent to B7H6-expressing cancer cells, where the cytotoxic agent exerts a therapeutic effect by depleting or inhibition the growth of the cancer cells.

Table 4 below lists some cancers amenable to treatment in accordance with the present invention, organized predominantly by target.

TABLE 4

List of Exemplary Cancer Types

1. Head and Neck cancer
   a. Brain
   b. Oral cavity

TABLE 4-continued

List of Exemplary Cancer Types c. Orophyarynx
    d. Nasopharynx
    e. Hypopharynx
    f. Nasal cavities and paranasal sinuses
    g. Larynx
    h. Lip
2. Lung cancers
    a. Non-small cell carcinoma
    b. Small cell carcinoma
3. Gastrointestinal Tract cancers
    a. Colorectal cancer
    b. Gastric cancer
    c. Esophageal cancer
    d. Anal cancer
    e. Extrahepatic Bile Duct cancer
    f. Cancer of the Ampulla of Vater
    g. Gastrointestinal Stromal Tumor (GIST)
4. Liver cancer
    a. Liver Cell Adenoma
    b. Hepatocellular Carcinoma
5. Breast cancer
6. Gynecologic cancer
    a. Cervical cancer
    b. Ovarian cancer
    c. Vaginal cancer
    d. Vulvar cancer
    e. Gestational Trophoblastic Neoplasia
    f. Uterine cancer
7. Urinary Tract cancer
    a. Renal cancer carcinoma
    b. Prostate cancer
    c. Urinary Bladder cancer
    d. Penile cancer
    e. Urethral cancer
8. Urinary Bladder cancer
9. Neurological Tumors
    a. Astrocytoma and glioblastoma
    b. Primary CNS lymphoma
    c. Medulloblastoma
    d. Germ Cell tumors
    e. Retinoblastoma
10. Endocrine Neoplasms
    a. Thyroid cancer
    b. Pancreatic cancer
        1) Islet Cell tumors
            a) Insulinomas
            b) Glucagonomas
    c. Pheochromocytoma
    d. Adrenal carcinoma
    e. Carcinoid tumors
    f. Parathyroid carcinoma
    g. Pineal gland neoplasms
11. Skin cancers
    a. Malignant melanoma
    b. Squamous Cell carcinoma
    c. Basal Cell carcinoma
    d. Kaposi's Sarcoma
12. Bone cancers
    a. Osteoblastoma
    b. Osteochondroma
    c. Osteosarcoma
13. Connective Tissue neoplasms
    a. Chondroblastoma
    b. Chondroma
14. Hematopoietic malignancies
    a. Non-Hodgkin Lymphoma
        1) B-cell lymphoma
        2) T-cell lymphoma
        3) Undifferentiated lymphoma
    b. Leukemias
        1) Chronic Myelogenous Leukemia
        2) Hairy Cell Leukemia
        3) Chronic Lymphocytic Leukemia
        4) Chronic Myelomonocytic Leukemia
        5) Acute Myelocytic Leukemia
        6) Acute Lymphoblastic Leukemia
    c. Myeloproliferative Disorders
        1) Multiple Myeloma
        2) Essential Thrombocythemia
        3) Myelofibrosis with Myeloid Metaplasia
        4) Hypereosinophilic Syndrome
        5) Chronic Eosinophilic Leukemia
        6) Polycythemia Vera
    d. Hodgkin Lymphoma
15. Childhood Cancers
    a. Leukemia and Lymphomas
    b. Brain cancers
    c. Neuroblastoma
    d. Wilm's Tumor (nephroblastoma)
    e. Phabdomyosarcoma
    f. Retinoblastoma
16. Immunotherapeutically sensitive cancers
    a. melanoma
    b. kidney cancer
    c. leukemias, lymphomas and myelomas
    d. breast cancer
    e. prostate cancer
    f. colorectal cancer
    g. cervical cancer
    h. ovarian cancer
    i. lung cancer Some of the cancers listed above, including some of the relevant animal models for evaluating the effects of an anti-B7H6 antibody or antibody-drug conjugate in accordance with the present invention on tumor responses, are discussed in further detail below.

a. Chronic Myeloid Leukemia

Chronic myeloid leukemia (CML) is a rare type of cancer affecting mostly adults. It is a cancer of granulocytes (a predominant type of white blood cell). In CML many granulocytes are produced and released into the blood when they are immature and unable to function properly. The immature white blood cells are known as blasts. The production of other types of blood cells is also disrupted. Normally, white blood cells repair and reproduce themselves in an orderly and controlled manner, but in chronic myeloid leukemia the process is uncontrolled and cells continue to divide and mature abnormally. The disease usually develops very slowly, and considered chronic myeloid leukemia.

Because CML progresses slowly, it is difficult to detect in its early stages. Sometimes it is discovered only when a blood test is done for another reason. The symptoms of CML are often vague, non-specific and caused by the increased number of abnormal white blood cells in the bone marrow and the reduced number of normal blood cells, resulting in a feeling of fullness or a tender lump on the left side of the abdomen. In CML, the spleen can become enlarged. The swelling of the spleen may also cause pressure on the stomach, leading to indigestion and poor appetite resulting in anemia. Due to a lower number of platelets in the blood some people may notice that they bleed or bruise more easily. "Petechiae" associated with CML, is a special type of bruising, where small blood-like spots usually seen on the legs or in the mouth. Women may find that their periods become very much heavier. However, these symptoms and signs are rare. Chronic myeloid leukemia can occur at any age, but it more commonly affects middle-aged and older people and is rare in children (National Cancer Institute, "NIH Publication No. 08-3775" Rockville, Md., September 2008). The effects of an anti-human-B7H6 monoclonal antibody or antibody-drug conjugate on tumor response can be evaluated, for example, in a human tumor xenograft model, using human CML cells engrafted in immunodeficient mice (see, e.g., Ren, *Leukemia* and *Lymphoma* 8:1549-1561, 2002; Van Etten, *Blood Cells Mol. Dis.* 27:201-205, 2001; Wong and Witte, *Oncogene* 20:5644-5659, 2001).

b. Multiple Myeloma

Multiple myeloma is a type of cancer affecting certain white blood cells called plasma cells. In cancer involving plasma cells, the cells are all abnormal and identical and called myeloma cells. Myeloma cells tend to collect in the bone marrow and in the hard, outer part of bones. Sometimes they collect in only one bone and form a single mass, or tumor, called a plasmacytoma. In most cases, however, the myeloma cells collect in many bones, often forming many tumors and causing other problems. When this happens, the disease is called multiple myeloma.

Because people with multiple myeloma have an abnormally large number of identical plasma cells, they also have too much of one type of antibody. These myeloma cells and antibodies can cause a number of serious medical problems which can include: (1) As myeloma cells increase in number, they damage and weaken bones, causing pain and sometimes fractures. (2) When bones are damaged, calcium is released into the blood. This may lead to hypercalcemia. Hypercalcemia can cause loss of appetite, nausea, thirst, fatigue, muscle weakness, restlessness, and confusion. (3) Myeloma cells prevent the bone marrow from forming normal plasma cells and other white blood cells important to the immune system. Patients may be more susceptible to infection and disease. (4) The cancer cells also may prevent the growth of new red blood cells, causing anemia. (5) Multiple myeloma patients may have serious problems with their kidneys. Excess antibody proteins and calcium can prevent the kidneys from filtering and cleaning the blood properly. Symptoms depend on how advanced the disease is. In the earliest stage of the disease, there may be no symptoms. When symptoms do occur, patients commonly have bone pain, often in the back or ribs. Patients also may have broken bones, weakness, fatigue, weight loss, or repeated infections. When the disease is advanced, symptoms may include nausea, vomiting, constipation, problems with urination, and weakness or numbness in the legs (National Cancer Institute, "NIH Publication No. 08-1575" Rockville, Md., September 2008). The effects of an anti-B7H6 antibody or antibody-drug conjugate on tumor response can be evaluated in a human tumor xenograft model in immunodeficient mice, such as described in Miyakawa et al., *Biochem. Biophys. Res. Commun.* 313:258-62, 2004.

c. Non-Hodgkin's Lymphoma

There are two main types of lymphoma. Hodgkin's disease and non-Hodgkin's lymphoma. There are about 20 different types of non-Hodgkin's lymphoma. In most cases of Hodgkin's disease, a particular cell known as the Reed-Sternberg cell is found in the biopsies. This cell is not usually found in other lymphomas, and results in different treatment for Hodgkin's and non-Hodgkin's lymphomas.

Often, the first sign of a non-Hodgkin's lymphoma is a painless swelling of a lymph node in the neck, armpit or groin. Other symptoms may include any of the following: night sweats or unexplained fever; loss of appetite, unexplained weight loss and excessive tiredness; children may develop a cough or breathlessness. Patients may complain of abdominal pain, or a lump in a child's abdomen or persistent itching of the skin all over the body (National Cancer Institute, "NIH Publication No. 07-1567" Rockville, Md., September 2007). The effects of an anti-human-B7H6 monoclonal antibody or antibody-drug conjugate on tumor response can be evaluated in a non-Hodgkin's lymphoma xenograft model similar to that described in Ansell et al., *Leukemia* 18:616-23, 2004.

The classification of Non-Hodgkin's lymphomas most commonly used is the REAL classification system (Ottensmeier, *Chemico-Biological Interactions* 135-136:653-664, 2001.) Specific immunological markers have been identified for classifications of lymphomas. For example, follicular lymphoma markers include CD20+, CD3−, CD10+, CD5−; small lymphocytic lymphoma markers include CD20+, CD3−, CD10−, CD5+, CD23+; marginal zone B cell lymphoma markers include CD20+, CD3−, CD10−, CD23−; diffuse large B cell lymphoma markers include CD20+, CD3−; mantle cell lymphoma markers include CD20+, CD3−, CD10−, CD5+, CD23+; peripheral T cell lymphoma markers include CD20−, CD3+; primary mediastinal large B cell lymphoma markers include CD20+, CD3−, lymphoblastic lymphoma markers include CD20−, CD3+, Tdt+, and Burkitt's lymphoma markers include CD20+, CD3−, CD10+, CD5− (Decision Resources, Non-Hodgkins Lymphoma, Waltham, Mass., February 2002).

Clinical classification of Non Hodgkins lymphoma (NHL) by the International Working Formulation breaks down disease into subtypes: (1) low grade (indolent) disease which includes small lymphocytic, consistent with chronic lymphocytic leukemia (SC); follicular, predominantly small cleaved cell (FSC); follicular, mixed small cleaved and large cell (FM); (2) intermediate grade disease which includes follicular, predominantly large cell (FL); diffuse, small cleaved cell (DSC); diffuse mixed, small and large cell (DM); diffuse, large cleaved or noncleaved cell (DL); and (3) high grade disease which includes immunoblastic, large cell (IBL); lymphoblastic, convoluted or nonconvoluted cell (LL); and small noncleaved cell, Burkitt's or non-Burkitts (SNC; The Non-Hodgkin's Lymphoma Pathologic Classification Project, *Cancer* 49:2112-35, 1982). The Ann Arbor Staging system is commonly used to stage patients with NHL. Stage I means involvement of a single lymph node region or localized involvement of a single extralymphatic organ or site. Stage 11 means involvement of two or more lymph node regions on the same side of the diaphragm or localized involvement of an extranoldal site or organ and one or more lymph node regions on the same side of the diaphragm. Stage III means involvement of lymph node regions on both sides of the diaphragm, possibly accompanied by localized involvement of an extranodal organ or site. Stage IV means diffuse or disseminated involvement of one or more distant extranodal organs with or without associated lymph node involvement ("Lymphoid neoplasms," In *American Joint Committee on Cancer.: AJCC Cancer Staging Manual* 6th ed. New York, N.Y.: Springer, 2002, pp. 393-406). Rituximab has been shown effective in treating indolent and follicular lymphomas (Boge et al., *Annals of Oncol.* 14:520-535, 2003).

d. Cervical Cancer

The cervix is the neck of the uterus that opens into the vagina. Cervical cancer, also called cervical carcinoma, develops from abnormal cells on the surface of the cervix and is one of the most common cancers affecting women. Cervical cancer is usually preceded by dysplasia, precancerous changes in the cells on the surface of the cervix. These abnormal cells can progress to invasive cancer. Once the cancer appears it can progress through four stages. The stages are defined by the extent of spread of the cancer. The more the cancer has spread, the more extensive the treatment is likely to be. There are 2 main types of cervical cancer: (1) Squamous type (epidermoid cancer): This is the most common type, accounting for about 80% to 85% of cervical cancers. This cancer may be caused by sexually transmitted diseases. One such sexual disease is the human papillomavirus, which causes venereal warts. The cancerous tumor grows on and into the cervix. The cancer generally starts on the surface of the cervix and may be diagnosed at an early stage by a Pap smear. (2) Adenocarcinoma: This type of cervical cancer develops from the tissue in the cervical glands in the canal of the cervix. Early disease usually causes no symptoms. The cancer can usually be detected by a Pap smear and pelvic exam. Later stages of disease cause abnormal vaginal bleeding or a bloodstained discharge at unexpected times, such as between menstrual periods, after intercourse, or after menopause. Abnormal vaginal discharge may be cloudy or bloody or may contain mucus with a bad odor. Advanced stages of the cancer may cause pain (National Cancer Institute, "NIH Publication No. 08-2407" Rockville, Md., September 2008). The effects of an anti-human-B7H6 monoclonal antibody or antibody-drug conjugate on tumor response can be evaluated in a human tumor xenograft model similar to that described in Downs et al., *Gynecol. Oncol.* 98:203-10, 2005; and Li et al., *Int. J. Gynecol. Cancer* 15:301-7, 2005.

e. Head and Neck Tumors

Most cancers of the head and neck are of a type called carcinoma (in particular squamous cell carcinoma). Carcinomas of the head and neck start in the cells that form the lining of the mouth, nose, throat or ear, or the surface layer covering the tongue. However, cancers of the head and neck can develop from other types of cells. Lymphoma develops from the cells of the lymphatic system. Sarcoma develops from the supportive cells which make up muscles, cartilage or blood vessels. Melanoma starts from cells called melanocytes, which give colour to the eyes and skin. The symptoms of a head and neck cancer will depend on where it is—for example, cancer of the tongue may cause some slurring of speech. The most common symptoms are an ulcer or sore area in the head or neck that does not heal within a few weeks; difficulty in swallowing, or pain when chewing or swallowing; trouble with breathing or speaking, such as persistent noisy breathing, slurred speech or a hoarse voice; a numb feeling in the mouth; a persistent blocked nose, or nose bleeds; persistent earache, ringing in the ear, or difficulty in hearing; a swelling or lump in the mouth or neck; pain in the face or upper jaw; in people who smoke or chew tobacco, pre-cancerous changes can occur in the lining of the mouth, or on the tongue. These can appear as persistent white patches (leukoplakia) or red patches (erythroplakia). They are usually painless but can sometimes be sore and may bleed (National Cancer Institute, "NIH Publication No. 09-1574" Rockville, Md., September 2009). The effects of an anti-human-B7H6 monoclonal antibody or antibody-drug conjugate on tumor response can be evaluated in a human head and neck tumor xenograft model similar to that described in Kuriakose et al., *Head Neck* 22:57-63, 2000; Cao et al., *Clin. Cancer Res.* 5:1925-34, 1999; Braakhuis et al., *Cancer Res.* 51:211-4, 1991; and Baker, *Laryngoscope* 95:43-56, 1985.

f. Brain Cancer

Tumors that begin in brain tissue are known as primary tumors of the brain and are named according to the type of cells or the part of the brain in which they begin. The most common primary brain tumors begin in glial cells, called gliomas. There are many types of gliomas: (1) Astrocytoma—The tumor arises from star-shaped glial cells called astrocytes. In adults, astrocytomas most often arise in the cerebrum. In children, they occur in the brain stem, the cerebrum, and the cerebellum. A grade III astrocytoma is sometimes called an anaplastic astrocytoma. A grade IV astrocytoma is usually called a glioblastoma multiforme. (2) Brain stem glioma—The tumor occurs in the lowest part of the brain. Brain stem gliomas most often are diagnosed in young children and middle-aged adults. (3) Ependymoma—The tumor arises from cells that line the ventricles or the central canal of the spinal cord, and they are most commonly found in children and young adults. (4) Oligodendroglioma—This rare tumor arises from cells that make the fatty substance that covers and protects nerves. These tumors usually occur in the cerebrum. They grow slowly and usually do not spread into surrounding brain tissue. They are most common in middle-aged adults. The symptoms of brain tumors depend on tumor size, type, and location. Symptoms may be caused when a tumor presses on a nerve or damages a certain area of the brain. They also may be caused when the brain swells or fluid builds up within the skull. The most common symptoms of brain tumors include headaches (usually worse in the morning); nausea or vomiting; changes in speech, vision, or hearing; problems balancing or walking; changes in mood, personality, or ability to concentrate; problems with memory; muscle jerking or twitching (seizures or convulsions); and numbness or tingling in the arms or legs (National Cancer Institute, "NIH Publication No. 09-1558" Rockville, Md., May 2009). The effects of an anti-human-B7H6 monoclonal antibody or antibody-drug conjugate on tumor response can be evaluated in a human glioma xenograft model similar to that described in Bello et al., *Clin. Cancer Res.* 8:3539-48, 2002.

g. Thyroid Cancer

Papillary and follicular thyroid cancers account for 80 to 90 percent of all thyroid cancers. Both types begin in the follicular cells of the thyroid. Most papillary and follicular thyroid cancers tend to grow slowly. If they are detected early, most can be treated successfully. Medullary thyroid cancer accounts for 5 to 10 percent of thyroid cancer cases, and it arises in C cells, not follicular cells. Anaplastic thyroid cancer is the least common type of thyroid cancer (only 1 to 2 percent of cases), and it arises in the follicular cells. The cancer cells are highly abnormal and difficult to recognize. This type of cancer is usually very hard to control because the cancer cells tend to grow and spread very quickly. Early thyroid cancer often does not cause symptoms. But as the cancer grows, symptoms may include: a lump, or nodule, in the front of the neck near the Adam's apple; hoarseness or difficulty speaking in a normal voice; swollen lymph nodes, especially in the neck; difficulty swallowing or breathing; or pain in the throat or neck (National Cancer Institute, "NIH Publication No. 07-4994" Rockville, Md., September 2007). The effects of an anti-human-B7H6 monoclonal antibody or antibody-drug conjugate on tumor response can be evaluated in a human tumor xenograft model similar to that described in Quidville et al., *Endocrinology* 145:2561-71, 2004.

h. Liver Cancer

There are two different types of primary liver cancer. The most common kind is called hepatoma or hepatocellular carcinoma (HCC), and arises from the main cells of the liver (the hepatocytes). This type is usually confined to the liver, although occasionally it spreads to other organs. There is also a rarer and unrelated sub-type of hepatoma called Fibrolamellar hepatoma, which may occur in younger people. The other type of primary liver cancer starts in cells of the bile ducts is called cholangiocarcinoma or bile duct cancer. Most people who develop hepatoma usually also have a condition called cirrhosis of the liver. This is a fine scarring throughout the liver which is due to a variety of causes including infection and heavy alcohol drinking over a long period of time. However, only a small proportion of people who have cirrhosis of the liver develop primary liver cancer. Infection with either the hepatitis B or hepatitis C virus can lead to liver cancer, and can cause cirrhosis, which increases the risk of developing hepatoma. People who have a rare condition called haemochromatosis, which causes excess deposits of iron in the body, have a higher chance of developing hepatoma. An anti-human-B7H6 monoclonal antibody or antibody-drug conjugate may be used to treat, prevent, inhibit the progression of, delay the onset of, and/or reduce the severity or inhibit at least one of the conditions or symptoms associated with hepatocellular carcinoma. The hepatocellular carcinoma may or may not be associated with a hepatitis (e.g., hepatitis A, hepatitis B, hepatitis C and hepatitis D) infection. The effects of an anti-human-B7H6 monoclonal antibody or antibody-drug conjugate on tumor response can be evaluated in a human tumor xenograft model similar to that described in Zhou et al., *Clin. Cancer Res.* 9:6030-7, 2003; and Huynh et al., *J. Cell Mol. Med.* 2008 (E-Publication 10.1111/j.1582-4934.2008.00364., 2008, Blackwell Synergy).

i. Lung Cancer

The effects of an anti-human-B7H6 monoclonal antibody or antibody-drug conjugate on tumor response can be evaluated in a human small/non-small cell lung carcinoma xenograft model. Briefly, human tumors are grafted into immunodeficient mice and these mice are treated with an anti-human-B7H6 monoclonal antibody or antibody-drug conjugate, alone or in combination with other agents. Efficacy of the treatment can be demonstrated by evaluating tumor growth (Nemati et al., *Clin Cancer Res.* 6:2075-86, 2000; and Hu et al., *Clin. Cancer Res.* 10:7662-70, 2004).

2. Endpoints and Anti-Tumor Activity for Solid Tumors

While each protocol may define tumor response assessments differently, the RECIST (Response evaluation Criteria in solid tumors) criteria is currently considered to be the recommended guideline for assessment of tumor response by the National Cancer Institute (see Therasse et al., *J. Natl. Cancer Inst.* 92:205-216, 2000). According to the RECIST criteria, tumor response means a reduction or elimination of all measurable lesions or metastases. Disease is generally considered measurable if it comprises lesions that can be accurately measured in at least one dimension as ≥20 mm with conventional techniques or ≥10 mm with spiral CT scan with clearly defined margins by medical photograph or X-ray, computerized axial tomography (CT), magnetic resonance imaging (MRI), or clinical examination (if lesions are superficial). Non-measurable disease means the disease comprises of lesions <20 mm with conventional techniques or <10 mm with spiral CT scan, and truly non-measurable lesions (too small to accurately measure). Non-measurable disease includes pleural effusions, ascites, and disease documented by indirect evidence.

The criteria for objective status are required for protocols to assess solid tumor response. Representative criteria include the following: (1) Complete Response (CR), defined as complete disappearance of all measurable disease; no new lesions; no disease related symptoms; no evidence of non-measurable disease; (2) Partial Response (PR) defined as 30% decrease in the sum of the longest diameter of target lesions; (3) Progressive Disease (PD), defined as 20% increase in the sum of the longest diameter of target lesions or appearance of any new lesion; (4) Stable or No Response, defined as not qualifying for CR, PR, or PD. (See Therasse et al., supra.)

Additional endpoints that are accepted within the oncology art include overall survival (OS), disease-free survival (DFS), objective response rate (ORR), time to progression (TTP), and progression-free survival (PFS) (see *Guidance for Industry: Clinical Trial Endpoints for the Approval of Cancer Drugs and Biologics*, April 2005, Center for Drug Evaluation and Research, FDA, Rockville, Md.)

3. Combination Cancer Therapy

As previously discussed, in certain embodiments, an anti-human-B7H6 monoclonal antibody or antibody-drug conjugate is used in combination with a second agent for treatment of a disease or disorder. When used for treating cancer, an anti-human-B7H6 monoclonal antibody or antibody-drug conjugate of the present invention may be used in combination with conventional cancer therapies such as, e.g., surgery, radiotherapy, chemotherapy, or combinations thereof. In certain aspects, other therapeutic agents useful for combination cancer therapy with an anti-B7H6 antibody or antibody-drug conjugate in accordance with the present invention include anti-angiogenic agents. In some other aspects, other therapeutic agents useful for combination therapy include an antagonist of certain factors that are involved in tumor growth such as, for example, EGFR, ErbB2 (Her2), ErbB3, ErbB4, or TNF. In some aspects, an antibody or antibody-drug conjugate in accordance with the present invention is co-administered with a cytokine (e.g., a cytokine that stimulates an immune response against a tumor). Exemplary combination therapies particularly amenable for treatment of cancer are described in further detail below.

a. Antibodies Targeting Tumor-Associated Antigens

As previously noted, antibody therapy has been particularly successful in cancer treatment because certain tumors either display unique antigens, lineage-specific antigens, or antigens present in excess amounts relative to normal cells. One of the mechanisms associated with the anti-tumor activity of monoclonal antibody therapy is antibody dependent cellular cytotoxicity (ADCC). In ADCC, monoclonal antibodies bind to a target cell (e.g., cancer cell) and specific effector cells expressing receptors for the monoclonal antibody (e.g., NK cells, monocytes, granulocytes) bind the monoclonal antibody/target cell complex resulting in target cell death. Accordingly, in certain variations of the present invention, an anti-human-B7H6 monoclonal antibody or antibody-drug conjugate having efficacy against a cancer is co-administered with a monoclonal antibody against a second tumor-associated antigen (i.e., a tumor-associated antigen other than B7H6). The dose and schedule of the MAbs is based on pharmacokinetic and toxicokinetic properties ascribed to the specific antibody co-administered, and should optimize these effects, while minimizing any toxicity that may be associated with administration of an anti-human-B7H6 monoclonal antibody or antibody-drug conjugate.

Combination therapy with an anti-B7H6 monoclonal antibody or antibody-drug conjugate as described herein and a second monoclonal antibody against a tumor-associated antigen may be indicated when a first line treatment has failed and may be considered as a second line treatment. The present invention also provides using the combination as a first line treatment in patient populations that are newly diagnosed and have not been previously treated with anticancer agents ("de novo patients") and patients that have not previously received any monoclonal antibody therapy ("naïve patients").

An anti-B7H6 antibody or antibody-drug conjugate as described herein is also useful in combination therapy with monoclonal antibodies against tumor-associated antigens in the absence of any direct antibody-mediated ADCC or CDC of tumor cells. For example, antibodies that block an inhibitory signal in the immune system can lead to augmented immune responses. Examples include (1) antibodies against molecules of the B7R family that have inhibitory function such as, cytotoxic T lymphocyte-associated antigen 4 (CTLA-4), programmed death-1 (PD-1), B and T lymphocyte attenuator (BTLA); (2) antibodies against inhibitory cytokines like IL-10, TGFβ; and (3) antibodies that deplete or inhibit functions of suppressive cells like anti-CD25 or CTLA-4. For example, anti-CTLA4 MAbs in both mice and humans are thought to either suppress function of immune-suppressive regulatory T cells (Tregs) or inhibit the inhibitory signal transmitted through binding of CTLA-4 on T cells to B7-1 or B7-2 molecules on APCs or tumor cells.

Table 6 is a non-exclusive list of monoclonal antibodies approved or being tested for which combination therapy in accordance with the present invention is possible.

TABLE 6

Monoclonal Antibody Therapies for Use in Combination with Anti-B7H6 Antibodies or Antibody-drug Conjugates

| Target | Drug Name | Clinical Indication | Company |
|---|---|---|---|
| TRAIL-R1 | HGS-ETR1 | Cancers | HGS |
| TRAIL-R2 | HGS-ETR2 | solid tumors | HGS |
| CD40 | SGN40 | MM | Seattle Genetics |
| HER2 | Herceptin | Breast cancer | Genentech |
| EGF-R | ABX-EGF | CRC, NSCLC, RCC | Abgenix |
| EGF-R | EMD72000 | solid tumors | Merck |
| EGF-R | MDX-214 | EGF-R-positive tumors | Medarex |
| EGF-R | Erbitux | CRC | Imclone |
| α5β3 integrin | Vitaxin | psoriasis, prostate cancer | AME/Lilly |
| CD152 | CTLA-4 | Cancers | Medarex |
| CD49e | Integrin α5 | Cancers | Protein Design Labs |
| MUC18 (TIM-like) | ABX-MA1 | Melanoma | |
| TAG-72 Mucin | Anatumomab | Cancers | |
| CD3 | Ecromeximab | Melanoma | Kyowa Hakko |
| CD64 (Fc GR1) | AntiCD64 | Cancers | Medarex |
| CEA | CEA-Cide | Cancers | Immunomedics |
| EpCAM | Panorex | colorectal cancer | Centocor |
| Lewis-Y-Ag | SGN15 | Cancers | Seattle Genetics | b. Tyrosine Kinase Inhibitors

In some embodiments, an anti-human-B7H6 monoclonal antibody or antibody-drug conjugate as described herein is used in combination with a tyrosine kinase inhibitor. Tyrosine kinases are enzymes that catalyze the transfer of the γ phosphate group from the adenosine triphosphate to target proteins. Tyrosine kinases can be classified as receptor and non-receptor protein tyrosine kinases. They play an essential role in diverse normal cellular processes, including activation through growth receptors and affect proliferation, survival and growth of various cell types. Additionally, they are thought to promote tumor cell proliferation, induce anti-apoptotic effects and promote angiogenesis and metastasis. In addition to activation through growth factors, protein kinase activation through somatic mutation is a common mechanism of tumorigenesis. Some of the mutations identified are in B-Raf kinase, FLt3 kinase, BCR-ABL kinase, c-KIT kinase, epidermal growth factor (EGFR) and PDGFR pathways. The Her2, VEGFR and c-Met are other significant receptor tyrosine kinase (RTK) pathways implicated in cancer progression and tumorigenesis. Because a large number of cellular processes are initiated by tyrosine kinases, they have been identified as key targets for inhibitors.

Tyrosine kinase inhibitors (TKIs) are small molecules that act inside the cell, competing with adenosine triphosphate (ATP) for binding to the catalytic tyrosine kinase domain of both receptor and non-receptor tyrosine kinases. This competitive binding blocks initiation of downstream signaling leading to effector functions associated with these signaling events like growth, survival, and angiogenesis. Using a structure and computational approach, a number of compounds from numerous medicinal chemistry combinatorial libraries was identified that inhibit tyrosine kinases.

Most TKIs are thought to inhibit growth of tumors through direct inhibition of the tumor cell or through inhibition of angiogenesis. Moreover, certain TKIs affect signaling through the VEGF family receptors, including sorafenib and sunitinib. In some cases TKIs have been shown to activate functions of dendritic cells and other innate immune cells, like NK cells. This has been recently reported in animal models for imatinib. Imatinib is a TKI that has shown to enhance killer activity by dendritic cells and NK cells (for review, see Smyth et al., *NEJM* 354:2282, 2006).

BAY 43-9006 (sorafenib, Nexavar®) and SU11248 (sunitinib, Sutent®) are two such TKIs that have been recently approved for use in metastatic renal cell carcinoma (RCC). A number of other TKIs are in late and early stage development for treatment of various types of cancer. Other TKIs include, but are not limited to: Imatinib mesylate (Gleevec®, Novartis); Gefitinib (Iressa®, AstraZeneca); Erlotinib hydrochloride (Tarceva®, Genentech); Vandetanib (Zactima®, AstraZeneca), Tipifarnib (Zarnestra®, Janssen-Cilag); Dasatinib (Sprycel®, Bristol Myers Squibb); Lonafarnib (Sarasar®, Schering Plough); Vatalanib succinate (Novartis, Schering AG); Lapatinib (Tykerb®, GlaxoSmithKline); Nilotinib (Novartis); Lestaurtinib (Cephalon); Pazopanib hydrochloride (GlaxoSmithKline); Axitinib (Pfizer); Canertinib dihydrochloride (Pfizer); Pelitinib (National Cancer Institute, Wyeth); Tandutinib (Millennium); Bosutinib (Wyeth); Semaxanib (Sugen, Taiho); AZD-2171 (AstraZeneca); VX-680 (Merck, Vertex); EXEL-0999 (Exelixis); ARRY-142886 (Array BioPharma, AstraZeneca); PD-0325901 (Pfizer); AMG-706 (Amgen); BIBF-1120 (Boehringer Ingelheim); SU-6668 (Taiho); CP-547632 (OSI); (AEE-788 (Novartis); BMS-582664 (Bristol-Myers Squibb); JNK-401 (Celgene); R-788 (Rigel); AZD-1152 HQPA (AstraZeneca); NM-3 (Genzyme Oncology); CP-868596 (Pfizer); BMS-599626 (Bristol-Myers Squibb); PTC-299 (PTC Therapeutics); ABT-869 (Abbott); EXEL-2880 (Exelixis); AG-024322 (Pfizer); XL-820 (Exelixis); OSI-930 (OSI); XL-184 (Exelixis); KRN-951 (Kirin Brewery); CP-724714 (OSI); E-7080 (Eisai); HKI-272 (Wyeth); CHIR-258 (Chiron); ZK-304709 (Schering AG); EXEL-7647 (Exelixis); BAY-57-9352 (Bayer); BIBW-2992 (Boehringer Ingelheim); AV-412 (AVEO); YN-968D1 (Advenchen Laboratories); Midostaurin (Novartis); Perifosine (AEterna Zentaris, Keryx, National Cancer Institute); AG-024322 (Pfizer); AZD-1152 (AstraZeneca); ON-01910Na (Onconova); and AZD-0530 (AstraZeneca).

c. Chemotherapy Combinations

In certain embodiments, an anti-human-B7H6 monoclonal antibody or antibody-drug conjugate is administered in combination with one or more chemotherapeutic agents. Chemotherapeutic agents have different modes of actions, for example, by influencing either DNA or RNA and interfering with cell cycle replication. Examples of chemotherapeutic agents that act at the DNA level or on the RNA level are anti-metabolites (such as Azathioprine, Cytarabine, Fludarabine phosphate, Fludarabine, Gemcitabine, cytarabine, Cladribine, capecitabine 6-mercaptopurine, 6-thioguanine, methotrexate, 5-fluoroouracil and hyroxyurea; alkylating agents (such as Melphalan, Busulfan, Cis-platin, Carboplatin, Cyclophosphamide, Ifosphamide, Dacarabazine, Procarbazine, Chlorambucil, Thiotepa, Lomustine, Temozolamide); anti-mitotic agents (such as Vinorelbine, Vincristine, Vinblastine, Docetaxel, Paclitaxel); topoisomerase inhibitors (such as Doxorubincin, Amsacrine, Irinotecan, Daunorubicin, Epirubicin, Mitomycin, Mitoxantrone, Idarubicin, Teniposide, Etoposide, Topotecan); antibiotics (such as actinomycin and bleomycin); asparaginase; anthracyclines or taxanes.

d. Radiotherapy Combinations

In some variations, an anti-human-B7H6 monoclonal antibody or antibody-drug conjugate is administered in combination with radiotherapy. Certain tumors can be treated with radiation or radiopharmaceuticals. Radiation therapy is generally used to treat unresectable or inoperable tumors and/or tumor metastases. Radiotherapy is typically delivered in three ways. External beam irradiation is administered at distance from the body and includes gamma rays ($^{60}$Co) and X-rays. Brachytherapy uses sources, for example $^{60}$Co, $^{137}$Cs, $^{192}$Ir, or $^{125}$I, with or in contact with a target tissue.

e. Hormonal Agent Combinations

In some embodiments, an anti-human-B7H6 monoclonal antibody or antibody-drug conjugate is administered in combination with a hormone or anti-hormone. Certain cancers are associated with hormonal dependency and include, for example, ovarian cancer, breast cancer, and prostate cancer. Hormonal-dependent cancer treatment may comprise use of anti-androgen or anti-estrogen compounds. Hormones and anti-hormones used in cancer therapy include Estramustine phosphate, Polyestradiol phosphate, Estradiol, Anastrozole, Exemestane, Letrozole, Tamoxifen, Megestrol acetate, Medroxyprogesterone acetate, Octreotide, Cyproterone acetate, Bicaltumide, Flutamide, Tritorelin, Leuprorelin, Buserelin and Goserelin.

For administration, the anti-human-B7H6 monoclonal antibody or antibody-drug conjugate is formulated as a pharmaceutical composition. A pharmaceutical composition comprising an anti-human-B7H6 monoclonal antibody or antibody-drug conjugate can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), *Remington Pharmaceutical Sciences* (Mack Publishing Company, 19th ed. 1995).) Formulations may further include one or more excipients, preservatives, solubilizers, buffering agents, albumin to prevent protein loss on vial surfaces, etc.

A pharmaceutical composition comprising an anti-human-B7H6 monoclonal antibody or antibody-drug conjugate is administered to a subject in an effective amount. According to the methods of the present invention, the antibody or antibody-drug conjugate may be administered to subjects by a variety of administration modes, including, for example, by intramuscular, subcutaneous, intravenous, intra-atrial, intra-articular, parenteral, intranasal, intrapulmonary, transdermal, intrapleural, intrathecal, and oral routes of administration. For prevention and treatment purposes, the antibody or antibody-drug conjugate may be administered to a subject in a single bolus delivery, via continuous delivery (e.g., continuous transdermal delivery) over an extended time period, or in a repeated administration protocol (e.g., on an hourly, daily, or weekly basis).

Determination of effective dosages in this context is typically based on animal model studies followed up by human clinical trials and is guided by determining effective dosages and administration protocols that significantly reduce the occurrence or severity of the subject disease or disorder in model subjects. Effective doses of the compositions of the present invention vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy. Accordingly, a therapeutically or prophylactically effective amount is also one in which any undesired collateral effects are outweighed by beneficial effects of modulating NKp30-mediated NK cell activity. For administration of an anti-human-B7H6 monoclonal antibody or antibody-drug conjugate, a dosage typically ranges from about 0.1 µg to 100 mg/kg or 1 µg/kg to about 50 mg/kg, and more usually 10 µg to 5 mg/kg of the subject's body weight. In more specific embodiments, an effective amount of the agent is between about 1 µg/kg and about 20 mg/kg, between about 10 µg/kg and about 10 mg/kg, or between about 0.1 mg/kg and about 5 mg/kg. Dosages within this range can be achieved by single or multiple administrations, including, e.g., multiple administrations per day or daily, weekly, bi-weekly, or monthly administrations. For example, in certain variations, a regimen consists of an initial administration followed by multiple, subsequent administrations at weekly or bi-weekly intervals. Another regimen consists of an initial administration followed by multiple, subsequent administrations at monthly or bi-monthly intervals. Alternatively, administrations can be on an irregular basis as indicated by monitoring of NK cell activity and/or clinical symptoms of the disease or disorder.

Dosage of the pharmaceutical composition may be varied by the attending clinician to maintain a desired concentration at a target site. For example, if an intravenous mode of delivery is selected, local concentration of the agent in the bloodstream at the target tissue may be between about 1-50 nanomoles of the composition per liter, sometimes between about 1.0 nanomole per liter and 10, 15, or 25 nanomoles per liter depending on the subject's status and projected measured response. Higher or lower concentrations may be selected based on the mode of delivery, e.g., trans-epidermal delivery versus delivery to a mucosal surface. Dosage should also be adjusted based on the release rate of the administered formulation, e.g., nasal spray versus powder, sustained release oral or injected particles, transdermal formulations, etc. To achieve the same serum concentration level, for example, slow-release particles with a release rate of 5 nanomolar (under standard conditions) would be administered at about twice the dosage of particles with a release rate of 10 nanomolar.

A pharmaceutical composition comprising an anti-human-B7H6 monoclonal antibody or antibody-drug conjugate composition can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants. (See, e.g., Bremer et al., *Pharm. Biotechnol.* 10:239, 1997; Ranade, "Implants in Drug Delivery," in *Drug Delivery Systems* 95-123 (Ranade and Hollinger, eds., CRC Press 1995); Bremer et al., "Protein Delivery with Infusion Pumps," in *Protein Delivery: Physical Systems* 239-254 (Sanders and Hendren, eds., Plenum Press 1997); Yewey et al., "Delivery of Proteins from a Controlled Release Injectable Implant," in *Protein Delivery: Physical Systems* 93-117 (Sanders and Hendren, eds., Plenum Press 1997).) Other solid forms include creams, pastes, other topological applications, and the like.

Liposomes provide one means to deliver therapeutic compositions to a subject, e.g., intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments. (See, generally, Bakker-Woudenberg et al., *Eur. J. Clin. Microbiol. Infect. Dis.* 12 (Suppl. 1):561, 1993; Kim, *Drugs* 46:618, 1993; Ranade, "Site-Specific Drug Delivery Using Liposomes as Carriers," in *Drug Delivery Systems* 3-24 (Ranade and Hollinger, eds., CRC Press 1995).) Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s). (See, e.g., Machy et al., *Liposomes In Cell Biology And Pharmacology* (John Libbey 1987); Ostro et al., *American J. Hosp. Pharm.* 46:1576, 1989.) Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (see Scherphof et al., *Ann. N.Y. Acad. Sci.* 446:368, 1985). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (see Claassen et al., *Biochim. Biophys. Acta* 802:428, 1984). In addition, incorporation of glycolipid- or polyethelene glycol-derivatized phospholipids into liposome membranes has been shown to result in a significantly reduced uptake by the reticuloendothelial system (see Allen et al., *Biochim. Biophys. Acta* 1068:133, 1991; Allen et al., *Biochim. Biophys. Acta* 1150:9, 1993).

Liposomes can also be prepared to target particular cells or organs by varying phospholipid composition or by inserting receptors or counter-receptors into the liposomes. For example, liposomes, prepared with a high content of a non-ionic surfactant, have been used to target the liver. (See, e.g., Japanese Patent 04-244,018 to Hayakawa et al.; Kato et al., *Biol. Pharm. Bull.* 16:960, 1993.) These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver. (See Shimizu et al., *Biol. Pharm. Bull.* 20:881, 1997.)

Alternatively, various targeting counter-receptors can be bound to the surface of the liposome, such as antibodies, antibody fragments, carbohydrates, vitamins, and transport proteins. For example, for targeting to the liver, liposomes can be modified with branched type galactosyllipid derivatives to target asialoglycoprotein (galactose) receptors, which are exclusively expressed on the surface of liver cells. (See Kato and Sugiyama, *Crit. Rev. Ther. Drug Carrier Syst.* 14:287, 1997; Murahashi et al., *Biol. Pharm. Bull.* 20:259, 1997.) In a more general approach to tissue targeting, target cells are prelabeled with biotinylated antibodies specific for a counter-receptor expressed by the target cell. (See Harasym et al., *Adv. Drug Deliv. Rev.* 32:99, 1998.) After plasma elimination of free antibody, streptavidin-conjugated liposomes are administered. In another approach, targeting antibodies are directly attached to liposomes. (See Harasym et al., supra.)

Antibodies or antibody-drug conjugates can be encapsulated within liposomes using standard techniques of protein microencapsulation. (See, e.g., Anderson et al., *Infect. Immun.* 31:1099, 1981; Anderson et al., *Cancer Res.* 50:1853, 1990; Cohen et al., *Biochim. Biophys. Acta* 1063:95, 1991; Alving et al. "Preparation and Use of Liposomes in Immunological Studies," in *Liposome Technology* (Vol. III) 317 (Gregoriadis, ed., CRC Press, 2nd ed. 1993); Wassef et al., *Meth. Enzymol.* 149:124, 1987.) As noted above, therapeutically useful liposomes may contain a variety of components. For example, liposomes may comprise lipid derivatives of poly(ethylene glycol). (See Allen et al., *Biochim. Biophys. Acta* 1150:9, 1993.)

Degradable polymer micro spheres have been designed to maintain high systemic levels of therapeutic proteins. Micro spheres are prepared from degradable polymers such as poly (lactide-co-glycolide) (PLG), polyanhydrides, poly (ortho esters), nonbiodegradable ethylvinyl acetate polymers, in which proteins are entrapped in the polymer. (See, e.g., Gombotz and Pettit, Bioconjugate Chem. 6:332, 1995; Ranade, "Role of Polymers in Drug Delivery," in *Drug Delivery Systems* 51-93 (Ranade and Hollinger, eds., CRC Press 1995); Roskos and Maskiewicz, "Degradable Controlled Release Systems Useful for Protein Delivery," in *Protein Delivery: Physical Systems* 45-92 (Sanders and Hendren, eds., Plenum Press 1997); Bartus et al., *Science* 281:1161, 1998; Putney and Burke, *Nature Biotechnology* 16:153, 1998; Putney, *Curr. Opin. Chem. Biol.* 2:548, 1998.) Polyethylene glycol (PEG)-coated nanospheres can also provide carriers for intravenous administration of therapeutic proteins. (See, e.g., Gref et al., *Pharm. Biotechnol.* 10:167, 1997.)

Other dosage forms can be devised by those skilled in the art, as shown by, e.g., Ansel and Popovich, *Pharmaceutical Dosage Forms and Drug Delivery Systems* (Lea & Febiger, 5th ed. 1990); Gennaro (ed.), *Remington's Pharmaceutical Sciences* (Mack Publishing Company, 19th ed. 1995), and Ranade and Hollinger, *Drug Delivery Systems* (CRC Press 1996).

Pharmaceutical compositions as described herein may also be used in the context of combination therapy. The term "combination therapy" is used herein to denote that a subject is administered at least one therapeutically effective dose of an anti-human-B7H6 monoclonal antibody or antibody-drug conjugate in combination with a second agent for treatment of a disease or disorder. The anti-B7H6 antibody or antibody-drug conjugate and the second agent may be, for example, co-administered together (e.g., as a single composition comprising both agents, or simultaneously as separate compositions at the same or substantially the same site) or, alternatively, administered separately (e.g., at different times and/or at different administration sites).

Pharmaceutical compositions may be supplied as a kit comprising a container that comprises a therapeutic polypeptide or polynucleotide as described herein. A therapeutic molecule can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide or polynucleotide. Such a kit may further comprise written information on indications and usage of the pharmaceutical composition. For example, such information may include a statement that an anti-B7H6 composition is contraindicated in patients with known hypersensitivity to B7H6.

C. Methods of Detecting B7H6 Expression

The antibodies described herein also have uses in methods of detecting expression of B7H6, including diagnostic uses. Detection of B7H6 expression may be important for multiple reasons. For example, B7H6 expression in cells or tissues may be used in cancer detection. The detection may be used as part of screening, diagnosis, or prognosis of cancer. The method of detection may be used to compare the level of B7H6 expression in a biological sample from a subject to a standard or reference as part of determining the severity or stage of cancer or monitoring of treatment. The method of detection may take place once or be used multiple times for such uses as monitoring, for example, to monitor a subject's progress during treatment to indicate if the cancer is recurring.

In certain embodiments, a method of detecting cellular expression of B7H6 includes contacting a biological sample to be tested with an anti-B7H6 monoclonal antibody and then detecting binding of the antibody. The binding of the antibody indicates the presence of B7H6 on the cell. The antibody and B7H6 form an antibody-antigen complex and conditions under which the complex forms will be dependent on the biological sample and method used, and are determinations readily made by those skilled in the art. Suitable antibodies include antibodies that compete for binding to the extracellular domain of human B7H6 with an antibody produced by a hybridoma selected from the group consisting of (i) the hybridoma of clone 4E5.5 (Deposit No. CNCM I-4242); (ii) the hybridoma of clone 9G9.2 (Deposit No. CNCM I-4243); (iii) the hybridoma of clone 10E2.9 (Deposit No. CNCM I-4244); and (iv) the hybridoma of clone 17B1.3 (Deposit No. CNCM I-4245).

The biological sample may comprise intact human cells or a membrane fraction of the cell to be tested. For example, cells tested with the claimed methods will include cells suspected of expressing B7H6 and associated with cancer in a subject, such as, e.g., colon cancer cells, liver cancer cells, cervical cancer cells, lung cancer cells, pancreatic cancer cells, prostate cancer cells, prohemocytic leukemia cells, B-cell lymphoma cells, monocytic lymphoma cells, erythroleukemia cells, Burkitt's lymphoma cells, and chronic myelogenous leukemia cells, to name a few.

Detection of binding by the antibody to indicate the presence of a B7H6 expressing cell include assays for specific binding by any method known in the art. There are many different binding assay formats that are well known. For example, binding assay systems can be direct or indirect, using techniques such western blots, radioimmunoassay, ELISA, "sandwich" immunoassays, immunoprecipitation assays, precipitin assays, gel diffusion precipitin assays, immunoradiometric assays, fluorescent immunoassays, protein A immunoassays, complement-fixation assays, to name just a few. Such assays are routine and well known in the art.

To enhance detection, the antibody is labeled with a detectable label such as a radioisotope, a fluorescent label, a chemiluminescent label, an enzyme label, or a bioluminescent label. Methods of conjugating labels to antibodies are known in art and any appropriate method can be used.

The present invention further provides a method for diagnosing a subject suspected of having a type of cancer expressing B7H6. The method comprises administering to the subject, generally a human (but can be another mammal such as a non-human primate, dog, cat, pig etc.), an anti-B7H6 monoclonal antibody conjugated to a detectable label, such as those described above. Suitable antibodies include antibodies that compete for binding to the extracellular domain of human B7H6 (amino acid residues 25-266 of SEQ ID NO:2) with an antibody produced by a hybridoma selected from (i) the hybridoma of clone designation number 4E5.5; (ii) the hybridoma of clone designation number 9G9.2; (iii) the hybridoma of clone designation number 10E2.9; and (iv) the hybridoma of clone designation number 17B1.3. In some embodiments, the antibody competes for binding to the extracellular domain of B7H6 with an antibody produced by a hybridoma selected from (ii)-(iii) above. In particular variations, the antibody is a chimeric or humanized antibody derived from an antibody produced by a hybridoma selected from (i)-(iv) above or from (ii)-(iii) above. Following administration of the antibody, the distribution of the antibody within the subject is detected. Methods for detecting distribution of any specific label are known to those skilled in the art and any appropriate method can be used. Some non-limiting examples include, computed tomography (CT), position emission tomography (PET), magnetic resonance imaging (MRI), fluorescence, chemiluminescence and sonography.

The invention is further illustrated by the following non-limiting examples.

EXAMPLES

Example 1

Production and Selection of Mouse Anti-Human B7H6 Monoclonal Antibodies

A. Immunization

A Balb/c mouse was immunized according to the following protocol:

D0: i.v. injection of 100 µg soluble B7H6 (the extracellular domain of human B7H6 with a C-terminal murine Fc fusion (hB7H6/mFc2; mature form as shown in residues 25 to 500 of SEQ ID NO:3))

D15: i.v. injection of 100 µg soluble B7H6

D25: Boost i.p. with 100 µg soluble B7H6

Three days after the third immunization, the spleen was harvested. The splenocytes were isolated and fused with myeloma cells and seeded in 40 96-wells plates. After 3 weeks in culture, supernatants of 3840 hybridomas were screened for the presence of anti-human-B7H6 monoclonal antibodies.

B. First Screening of Hybridomas

To select the hybridomas producing anti-human-B7H6 monoclonal antibodies, P815 cells expressing B7H1 and P815 cells expressing B7H6 were stained with the supernatant of the 3840 hybridomas. The staining on the hybridomas was revealed by FACS analysis using a Cy5-conjugated anti-mouse Ig. In order to differentiate the two P815 transfectants, P815 B7-H1 cells were first stained with CFSE. The results showed 114 out of 3840 hybridoma supernatants were positive for staining of B7H6-expressing P815 cells relative to B7H1-expressing P815 cells, thereby indicating the production of anti-B7H6 mAbs by the corresponding hybridomas.

C. Second Screening of Hybridomas

A second screen was performed to select blocking antibodies. In order to identify these hybridomas, the ability of each of the 114 supernatants to block NKp30Fc binding to P815.B7H6 cells was assessed. The selected hybridomas were checked in parallel to confirm they were still producing anti-B7H6 mAbs by staining P815.B7H6. In addition, an anti-B7H6 polyclonal antibody (pAb), previously shown to inhibit the binding of NKp30 binding to B7H6-expressing P815 cells was used as a positive control.

The results showed that P815.B7-H6 cells were stained by NKp30Fc and the anti-B7H6 pAb inhibited the staining when incubated at 10 µg/ml. The 114 supernatants were divided in 4 groups according to the results: (1) hybridomas producing anti-B7H6 mAbs that blocked NKp30Fc binding (1/114); (2) hybridomas producing anti-B7H6 mAbs that did not block NKp30Fc binding (27/114); (3) hybridomas producing anti-B7H6 mAbs that partially blocked NKp30Fc binding (1/114); (4) hybridomas that did not produce anymore anti-B7H6 mAbs (85/114). In conclusion, 29 hybridomas efficiently produced anti-B7H6 mAbs and only 2 out of them could be blocking mAbs. The 29 hybridomas producing anti-B7H6 mAbs were cloned.

D. Cloning of Hybridomas

After cloning 29 selected hybridomas, 11 hybridomas did not grow, 5 hybridomas only raised negative clones, and 13 generated positive clones. Amplification in flasks resulted in only 9 clones derived from 5 different hybridomas still producing anti-B7H6 mAb. The following clones were characterized and all were identified as mouse IgG1: 4E5.5, 5E1.4, 9G9.2, 10E2.9, and 17B1.3.

Hybridomas expressing monoclonal antibodies to B7H6 were deposited with the Collection Nationale de Cultures de Microorganismes (CNCM, Institut Pasteur; Paris, France) patent depository as original deposits under the Budapest Treaty and were given the following CNCM depository accession numbers: clone 4E5.5 (Deposit No. CNCM I-4242, deposited on Nov. 18, 2009); clone 9G9.2 (Deposit No. CNCM I-4243, deposited on Nov. 18, 2009); clone 10E2.9 (Deposit No. CNCM I-4244, deposited on Nov. 18, 2009); and clone 17B1.3 (Deposit No. CNCM I-4245, deposited on Nov. 18, 2009).

Example 2

Characterization of Mouse Anti-Human B7H6 Monoclonal Antibodies

A. Mouse Anti-Human-B7H6 Monoclonal Antibody Reactivity to Tumor Cell Lines

Each anti-human-B6H7 mAb (4E5.5, 5E1.4, 9G9.2, 10E2.9, and 17B1.3) was compared to the anti B7-H6 polyclonal antibody for the staining of the following tumor cell lines: HEK-293, HeLa EV2, K562, and Raji. P815.B7H6 cells and P815.B7-H1 cells were used as a positive control and a negative control, respectively. Each of the five mAbs was positive for staining on each of the tumor cell lines, with some variations in the staining intensity profile for each mAb. For example, 17B1.3 stained P815.B7-H6 with the same intensity than the pAb, however it did not stain Raji cells with the same efficacy. Also, staining of HEK-293 and HeLa EV2 cells was slightly less intense with 17B1.3 than with the pAb, while staining of K562 was slightly less with 4E5.5 than with the pAb.

C. Epitope Differentiation by Competition Assay

To define whether the 4E5.5, 5E1.4, 9G9.2, 10E2.9 and 17B1.3 mAbs target different epitopes, a competition assay between the mAbs was done. The only clone directly conjugated with a fluorochrome (Alexa 647, Molecular Probes) was 9G9.2. Therefore, this antibody was used in evaluating binding of 9G9.2-Alexa 647 to HEK 293 cells after incubation with the other purified anti-B7H6 mAbs. HEK-293 cells were first incubated with the purified mAbs at 30 µg/ml then with 9G9.2 Alexa 647 at 10 µg/ml. Staining of the HEK-293 with 9G9.2-Alexa 647 was then evaluated by FACS® (BD Sciences, Inc., Franklin Lakes, N.J.). The results of this analysis showed that pre-incubation of HEK-293 cells with mAbs 10E2.9, 4E5.5, or 9G9.2 substantially decreased the intensity of staining with 9G9.2-Alexa 647. Pre-incubation with 10E2.9, 4E5.5, or 9G9.2 substantially decreased staining intensity with 9G9.2-Alexa 647, while pre-incubation with 5E1.4 only slightly decreased staining intensity. Pre-incubation with 17B1.3 had no significant effect on 9G9.2-Alexa 647 staining. These results show that 10E2.9, 4E5.5, and 9G9.2 target overlapping (if not substantially the same or similar) epitopes. In contrast, 17B1.3 and 9G9.2 (and possibly 5E1.4 and 9G9.2) recognized non-overlapping epitopes.

D. Mouse Anti-Human-B7H6 Monoclonal Antibodies Partially Block NKp30Fc Binding

To identify the mAbs that had some blocking of NKp30Fc binding, a competition assay was performed. NKp30Fc is a soluble form of human NKp30 consisting of the extracellular domain of human NKp30 with a C-terminal Fc fusion. The binding of NKp30Fc to HEK 293 cells after incubation with B7H6 polyclonal antibody, mIgG1, control, and purified 4E5.5, 5E1.4, 9G9.2, 10E2.9 and 17B1.3 anti-B7-H6 mAbs was evaluated. HEK-293 cells were first incubated with the purified mAbs at 30 µg/ml washed, then incubated with the preformed complex NKp30Fc (5 µg/ml)/PE-conjugated anti-huIg (5 µg/ml, Jackson ImmunoResearch Laboratories, West Grove, Pa.). Fluorescent stainings were analyzed on a BD FACSCalibur™ (BD Sciences Inc.) using FlowJo software (Tree Star, Inc. Ashland, Oreg.). The results showed that 4E5.5 and 17B1.3 partially blocked NKp30Fc binding.

E. Mouse Anti-Human-B7H6 Monoclonal Antibodies Partially Block DOMSP30 Activation To confirm that 17B1.3 and 4E5.5 were blocking mAbs, a functional assay with the reporter cells DOMSP30 was performed. DOMSP30 cells were used as a reporter cell system to evaluate whether B7H6 was able to induce signaling directly through NKp30. (See Schleinitz et al. *Arthritis Rheum.* 58:32156-3223, 2008, for DOMSP30 cells). Activation of DOMSP30 could be detected either by IL-2 production after 24 hours of stimulation or by CD69 upregulation after 4 hours of stimulation. DOMSP30 cells were cocultivated either with HeLa EV2 or HeLa PF cell lines in presence or absence of anti-NKp30, anti-NKp46, anti-B7H6 polyclonal antibody, mouse IgG1 or one of the anti-human B7H6 monoclonal antibodies 4E5.5, 5E1.4, 9G9.2, 10E2.9 and 17B1.3 (at 10 µg/ml). After 4 hours of coculture, the number (percent) of CD69+ DOMSP30 cells was measured.

The results showed that anti-NKp30 completely blocked DOMSP30 activation and that 4E5.5 and 17B1.3 partially inhibited DOMSP30 activation. Briefly, in the absence of antibody, about 75% of DOMSP30 cells were CD69+, as compared to the following CD69+ percentages with antibody cocultivation: less than 10% with anti-NKP30; about 20% with anti-B7H6 pAb; and about 45% with each of mAbs 4E5.5 and 17B1.3. In contrast, anti-NKp46 and each of mAbs 9G9.2, 10E2.9, and 5E1.4 showed no effect on DOMSP30 activation.

F. Mouse Anti-Human-B7H6 Monoclonal Antibody 17B1.3 is a Blotting Antibody

The ability of the anti-B7H6 mAbs to act as blotting antibodies was tested by performing immunoblotting experiments with protein extracts from three different cell lines: KHYG-1, which do not express B7H6, and P815.B7-H6 and HEK293, which each express B7H6. Anti-B7H6 pAb was used as a positive control. The cells were collected, washed in cold PBS 1×, suspended in Lysis Buffer (10 mM Tris-HCl pH 7.6; 150 mM NaCl; 1% Triton X; 1× Protease Inhibitor (Roche Applied Science, Indianapolis, Ind.) at a concentration of $20.10^6$ cells.mL-1 and left on ice for 30 min. The lysates were then centrifuged 10 min, at 13 200 rpm, at 4° C. The supernatant was collected and protein concentration measured with BCA kit from Pierce and adjusted to 1.5 mg/ml. 30 μL of each cell lysate was mixed with 10 μL at 4× Loading Buffer and heated during 10 min at 95° C. They were then loaded on a precast gel (2-20% Precise Protein Gel from Thermo scientific) and run at 110 V. After electrophoresis, samples were transferred on a membrane using iBlot Gel Transfer Stack Nitrocellulose, Regular kit (Invitrogen, San Diego, Calif.). The membrane was saturated in 1×TBST (100 mM Tris HCl pH=7.5+0.9% HCl+0.05% Tween)+5% milk during 1 h at RT and then incubated with each anti-B7H6 mAbs at 2 μg·mL-1 in 1×TBST+5% milk overnight at 4° C. The membrane was washed 2 times 10 min in 1×TBST and incubated during 1 h at RT with a sheep anti-mouse IgG antibody coupled to Horseradish Peroxidase diluted in 1×TBST+5% milk. The membrane was then washed 4 times 20 min in TBST and revealed with ECL kit (GE Healthcare, Piscataway, N.J.).

Among the five mAbs, only mAb 10E2.9 (10 μg/ml) was capable of performing as an immunoblotting mAb under the conditions tested. These results suggest that the B7H6 epitopes for mAbs 4E5.5, 5E1.4, 9G9.2, and 17B1.3 may not be linear, but may instead comprise discontinuous regions of the B7H6 polypeptide.

G. Three of the Five Anti-Human-B7H6 Monoclonal Antibodies are Efficient for Immunoprecipitation To evaluate whether 4E5.5, 5E1.4, 9G9.2, 10E2.9 and 17B1.3 could be efficient for immunoprecipitations, P815.B7-H6 protein extracts were prepared and immunoprecipitations were performed with the different mAbs. The immunoprecipitates were run on a SDS gel and presence of B7H6 was observed using the anti-B7H6 polyclonal antibody and HRP-conjugated anti mouse Ig. The results showed that 4E5.5, 9G9.2 and 10E2.9 immunoprecipitated B7H6 from P815.B7-H6 protein extracts, whereas 5E1.4 and 17B1.3 did not.

Example 3

BxPC3 Pancreatic Carcinoma Model for Evaluating Efficacy of an Anti-B7H6 Antibody or Antibody-Drug Conjugate Against Tumor Growth To test if an anti-human-B7H6 monoclonal antibody or anti-human-B7H6 monoclonal antibody-drug conjugate has activity on tumor growth in mice, groups of mice are injected s.c with the BxPC3 pancreatic tumor on Day 0. Once tumors grow to 150-200 mm$^3$, groups of mice (n=10/gp) mice are then injected with 1 mg/Kg to 30 mg/Kg control reagent, anti-B7H6 antibody, or anti-B7H6 antibody-drug conjugate 1×-3×/week for 3 weeks. Tumor volume is monitored 3×/week for 5 weeks. Significantly smaller tumors in mice injected with an anti-B7H6 antibody or antibody-drug conjugate, as compared to mice injected with control reagent, indicates efficacy of the antagonist for inhibition of tumor growth.

Study Design:

Eight to ten-week old female C.B-17 SCID mice (Charles River Laboratories) are injected s.c. on the right flank with $2×10^6$ BxPC-3 cells on Day 0, Starting with a tumor size of 150-200 mm$^3$, groups of mice (n=10/group) are injected i.p. with 1 mg/Kg to 30 mg/Kg control reagent, anti-B7H6 antibody, or anti-B7H6 antibody-drug conjugate 1×-3×/week for 3 weeks. Tumor growth is monitored 3×/week for 5 weeks using caliper measurements. Tumor volume is calculated using the formula $½*(B)^2*L$ (mm$^3$)

Example 4

Inhibition of Human Hepatocellular Carcinoma Cell Growth In Vivo Using Anti-Human-B7H6 Monoclonal Antibody or Antibody-Drug Conjugate To evaluate anti-tumor activity of an anti-human-B7H6 monoclonal antibody or antibody-drug conjugate against human hepatocellular carcinoma cells in vivo, groups of BALB/c nude mice are injected with either HuH7 or C3A hepatocellular carcinoma cells on Day 0. Groups (n=10/group) of tumor bearing mice receive 5-75 μg of anti-human-B7H6 monoclonal antibody or antibody-drug conjugate by i.p. or peritumoral injection every other day (EOD) from Days 5-33. Tumor volume is monitored 3×/week for 6 weeks Inhibition of tumor growth by anti-human-B7H6 monoclonal antibody or antibody-drug conjugate indicates that the respective protein has inhibitory effects on human heptocellular carcinoma in vivo.

Study Design:

Eight-week old female BALB/c nude mice (Charles River Laboratories) are injected s.c. on the right flank with $6×10^6$ HuH7 or C3A cells on Day 0. Groups of mice (n=10/group) are injected i.p. or peritumorally with 5 μg-75 μg of an anti-human-B7H6 monoclonal antibody or antibody-drug conjugate from days 5-33. Injections are given in a total volume of 200 μl. Tumor growth is monitored 3×/week for 6 weeks using caliper measurements. Tumor volume was calculated using the formula $½*(B)^2*L$ (mm$^3$)

Example 5

Inhibition of Human Prostate Carcinoma Cell Growth In Vivo Using Anti-Human-B7H6 Monoclonal Antibody or Antibody-Drug Conjugate To evaluate anti-tumor activity of an anti-human-B7H6 monoclonal antibody or antibody-drug conjugate against human prostate carcinoma cells in vivo, groups of BALB/c nude mice are injected with either PC-3 or DU-145 prostate carcinoma cells on Day 0. Groups (n=10/group) of tumor bearing mice receive 5-75 μg of anti-human-B7H6 monoclonal antibody or antibody-drug conjugate by i.p. or peritumoral injection every other day (EOD) from Days 5-33. Tumor volume is monitored 3×/week for 6 weeks. Inhibition of tumor growth (volume or weight) by an anti-human-B7H6 monoclonal antibody or antibody-drug conjugate indicates that the respective protein has inhibitory effects on human prostate carcinoma in vivo.

Study Design:

Eight-week old female BALB/c nude mice (Charles River Laboratories) are injected s.c. on the right flank or orthotopically in the prostate lobe with $10×10^6$ PC-3 or $6×10^6$ DU-145 cells on Day 0. Groups of mice (n=10/group) are injected i.p. or peritumorally (s.c model only) with 5-75 µg of anti-human-B7H6 monoclonal antibody or antibody-drug conjugate from days 5-33. Injections are given in a total volume of 200 µl. For s.c. tumors, tumor growth is monitored 3×/week for 6 weeks using caliper measurements. Tumor volume is calculated using the formula ½*(B)$^2$*L (mm$^3$). For orthotopic tumors, mice are terminated at the end of the study and tumor weighed to enable tumor load assessment.

Example 6

Inhibition of Human Colon Carcinoma Cells In Vivo Using Anti-Human-B7H6 Monoclonal Antibody or Antibody-Drug Conjugate To evaluate anti-tumor activity of an anti-human-B7H6 monoclonal antibody or antibody-drug conjugate against human colon carcinoma cells in vivo, groups of BALB/c nude mice are injected with either DLD-1 or HCT-116 colon carcinoma cells on Day 0. Groups (n=10/group) of tumor bearing mice receive 5-75 µg of anti-human-B7H6 monoclonal antibody or antibody-drug conjugate by i.p. or peritumoral injection every other day (EOD) from Days 5-33. Tumor volume is monitored 3×/week for 6 weeks Inhibition of tumor growth (volume or weight) by anti-human-B7H6 monoclonal antibody or antibody-drug conjugate suggests that the respective protein has inhibitory effects on human colon carcinoma in vivo.

Study Design:

Eight-week old female BALB/c nude mice (Charles River Laboratories) are injected s.c. on the right flank or orthotopically in the colonic wall with 6×10$^6$ DLD-1 or HCT-116 cells on Day 0. Groups of mice (n=10/group) are injected i.p. or peritumorally (for s.c model only) with 5-75 µg of anti-human-B7H6 monoclonal antibody or antibody-drug conjugate from days 5-33. Injections are given in a total volume of 200 µl. For s.c tumors, tumor growth is monitored 3×/week for 6 weeks using caliper measurements. Tumor volume is calculated using the formula ½*(B)$^2$*L (mm$^3$) For orthotopic tumors, mice are terminated at the end of the study and tumor weighed to enable tumor load assessment.

Example 7

Inhibition of Human Pancreatic Carcinoma Cells In Vivo Using Anti-Human-B7H6 Monoclonal Antibody or Antibody-Drug Conjugate To evaluate anti-tumor activity of an anti-human-B7H6 monoclonal antibody or antibody-drug conjugate against human pancreatic carcinoma cells in vivo, groups of BALB/c nude mice are injected with either BxPC-3 or HPAF-II pancreatic carcinoma cells on Day 0. Groups (n=10/group) of tumor bearing mice receive 5-75 µg of anti-human-B7H6 monoclonal antibody or antibody-drug conjugate by i.p. or peritumoral injection every other day (EOD) from Days 5-33. Tumor volume is monitored 3×/week for 6 weeks. Inhibition of tumor growth (volume or weight) by anti-human-B7H6 monoclonal antibody or antibody-drug conjugate suggests that the respective protein has inhibitory effects on human pancreatic carcinoma in vivo.

Study Design:

Eight-week old female BALB/c nude mice (Charles River Laboratories) are injected s.c. on the right flank or orthotopically in the pancreatic lobe with 6×10$^6$ BxPC-3 or HPAF-II cells on Day 0. Groups of mice (n=10/group) are injected i.p. or peritumorally (for s.c model only) with 5-75 µg of anti-human-B7H6 monoclonal antibody or antibody-drug conjugate from days 5-33. Injections are given in a total volume of 200 µl. For s.c tumors, tumor growth is monitored 3×/week for 6 weeks using caliper measurements. Tumor volume was calculated using the formula ½*(B)$^2$*L (mm$^3$). For orthotopic tumors, mice are terminated at the end of the study and tumor weighed to enable tumor load assessment.

Example 8

Inhibition of B-Cell Lymphoma In Vivo Using Anti-Human-B7H6 Monoclonal Antibody or Antibody-Drug Conjugate Human B-lymphoma cell lines are maintained in vitro by passage in growth medium. The cells are washed thoroughly in PBS to remove culture components.

SCID Mice are injected with (typically) 1×10$^6$ human lymphoma cells via the tail vein in a 100 microliter volume. The optimal number of cell injected is determined empirically in a pilot study to yield tumor take consistently with desired kinetics. Anti-human-B7H6 monoclonal antibody or antibody-drug conjugate treatment is begun the next day by either subcutaneous implantation of an ALZET® osmotic mini-pump (ALZET, Cupertino, Calif.) or by daily i.p. injection of anti-human-B7H6 monoclonal antibody or antibody-drug conjugate or vehicle. Mice are monitored for survival and significant morbidity. Mice that lose greater than 20% of their initial body weight are sacrificed, as well as mice that exhibit substantial morbidity such as hind limb paralysis. Depending on the lymphoma cell line employed, the untreated mice typically die in 3 to 6 weeks. For B cell lymphomas that secrete IgG or IgM, the disease progression can also be monitored by weekly blood sampling and measuring serum human immunoglobulin levels by ELISA.

Anti-Human-B7H6 Monoclonal Antibody or Antibody-Drug Conjugate Dose Response/IM-9 Model Mice are injected with 1×10$^6$ IM-9 cells, and 28 day osmotic mini pumps implanted the following day. The pumps are loaded with the following concentrations of anti-human-B7H6 monoclonal antibody or antibody-drug conjugate to deliver: 0, 0.12, 1.2, or 12 micrograms per day with 8 mice per dose group. Increased protection of mice from the tumor cell line with increased dose of antibody or antibody-drug conjugate indicates that the effects of the anti-human-B7H6 monoclonal antibody or antibody-drug conjugate are dose dependent. Surviving mice at the end of the experiment have no signs of disease and no detectable human IgG in their serum.

These data demonstrate that the efficacy of anti-human-B7H6 monoclonal antibody or antibody-drug conjugate in SCID mouse lymphoma models correlates with the ability to inhibit the growth of the lymphoma cell lines in vivo.

Example 9

Inhibition of B-Cell Derived Tumors In Vivo Using Anti-Human-B7H6 Monoclonal Antibody or Antibody-Drug Conjugate Administration of anti-human-B7H6 monoclonal antibody or antibody-drug conjugate by constant infusion via mini-osmotic pumps results in steady state serum concentrations proportional to the concentration of the anti-human-B7H6 monoclonal antibody or antibody-drug conjugate contained in the pump. 0.22 ml of anti-human-B7H6 monoclonal antibody or antibody-drug conjugate contained in phosphate buffered saline (pH 6.0) at a concentration of 2 mg/ml or 0.2 mg/ml is loaded under sterile conditions into Alzet mini-osmotic pumps (model 2004; Alza corporation Palo Alto, Calif.). Pumps are implanted subcutaneously in mice through a 1 cm incision in the dorsal skin, and the skin is closed with sterile wound closures. These pumps are designed to deliver their contents at a rate of 0.25 μl per hour over a period of 28 days. This method of administration results in significant increase in survival in mice injected with tumor cells (below).

Effect of Anti-Human-B7H6 Monoclonal Antibody or Antibody Drug Conjugate on B-Cell Derived Tumors In Vivo The effects of anti-human-B7H6 monoclonal antibody or antibody-drug conjugate are tested in vivo using a mouse tumor xenograft model described herein. The xenograft model to be tested is human lymphoblastoid cell line IM-9. C.B-17 SCID mice (female C.B-17/IcrHsd-scid; Harlan, Indianapolis, Ind.) are divided into 4 groups. On day 0, IM-9 cells are harvested from culture and injected intravenously, via the tail vein, to all mice (about 1,000,000 cells per mouse). On day 1, mini-osmotic pumps containing test article or control article are implanted subcutaneously in the mice. Mice in groups 1-3 (n=9 per group) are delivered anti-human-B7H6 monoclonal antibody or antibody-drug conjugate: group 1 contains 2.0 mg/mL of anti-human-B7H6 monoclonal antibody or antibody-drug conjugate and is delivered 12 μg per day; group 2 contains 0.20 mg/mL and is delivered 1.2 μg per day; group 3 contained 0.02 mg/mL and is delivered 0.12 μg per day. Mice in group 4 (n=9) are a control and are treated with vehicle (PBS pH 6.0).

Increased survival of treatment groups (e.g., either 12 μg/day or 1.2 μg/day) compared to vehicle treated mice shows that anti-human-B7H6 monoclonal antibody or antibody-drug conjugate reduces the effects of the B-cell tumor cells in vivo.

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed:

1. An isolated monoclonal antibody, or antigen binding portion thereof, that binds to the same epitope on human B7H6 as an antibody produced by the hybridoma of clone designation number 4E5.5 (Deposit No. CNCM I-4242) or number 17B1.3 (Deposit No. CNCM I-4245).

2. The antibody of claim 1, wherein said antibody is selected from the group consisting of a murine antibody, a chimeric antibody, a humanized antibody, and a human antibody.

3. The antibody of claim 1, wherein said antibody is a murine antibody produced by the hybridoma of clone designation number 4E5.5, or an antigen-binding fragment thereof, or number 17B1.3, or an antigen-binding fragment thereof.

4. The antibody of claim 1, wherein said antibody is a humanized antibody derived from an antibody produced by the hybridoma of clone designation number 4E5.5, or an antigen-binding fragment thereof, or number 17B1.3, or an antigen-binding fragment thereof.

5. The antibody of claim 1, wherein said antibody is a single chain antibody.

6. The antibody of claim 1, wherein said antibody comprises an Fc region having ADCC activity or CDC activity.

7. The antibody of claim 6, wherein the Fc region is a single chain Fc (scFc).

8. A composition comprising, the antibody of claim 1 and a pharmaceutically acceptable carrier.

9. An antibody-drug conjugate comprising, the monoclonal antibody of claim 1, or antigen binding portion thereof, conjugated to a cytotoxic agent.

10. The antibody-drug conjugate of claim 9, wherein the antibody is selected from the group consisting of a murine antibody, a chimeric antibody, a humanized antibody, and a human antibody.

11. The antibody-drug conjugate of claim 9, wherein the antibody is a humanized antibody derived from an antibody produced by the hybridoma of clone designation number 4E5.5 or number 17B1.3.

12. The antibody-drug conjugate of claim 9, wherein the antibody is a single chain antibody or the Fc region is a single chain Fc (scFc).

13. The antibody-drug conjugate of claim 9, wherein the antibody comprises an Fc region having ADCC activity and/or CDC activity.

14. The antibody-drug conjugate of claim 13, wherein the Fc region is a single chain Fc (scFc).

15. The antibody-drug conjugate of claim 9, wherein the cytotoxic agent is selected from the group consisting of an anti-tubulin agent, a DNA minor groove binding agent, a DNA minor groove alkylating agent, a duocarmycin, and a puromycin.

16. The antibody-drug conjugate of claim 15, wherein the anti-tubulin agent is selected from the group consisting of a dolastatin, a vinca alkaloid, a podophyllatoxin, a taxane, a baccatin derivative, a cryptophysin, a maytansinoid, and a combretastatin.

17. The antibody-drug conjugate of claim 9, wherein the antibody is conjugated to the cytotoxic agent via a linker.

18. The antibody-drug conjugate of claim 17, wherein the linker is cleavable under intracellular conditions.

19. The antibody-drug conjugate of claim 18, wherein the cleavable linker is a peptide linker cleavable by an intracellular protease.

20. A composition comprising, the antibody-drug conjugate of claim 9 and a pharmaceutically acceptable carrier.

21. An antibody-producing cell selected from the group consisting of:
   a) the hybridoma of clone designation number 4E5.5 (Deposit No. CNCM I-4242); and
   b) the hybridoma of clone designation number 17B1.3 (Deposit No. CNCM I-4245).

22. The antibody of claim 1, wherein the antibody binds to human B7H6 and inhibits the interaction of human B7H6 with human NKp30.

23. An isolated antibody, or antigen-binding fragment thereof, that binds to human B7H6, comprising the heavy and light chain CDR sequences, or the heavy and light chain variable region sequences, of an antibody produced by the hybridoma of clone designation number 4E5.5 or number 17B1.3.

\* \* \* \* \*

SEQUENCE LISTING

<160> NUMBER OF SEQ ID NOS: 3

<210> SEQ ID NO 1
<211> LENGTH: 1365
<212> TYPE: DNA
<213> ORGANISM: Homo Sapiens

<400> SEQUENCE: 1

```
atgacgtgga gggctgccgc ctccacgtgc gcggcgctcc tgattctgct gtgggcgctg      60
acgaccgaag gtgatctgaa agtagagatg atggcagggg ggactcagat cacacccctg     120
aatgacaatg tcaccatatt ctgcaatatc tttattccc aaccccctcaa catcacgtct     180 atgggtatca cctggttttg gaagagtctg acgtttgaca aagaagtcaa agtctttgaa     240
ttttttggag atcaccaaga ggcattccga cctggagcca ttgtgtctcc atggaggctg     300
aagagtgggg acgcctcact gcggctgcct ggaatccagc tggaggaagc aggagagtac     360
cgatgtgagg tggtggtcac ccctctgaag gcacagggaa cagtccagct tgaagttgtg     420
gcttccccag ccagcagatt gttgctggat caagtgggca tgaaagagaa tgaagacaaa     480
tatatgtgtg agtcaagtgg gttctaccca gaggctatta atataacatg ggagaagcag     540
acccagaagt ttccccatcc catagagatt tctgaggatg tcatcactgg tcccaccatc     600
aagaatatgg atggcacatt taatgtcact agctgcttga agctgaactc ctctcaggaa     660
gaccctggga ctgtctacca gtgtgtggta cggcatgcgt ccttgcatac ccccttgagg     720 agcaactta ccctgactgc tgctcggcac agtctttctg aaactgagaa gacagataat     780
ttttccattc attggtggcc tatttcattc attggtgttg gactggtttt attaattgtt     840
ttgattcctt ggaaaaagat atgtaacaaa tcatcttcag cctatactcc tctcaagtgc     900
attctgaaac actggaactc ctttgacact cagactctga agaaagagca cctcatattc     960
ttttgcactc gggcatggcc gtcttaccag ctgcaggatg gggaggcttg gcctcctgag    1020
ggaagtgtta atattaatac tattcaacaa ctagatgttt tctgcagaca ggagggcaaa    1080
tggtccgagg ttccttatgt gcaagccttc tttgccttgc gagacaaccc agatctttgt    1140
cagtgttgta gaattgaccc tgctctccta acagttacat caggcaagtc catagatgat    1200
aattccacaa agtctgagaa acaaacccct agggaacact cggatgcagt tccggatgcc    1260
```

```
ccaatccttc ctgtctcccc tatctgggaa cctcctccag ccacaacatc aacaactcca      1320
gttctatcct cccaacccc aactttactg ttaccctac agtaa                        1365
```

<210> SEQ ID NO 2
<211> LENGTH: 454
<212> TYPE: PRT
<213> ORGANISM: Homo Sapiens

<400> SEQUENCE: 2

```
Met Thr Trp Arg Ala Ala Ala Ser Thr Cys Ala Ala Leu Leu Ile Leu
1               5                   10                  15

Leu Trp Ala Leu Thr Thr Glu Gly Asp Leu Lys Val Glu Met Met Ala
            20                  25                  30

Gly Gly Thr Gln Ile Thr Pro Leu Asn Asp Asn Val Thr Ile Phe Cys
        35                  40                  45

Asn Ile Phe Tyr Ser Gln Pro Leu Asn Ile Thr Ser Met Gly Ile Thr
    50                  55                  60

Trp Phe Trp Lys Ser Leu Thr Phe Asp Lys Glu Val Lys Val Phe Glu
65                  70                  75                  80

Phe Phe Gly Asp His Gln Glu Ala Phe Arg Pro Gly Ala Ile Val Ser
                85                  90                  95

Pro Trp Arg Leu Lys Ser Gly Asp Ala Ser Leu Arg Leu Pro Gly Ile
            100                 105                 110

Gln Leu Glu Glu Ala Gly Glu Tyr Arg Cys Glu Val Val Val Thr Pro
        115                 120                 125

Leu Lys Ala Gln Gly Thr Val Gln Leu Glu Val Val Ala Ser Pro Ala
    130                 135                 140

Ser Arg Leu Leu Leu Asp Gln Val Gly Met Lys Glu Asn Glu Asp Lys
145                 150                 155                 160

Tyr Met Cys Glu Ser Ser Gly Phe Tyr Pro Glu Ala Ile Asn Ile Thr
                165                 170                 175

Trp Glu Lys Gln Thr Gln Lys Phe Pro His Pro Ile Glu Ile Ser Glu
            180                 185                 190

Asp Val Ile Thr Gly Pro Thr Ile Lys Asn Met Asp Gly Thr Phe Asn
        195                 200                 205

Val Thr Ser Cys Leu Lys Leu Asn Ser Ser Gln Glu Asp Pro Gly Thr
    210                 215                 220

Val Tyr Gln Cys Val Val Arg His Ala Ser Leu His Thr Pro Leu Arg
225                 230                 235                 240

Ser Asn Phe Thr Leu Thr Ala Ala Arg His Ser Leu Ser Glu Thr Glu
                245                 250                 255

Lys Thr Asp Asn Phe Ser Ile His Trp Trp Pro Ile Ser Phe Ile Gly
            260                 265                 270

Val Gly Leu Val Leu Leu Ile Val Leu Ile Pro Trp Lys Lys Ile Cys
        275                 280                 285

Asn Lys Ser Ser Ser Ala Tyr Thr Pro Leu Lys Cys Ile Leu Lys His
    290                 295                 300

Trp Asn Ser Phe Asp Thr Gln Thr Leu Lys Lys Glu His Leu Ile Phe
305                 310                 315                 320

Phe Cys Thr Arg Ala Trp Pro Ser Tyr Gln Leu Gln Asp Gly Glu Ala
                325                 330                 335

Trp Pro Pro Glu Gly Ser Val Asn Ile Asn Thr Ile Gln Gln Leu Asp
            340                 345                 350

Val Phe Cys Arg Gln Glu Gly Lys Trp Ser Glu Val Pro Tyr Val Gln
```

```
            355                 360                 365
Ala Phe Phe Ala Leu Arg Asp Asn Pro Asp Leu Cys Gln Cys Cys Arg
    370                 375                 380

Ile Asp Pro Ala Leu Leu Thr Val Thr Ser Gly Lys Ser Ile Asp Asp
385                 390                 395                 400

Asn Ser Thr Lys Ser Glu Lys Gln Thr Pro Arg Glu His Ser Asp Ala
                405                 410                 415

Val Pro Asp Ala Pro Ile Leu Pro Val Ser Pro Ile Trp Glu Pro Pro
            420                 425                 430

Pro Ala Thr Thr Ser Thr Thr Pro Val Leu Ser Ser Gln Pro Pro Thr
        435                 440                 445

Leu Leu Leu Pro Leu Gln
        450

<210> SEQ ID NO 3
<211> LENGTH: 500
<212> TYPE: PRT
<213> ORGANISM: Artificial Sequence
<220> FEATURE:
<223> OTHER INFORMATION: Synthetic Polypeptide

<400> SEQUENCE: 3

Met Thr Trp Arg Ala Ala Ser Thr Cys Ala Ala Leu Leu Ile Leu
1               5                   10                  15

Leu Trp Ala Leu Thr Thr Glu Gly Asp Leu Lys Val Glu Met Met Ala
                20                  25                  30

Gly Gly Thr Gln Ile Thr Pro Leu Asn Asp Asn Val Thr Ile Phe Cys
            35                  40                  45

Asn Ile Phe Tyr Ser Gln Pro Leu Asn Ile Thr Ser Met Gly Ile Thr
    50                  55                  60

Trp Phe Trp Lys Ser Leu Thr Phe Asp Lys Glu Val Lys Val Phe Glu
65                  70                  75                  80

Phe Phe Gly Asp His Gln Glu Ala Phe Arg Pro Gly Ala Ile Val Ser
                85                  90                  95

Pro Trp Arg Leu Lys Ser Gly Asp Ala Ser Leu Arg Leu Pro Gly Ile
            100                 105                 110

Gln Leu Glu Glu Ala Gly Glu Tyr Arg Cys Glu Val Val Val Thr Pro
        115                 120                 125

Leu Lys Ala Gln Gly Thr Val Gln Leu Glu Val Val Ala Ser Pro Ala
    130                 135                 140

Ser Arg Leu Leu Leu Asp Gln Val Gly Met Lys Glu Asn Glu Asp Lys
145                 150                 155                 160

Tyr Met Cys Glu Ser Ser Gly Phe Tyr Pro Glu Ala Ile Asn Ile Thr
                165                 170                 175

Trp Glu Lys Gln Thr Gln Lys Phe Pro His Pro Ile Glu Ile Ser Glu
            180                 185                 190

Asp Val Ile Thr Gly Pro Thr Ile Lys Asn Met Asp Gly Thr Phe Asn
        195                 200                 205

Val Thr Ser Cys Leu Lys Leu Asn Ser Ser Gln Glu Asp Pro Gly Thr
    210                 215                 220

Val Tyr Gln Cys Val Val Arg His Ala Ser Leu His Thr Pro Leu Arg
225                 230                 235                 240

Ser Asn Phe Thr Leu Thr Ala Ala Arg His Ser Leu Ser Glu Thr Glu
                245                 250                 255

Lys Thr Asp Asn Phe Ser Ile His Trp Trp Pro Glu Pro Arg Ser Pro
```

-continued

```
                     260                 265                 270
Thr Ile Lys Pro Cys Pro Pro Cys Lys Cys Pro Ala Pro Asn Leu Glu
            275                 280                 285

Gly Gly Pro Ser Val Phe Ile Phe Pro Pro Lys Ile Lys Asp Val Leu
            290                 295                 300

Met Ile Ser Leu Ser Pro Ile Val Thr Cys Val Val Val Asp Val Ser
305                 310                 315                 320

Glu Asp Asp Pro Asp Val Gln Ile Ser Trp Phe Val Asn Asn Val Glu
            325                 330                 335

Val His Thr Ala Gln Thr Gln Thr His Arg Glu Asp Tyr Asn Ser Thr
            340                 345                 350

Leu Arg Val Val Ser Ala Leu Pro Ile Gln His Gln Asp Trp Met Ser
            355                 360                 365

Gly Lys Ala Phe Ala Cys Ala Val Asn Asn Lys Asp Leu Pro Ala Pro
            370                 375                 380

Ile Glu Arg Thr Ile Ser Lys Pro Lys Gly Ser Val Arg Ala Pro Gln
385                 390                 395                 400

Val Tyr Val Leu Pro Pro Pro Glu Glu Glu Met Thr Lys Lys Gln Val
            405                 410                 415

Thr Leu Thr Cys Met Val Thr Asp Phe Met Pro Glu Asp Ile Tyr Val
            420                 425                 430

Glu Trp Thr Asn Asn Gly Lys Thr Glu Leu Asn Tyr Lys Asn Thr Glu
            435                 440                 445

Pro Val Leu Asp Ser Asp Gly Ser Tyr Phe Met Tyr Ser Lys Leu Arg
            450                 455                 460

Val Glu Lys Lys Asn Trp Val Glu Arg Asn Ser Tyr Ser Cys Ser Val
465                 470                 475                 480

Val His Glu Gly Leu His Asn His His Thr Thr Lys Ser Phe Ser Arg
            485                 490                 495

Thr Pro Gly Lys
            500
```